(12) United States Patent
Prat Quinones et al.

(10) Patent No.: US 7,893,087 B2
(45) Date of Patent: Feb. 22, 2011

(54) QUINUCLIDINE DERIVATIVES AND MEDICINAL COMPOSITIONS CONTAINING THE SAME

(75) Inventors: Maria Prat Quinones, Barcelona (ES); Maria Dolors Fernandez Forner, Barcelona (ES); Maria Antonia Buil Albero, Barcelona (ES)

(73) Assignee: Almirall, S.A., Barcelona (ES)

( * ) Notice: Subject to any disclaimer, the term of this patent is extended or adjusted under 35 U.S.C. 154(b) by 901 days.

(21) Appl. No.: 11/515,335

(22) Filed: Aug. 31, 2006

(65) Prior Publication Data

US 2007/0129398 A1    Jun. 7, 2007

Related U.S. Application Data

(63) Continuation of application No. 10/250,447, filed as application No. PCT/EP01/15168 on Dec. 20, 2001, now Pat. No. 7,122,558.

(30) Foreign Application Priority Data

Dec. 28, 2000   (ES)  ............................. 200003130

(51) Int. Cl.
*A61K 31/4745*  (2006.01)
*A61K 31/407*   (2006.01)
*A61K 31/4178*  (2006.01)
*C07D 453/02*   (2006.01)

(52) U.S. Cl. .................... 514/305; 514/397; 514/412; 546/133; 548/453; 548/311.1

(58) Field of Classification Search .......... 514/305, 514/412, 397; 546/133; 548/453, 311.1
See application file for complete search history.

(56) References Cited

U.S. PATENT DOCUMENTS

| | | | |
|---|---|---|---|
| 4,082,756 A | 4/1978 | Bauman | |
| 4,431,627 A | 2/1984 | Eckelman et al. | |
| 4,465,834 A | 8/1984 | Baum et al. | |
| 4,644,033 A | 2/1987 | Gnanou et al. | |
| 4,675,326 A | 6/1987 | Amitai et al. | |
| 4,843,074 A | 6/1989 | Rzeszotarski et al. | |
| 5,654,314 A | 8/1997 | Banholzer et al. | |
| 6,750,226 B2 * | 6/2004 | Forner et al. ............... | 514/305 |
| 7,078,412 B2 * | 7/2006 | Fernandez Forner et al. ........................ | 514/305 |
| 7,109,210 B2 * | 9/2006 | Fernandez Forner et al. ........................ | 514/305 |
| 7,122,558 B2 * | 10/2006 | Prat Quinones et al. ..... | 514/305 |
| 7,196,098 B2 * | 3/2007 | Fernandez Forner et al. ........................ | 514/305 |
| 7,208,501 B2 * | 4/2007 | Buil Albero et al. ........ | 514/305 |
| 7,214,687 B2 * | 5/2007 | Fernandez Forner et al. ........................ | 514/305 |
| 7,312,231 B2 * | 12/2007 | Buil Albero et al. ........ | 514/305 |
| 7,358,260 B2 * | 4/2008 | Fernandez Forner et al. ........................ | 514/305 |
| 2007/0105897 A1 * | 5/2007 | Prat Quinones et al. ..... | 514/305 |
| 2008/0221155 A1 * | 9/2008 | Fernandez Forner et al. ........................ | 514/305 |

FOREIGN PATENT DOCUMENTS

| | | |
|---|---|---|
| EP | 0 404 737 A2 | 12/1990 |
| EP | 0 418 716 A1 | 3/1991 |
| EP | 0 424 021 A1 | 4/1991 |
| EP | 0 747 355 A1 | 12/1996 |
| EP | 0 801 067 A1 | 10/1997 |
| EP | 0 863 141 A1 | 9/1998 |
| EP | 0 930 298 A1 | 7/1999 |
| FR | 2 012 964 | 3/1970 |
| GB | 1 219 606 | 1/1971 |
| WO | WO-92/04346 A1 | 3/1992 |
| WO | WO-93/06098 A1 | 4/1993 |
| WO | WO-01/04118 A2 | 1/2001 |
| WO | WO-02/00652 A1 | 1/2002 |
| WO | WO-02/051841 A1 | 7/2002 |

OTHER PUBLICATIONS

Abrams et al., British journal of pharmacology, (Jul. 2006) vol. 148, No. 5, pp. 565-78. Electronic Publication: Jun. 5, 2006. Ref:151.*
Ehlert, F.J. (2003). "Contractile Role of M2 and M3 Muscarine Receptors in Gastrointestinal, Airway and Urinary Bladder Smooth Muscle" pp. 355-366.
Godovikov, N.N. et al. (May 12, 1986). "Synthesis and Muscarinolytic Activity of Quinu=Clindinyl Benzilate Alkyl Iodides," Chemical Abstract: Columbus, Ohio, 104(19):659.
Smith, A.B. et al. (1990). "2-Hydroxymethyl-2-Cyclopentenone," *Organic Synthesis Collective* 7:271-274.
So, I. et al. (2003). "Nonselective Cation Channels Activated by Stimulation of Muscarinic Receptors Mammalian Gastric Smooth Muscle" 39(6):231-247.

(Continued)

*Primary Examiner*—D. Margaret Seaman
*Assistant Examiner*—Niloofar Rahmani
(74) *Attorney, Agent, or Firm*—Morrison & Foerster LLP

(57) ABSTRACT

A compound of formula (I) is provided, wherein B, A, $R^1$, $R^2$, $R^3$, $R^4$, $R^5$ and $R^6$ are as defined herein and $X^-$ represents a pharmaceutically acceptable anion of a mono or polyvalent acid. Processes for the preparation of such compounds and pharmaceutical compositions containing them are also provided.

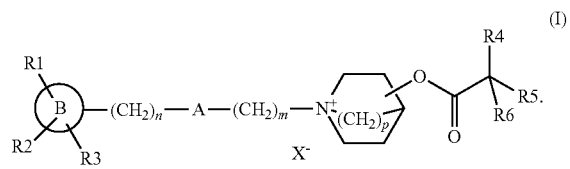

22 Claims, No Drawings

OTHER PUBLICATIONS

Waelbroeck, M. et al. (1990). "Binding of Selective Antagonists to Four Muscarinic Receptors (M1 to M4) in Rat Forebrain" *Molecular Pharmacology* 38:267-273.

Mikhlina, E.E. et al. (1982) "Synthesis and Cholinolytic Properties of Esters of 3-Hydroxyquinuclidine," *Pharmaceutical Chemistry Journal* (translated from *Khimiko-Farmatsevticheskii Zhurnal* 15(8):55-57), 15(8):569-572.

Rzeszotarski, W.J. et al. (1982) "Analogues of 3-Quinuclidinyl Benzilate," *J. Med. Chem.* 25(9):1103-1106.

Audia, V.H. et al. (1990). "Synthesis of Some 3-(1-Azabicyclo[2.2.2]Octyl) 3-Amino-2-Hydroxy-2-Phenylpropionates: Profile of Antimuscarinic Efficacy and Selectivity," *Journal of Medicinal Chemistry* 33(1):307-310.

* cited by examiner

QUINUCLIDINE DERIVATIVES AND MEDICINAL COMPOSITIONS CONTAINING THE SAME

CROSS-REFERENCE TO RELATED APPLICATIONS

This application is a continuation of U.S. patent application Ser. No. 10/250,447, filed Jun. 27, 2003, having a 371(c) filing date of Dec. 8, 2003, which is a National Phase filing under 35 U.S.C. §371(c) of International Patent Application No. PCT/EP01/15168, filed Dec. 20, 2001, which claims priority to Spanish Application No. 200003130, filed Dec. 28, 2000. The disclosures of which are herein incorporated by reference in their entirety.

This invention relates to new therapeutically useful quinuclidine derivatives, to some processes for their preparation and to pharmaceutical compositions containing them.

The novel structures according to the invention are antimuscarinic agents with a potent and long lasting effect. In particular, these compounds show high affinity for muscarinic M3 receptors. This subtype of muscarinic receptor is present in glands and smooth muscle and mediates the excitatory effects of the parasympathetic system on glandular secretion and on the contraction of visceral smooth muscle (Chapter 6, *Cholinergic Transmission*, in H. P. Rang et al., *Pharmacology*, Churchill Livingstone, N.Y., 1995).

M3 antagonists are therefore known to be useful for treating diseases characterised by an increased parasympathetic tone, by excessive glandular secretion or by smooth muscle contraction (R. M. Eglen and S. S. Hegde, (1997), Drug News Perspect., 10(8):462-469).

Examples of this kind of diseases are respiratory disorders such as chronic obstructive pulmonary disease (COPD), bronchitis, bronchial hyperreactivity, asthma, cough and rhinitis; urological disorders such as urinary incontinence, pollakiuria, neurogenic or unstable bladder, cystospasm and chronic cystitis; gastrointestinal disorders such as irritable bowel syndrome, spastic colitis, diverticulitis and peptic ulceration; and cardiovascular disorders such as vagally induced sinus bradycardia (Chapter 7, *Muscarinic Receptor Agonists and Antagonists*, in *Goodman and Gilman's The Pharmacological Basis of Therapeutics*, 10 the edition, McGraw Hill, Ney York, 2001).

The compounds of the invention can be used alone or in association with other drugs commonly regarded as effective in the treatment of these diseases. For example, they can be administered in combination with $\beta_2$-agonists, steroids, antiallergic drugs, phosphodiesterase IV inhibitors an/or leukotriene D4 (LTD4) antagonists for simultaneous, separate or sequential use in the treatment of a respiratory disease. The claimed compounds are useful for the treatment of the respiratory diseases detailed above in association with $\beta_2$-agonists, steroids, antiallergic drugs or phosphodiesterase IV inhibitors.

Compounds with related structures have been described as anti-cholinergic and/or anti-spasmodics agents in several patents.

For example, FR 2012964 describes quinuclidinol derivatives of the formula

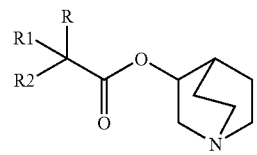

in which R is H, OH or an alkyl group having 1 to 4 carbon atoms; $R^1$ is a phenyl or thienyl group; and $R^2$ is a cyclohexyl, cyclopentyl or thienyl group, or, when R is H, $R^1$ and $R^2$ together with the carbon atom to which they are attached, form a tricyclic group of the formula:

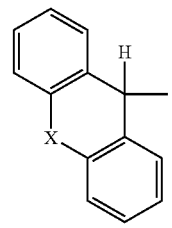

in which X is —O—, —S— or —CH$_2$—, or an acid addition or quaternary ammonium salt thereof.

In U.S. Pat. No. 4,465,834 a class of anticholinergic drugs having the formula

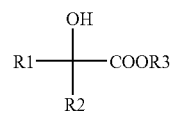

are described, in which $R^1$ is a carbocyclic or branched aliphatic group of 3 to 8 carbon atoms (such as phenyl, cyclohexyl, cyclopentyl, cyclopropyl, cycloheptyl, and isopropyl), $R^2$ is a branched or linear aliphatic group containing 3 to 10 carbon atoms with 1 or 2 olefinic or acetylenic bonds, or is a phenylethinyl, a styryl, or an ethynyl group, and $R^3$ is an alkyl or cyclic group of 4 to 12 carbon atoms containing a tertiary amino nitrogen. The compounds of the invention are also claimed as either the free base or the acid-addition and quaternary ammonium salt forms thereof.

In U.S. Pat. No. 4,843,074 products of formula

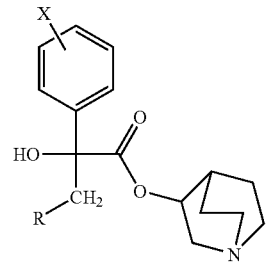

are described, wherein X=H, halogen, lower alkyl, lower alkoxy, hydroxy and R=morpholinyl, thiomorpholinyl, piperidinyl, 1,4-dioxa-8-azaspiro[4,5]decanyl, 4-(2,6-dimethyl- U.S. Pat. No. 4,644,003 describes esters of 3-quinuclidinol of alpha disubstituted glicolic acids

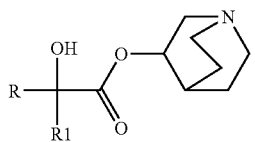

and their pharmaceutically acceptable salts, where R is phenyl, unsubstituted or substituted up to three substituents including alkoxy, halogen, nitro, amino, alkylamino, dialkylamino, acylamino, and trifluoromethyl; and wherein $R^1$ is hydrogen, alkyl, cycloalkyl, alkenyl, cycloalkenyl, alkynyl, alkyloxyalkyl, cycloalkyloxyalkyl, haloalkyl or haloalkenyl.

In WO 92/04346 are described compounds of formula

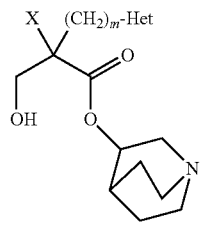

and their pharmaceutically acceptable salts, where X is a phenyl (optionally substituted) or a thienyl group and "Het" is either (a) a five membered nitrogen-containing heterocyclic group, (b) an oxadiazolyl or thiadiazolyl group, or (c) a six membered nitrogen-containing heterocyclic group, and m is 1 or 2. (For a more detailed description, see the above mentioned publication)

Azoniabicyclic compounds of a general structure related to the compounds of the invention are disclosed in WO 01/04118.

The present invention provides new quinuclidine ester derivatives with potent antagonist activity at muscarinic M3 receptors which have the chemical structure described in formula (I):

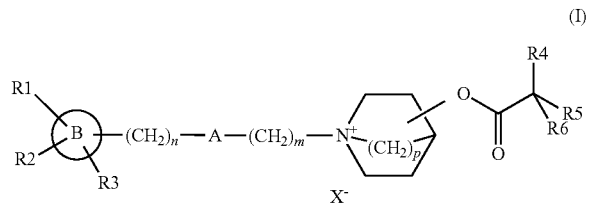

wherein B is a phenyl ring, a 5 to 10-membered heteroaromatic group containing one or more heteroatoms, or a naphthalenyl, 5,6,7,8-tetrahydronaphthalenyl, benzo[1,3]dioxolyl, or biphenyl group; $R^1$, $R^2$ and $R^3$ each independently represent a hydrogen or halogen atom, or a hydroxy group, a phenyl group, —$OR^7$, —$SR^7$, —$NR^7R^8$, —$NHCOR^7$, —$CONR^7R^8$, —CN, —$NO_2$, —$COOR^7$ or —$CF_3$ group, or a straight or branched, substituted or unsubstituted lower alkyl group, wherein $R^7$ and $R^8$ each independently represent a hydrogen atom, a straight or branched lower alkyl group, or together form an alicyclic ring; or $R^1$ and $R^2$ together form an aromatic or alicyclic ring or a heterocyclic group;

n is an integer from 0 to 4;

A represents a group selected from —$CH_2$—, —CH=$CR^9$—, —$CR^9$=CH—, —$CR^9R^{10}$—, —CO—, —O—, —S—, —S(O)—, —$S(O)_2$— and —$NR^9$—, wherein $R^9$ and $R^{10}$ each independently represent a hydrogen atom, a straight or branched lower alkyl group, or together form an alicyclic ring;

m is an integer from 0 to 8, provided that when m=0, A is not —$CH_2$—;

p is an integer from 1 to 2 and the substitution in the azonia bicyclic ring may be in the 2,3 or 4 position including all possible configurations of the asymmetric carbons;

$R^4$ represents a group of structure:

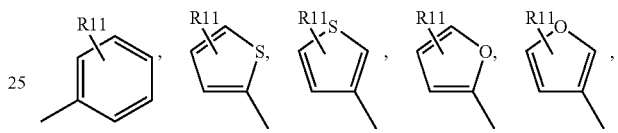

wherein $R^{11}$ represents a hydrogen or halogen atom, a hydroxy group, an alkoxy group, a nitro group, a cyano group, —$CO_2R^{12}$ or —$N^{R12R13}$, wherein $R^{12}$ and $R^{13}$ are identical or different and are selected from hydrogen and straight or branched lower alkyl groups, or a straight or branched, substituted or unsubstituted lower alkyl group;

$R^5$ represents an alkyl group of 1 to 7 carbon atoms, an alkenyl group containing 2 to 7 carbon atoms, an alkynyl group containing 2 to 7 carbon atoms, a cycloalkyl group of 3 to 7 carbon atoms, or a group of formula

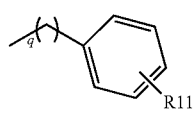

wherein q=1 or 2 and $R^{11}$ is as defined above;

$R^6$ represents a hydrogen atom, a hydroxy group, a methyl group or a —$CH_2OH$ group. The asymmetric carbon in the alpha position to the ester group, which is substituted by $R^4$, $R^5$, and $R^6$ may have R or S configuration.

$X^-$ represents a pharmaceutically acceptable anion of a mono or polyvalent acid.

In the quaternary ammonium compounds of the present invention represented by formula (I), an equivalent of an anion ($X^-$) is associated with the positive charge of the N atom $X^-$ may be an anion of various mineral acids such as, for example, chloride, bromide, iodide, sulfate, nitrate, phosphate, or an anion of an organic acid such as, for example, acetate, maleate, fumarate, citrate, oxalate, succinate, tartrate, malate, mandelate, trifluoroacetate, methanesulfonate and p-toluenesulfonate. $X^-$ is preferably an anion selected from chloride, bromide, iodide, sulphate, nitrate, acetate, maleate, oxalate, succinate or trifluoroacetate. More preferably $X^-$ is chloride, bromide, trifluoroacetate or methanesulphonate.

The compounds of the present invention represented by the formula (I) described above, which may have one or more asymmetric carbons, include all the possible stereoisomers. The single isomers and mixtures of the isomers fall within the scope of the present invention.

As used herein, an alkyl group is typically a lower alkyl group. A lower alkyl group preferably contains 1 to 8, preferably 1 to 6 and more preferably 1 to 4 carbon atoms. In particular it is preferred that such an alkyl group is represented by a methyl, ethyl, propyl, including i-propyl, or butyl including a n-butyl, sec-butyl and tert-butyl group. An alkyl group containing 1 to 7 carbon atoms as mentioned herein, such as that represented by $R^5$, may be a $C_{1-4}$ alkyl group as mentioned above or a straight or branched pentyl, hexyl or heptyl group.

Optionally substituted lower alkyl groups mentioned herein include straight or branched alkyl groups containing from 1 to 6, preferably from 1 to 4, carbon atoms as mentioned above, which may be unsubstituted or substituted in any position by one or more substituents, for example by 1, 2 or 3 substituents. When two or more substituents are present, each substituent may be the same or different. The substituent(s) are typically halogen atoms or hydroxy or alkoxy groups, preferably hydroxy or alkoxy groups.

Alkenyl groups having 2 to 7 carbon atoms mentioned herein, such as those represented by the group $R^5$, are straight or branched groups such as ethenyl, or straight or branched propenyl, butenyl, pentenyl, hexenyl or heptenyl. The double bond may be in any position in the alkenyl group, such as on the terminal bond.

Alkynyl groups having 2 to 7 carbon atoms mentioned herein, such as those represented by the group. $R^5$, are straight or branched groups such as ethynyl, propynyl or straight or branched butynyl, pentynyl, hexynyl or heptynyl. The triple bond may be in any position in the alkynyl group, such as on the terminal bond.

Alkoxy groups mentioned herein, such as those that may be present in the group B, are typically lower alkoxy groups, that is groups containing from 1 to 6 carbon atoms, preferably from 1 to 4 carbon atoms, the hydrocarbon chain being branched or straight. Preferred alkoxy groups include methoxy, ethoxy, n-propoxy, i-propoxy, n-butoxy, sec-butoxy and t-butoxy.

Cycloalkyl groups and alicyclic groups mentioned herein, unless otherwise specified, typically contain from 3 to 8 carbon atoms, preferably from 3 to 6 carbon atoms. Cycloalkyl groups and alicyclic rings of 3 to 6 carbon atoms include cyclopropyl, cyclobutyl, cyclopentyl and cyclohexyl. Cycloalkyl groups containing from 3 to 7 carbon atoms include cycloalkyl groups of 3 to 6 carbon atoms and cycloheptyl.

The aromatic ring mentioned in relation to $R^1$ and $R^2$ typically contains from 5 to 14, preferably 5 to 10 carbon atoms. Examples of aromatic groups include cyclopentadienyl, phenyl and naphthalenyl.

A heterocyclic or heteroaromatic group mentioned herein is typically a 5 to 10 membered group, such as a 5, 6 or 7 membered group, containing one or more heteroatoms selected from N, S and O. Typically, 1, 2, 3 or 4 heteroatoms are present, preferably 1 or 2 heteroatoms. A heterocyclic or heteroaromatic group may be a single ring or two or more fused rings wherein at least one ring contains a heteroatom. Examples of heterocyclic groups include piperidyl, pyrrolidyl, piperazinyl, morpholinyl, thiomorpholinyl, pyrrolyl, imidazolyl, imidazolidinyl, pyrazolinyl, indolinyl, isoindolinyl, pyridyl, pyrazinyl, pyrimidinyl, pyridazinyl, indolizinyl, isoindolyl, indolyl, indazolyl, purinyl, quinolizinyl, isoquinolyl, quinolyl, phthalazinyl, naphthyridinyl, quinoxalinyl, quinazolinyl, cinnolinyl, pteridinyl, quinuclidinyl, triazolyl, pyrazolyl, tetrazolyl and thienyl. Examples of heteroaromatic groups include pyridyl, thienyl, furyl, pyrrolyl, imidazolyl, benzothiazolyl, pyridinyl, pyrazolyl, pyrazinyl, pyrimidinyl, pyridazinyl, indolyl, indazolyl, purinyl, quinolyl, isoquinolyl, phthalazinyl, naphthyridinyl, quinoxalinyl, quinazolinyl, cinnolinyl, triazolyl and pyrazolyl.

As used herein a halogen atom includes a fluorine, chlorine, bromine or iodine atom, typically a fluorine, chlorine or bromine atom.

Preferred compounds of formula (I) are those wherein B represents a phenyl, pyrrolyl, thienyl, furyl, biphenyl, naphthalenyl, 5,6,7,8-tetrahydronaphthalenyl, benzo[1,3]dioxolyl, imidazolyl or benzothiazolyl group, in particular a phenyl, pyrrolyl, thienyl, furyl, biphenyl, naphthalenyl, 5,6,7,8-tetrahydronaphthalenyl or benzo[1,3]dioxolyl group such as a phenyl, thienyl or pyrrolyl group.

B may be unsubstituted or substituted with one, two or three groups ($R^1$ to $R^3$) which may be in any position on the ring. Typically it is unsubstituted or substituted with one group, for example when B is a phenyl group it may be substituted in the 2, 3 or 4 position. Typically, $R^1$, $R^2$ and $R^3$ each independently represent a hydrogen or halogen atom, or a hydroxy, methyl, tert-butyl, —CH$_2$OH, 3-hydroxypropyl, —OMe, —NMe$_2$, —NHCOMe, —CONH$_2$, —CN, —NO$_2$, —COOMe or —CF$_3$ group, in particular a hydrogen, fluorine or chlorine atom or a hydroxy, methyl, —CH$_2$OH, —OMe, —NMe$_2$, —NHCOMe, —CONH$_2$, —CN, —NO$_2$, —COOMe or —CF$_3$ group. The most preferred groups $R^1$, $R^2$ and $R^3$ are hydrogen, fluorine, chlorine or hydroxy.

Examples of substituted phenyl groups which may represent B are tolyl including o-, m- and p-tolyl, 3-cyanophenyl, 2-, 3- and 4-hydroxyphenyl and 2-, 3- and 4-fluorophenyl.

Preferred compounds of formula (I) are those wherein n=0 or 1; m is an integer from 1 to 6, particularly 1, 2 or 3; and A represents a —CH$_2$—, —CH═CH—, —CO—, —NMe-, —O— or —S— group, in particular a —CH$_2$—, —CH═CH—, —O— or —S— group, for example a —CH$_2$—, —CH═CH— or —O— group.

More preferred salts of formula (I) are those wherein the azoniabicyclo group is substituted on the nitrogen atom with a 3-phenoxypropyl, 2-phenoxyethyl, 3-phenylallyl, phenethyl, 4-phenylbutyl, 3-phenylpropyl, 3-(2-hydroxyphenoxy)propyl, 3-(4-fluorophenoxy)propyl, 2-benzyloxyethyl, 3-pyrrol-1-ylpropyl, 2-thien-2-ylethyl, 3-thien-2-ylpropyl, 3-phenylaminopropyl, 3-(methylphenylamino)propyl, 3-phenylsulfanylpropyl, 3-o-tolyloxypropyl, 3-(2,4,6-trimethylphenoxy)propyl, 3-(2-tert-butyl-6-methylphenoxy)propyl, 3-(biphenyl-4-yloxy)propyl, 3-(5,6,7,8-tetrahydronaphthalen-2-yloxy)-propyl, 3-(naphthalen-2-yloxy)propyl, 3-(naphthalen-1-yloxy)propyl, 3-(2-chlorophenoxy)propyl, 3-(2,4-difluorophenoxy)propyl, 3-(3-trifluoromethylphenoxy)propyl, 3-(3-cyanophenoxy)propyl, 3-(4-cyanophenoxy)propyl, 3-(3-methoxyphenoxy)propyl, 3-(4-methoxyphenoxy)propyl, 3-(benzo[1,3]dioxol-5-yloxy)propyl, 3-(2-carbamoylphenoxy)propyl, 3-(3-dimethylaminophenoxy)propyl, 3-(4-nitrophenoxy)propyl, 3-(3-nitrophenoxy)propyl, 3-(4-acetylaminophenoxy)propyl, 3-(4-methoxycarbonylphenoxy)propyl, 3-[4-(3-hydroxypropyl)phenoxy]propyl, 3-(2-hydroxymethylphenoxy)propyl, 3-(3-hydroxymethylphenoxy)propyl, 3-(4-hydroxymethylphenoxy)propyl, 3-(2-hydroxyphenoxy)propyl, 3-(4-hydroxyphenoxy)propyl, 3-(3- hydroxyphenoxy)propyl, 4-oxo-4-thien-2-ylbutyl, 3-(1-methyl-[1H]-imidazol-2-ylsulfanyl)propyl, 3-(benzothiazol-2-yloxy)propyl, 3-benzyloxypropyl, 6-(4-phenylbutoxy)hexyl, 4-phenoxybutyl, 4-(4-fluorophenyl)-4-oxobutyl or 4-oxo-4-phenylbutyl group. Especially preferred salts are those wherein the azoniabicyclo group is substituted on the nitrogen atom with a 3-phenoxypropyl, 2-phenoxyethyl, 3-phenylallyl, phenethyl, 3-phenylpropyl, 3-(3-hydroxyphenoxy) propyl, 3-(4-fluorophenoxy)propyl, 3-thien-2-ylpropyl group, 4-oxo-4-thien-2-ylbutyl, 2-benzyloxyethyl, 3-o-tolyloxypropyl, 3-(3-cyanophenoxy)propyl, 3-(methylphenylamino)propyl, 3-phenylsulfanylpropyl, 4-oxo-4-phenylbutyl, 3-(2-chlorophenoxy)propyl, 3-(2,4-difluorophenoxy) propyl, 3-(4-methoxyphenoxy)propyl, 3-(benzo[1,3]dioxol-5-yloxy)propyl. Examples of especially preferred salts are those wherein the azoniabicyclo group is substituted on the nitrogen atom with a 3-phenoxypropyl, 2-phenoxyethyl, 3-phenylallyl, phenethyl, 3-phenylpropyl, 3-(3-hydroxyphenoxy)propyl, 3-(4-fluorophenoxy)propyl or 3-thien-2-ylpropyl group.

Further preferred compounds of formula (I) are those wherein $R^4$ represents a phenyl, 2-thienyl, 3-thienyl, 2-furyl or 3-furyl group. $R^{11}$ preferably represents a hydrogen or halogen atom or an unsubstituted lower alkyl group such as methyl or ethyl. Most preferably $R^{11}$ is a hydrogen atom. Therefore, for example, $R^4$ may represent an unsubstituted phenyl, 2-thienyl or 2-furyl group. Alternatively, $R^4$ may represent an unsubstituted phenyl or 2-thienyl group. Preferably, $R^5$ represents a benzyl, phenethyl, cyclopentyl, cyclohexyl, $C_{2-5}$ alkyl, $C_{2-5}$ alkenyl or $C_{2-5}$ alkynyl group, particularly a cyclopentyl, cyclohexyl, pentyl, allyl, vinyl, propynyl, phenethyl or benzyl group. Alternatively, $R^5$ represents a benzyl, cyclopentyl, cyclohexyl, $C_{2-5}$ alkyl, $C_{2-5}$ alkenyl or $C_{2-5}$ alkynyl group, particularly a cyclopentyl, cyclohexyl, pentyl, allyl, vinyl, propynyl or benzyl group. The asymmetric carbon alpha to the ester group, which is substituted by $R^4$, $R^5$ and $R^6$ may have R or S configuration.

Preferred compounds of formula (I) are those wherein the group —O—CO—C($R^4$)($R^5$)($R^6$) represents a group selected from 2-cyclopentyl-2-hydroxy-2-thien-2-ylacetoxy; 2,3-diphenylpropionyloxy; 2-hydroxymethyl-2,3-diphenylpropionyloxy; 2-hydroxy-2,3-diphenylpropionyloxy; 2-hydroxy-3-phenyl-2-thien-2-ylpropionyloxy; 2-hydroxy-2-thien-2-ylpent-4-enoyloxy; 2-hydroxy-2-thien-2-ylheptanoyloxy; 2-hydroxy-2-thien-2-ylpent-3-ynoyloxy; 2-hydroxy-2-thien-2-ylbut-3-enoyloxy; 2-cyclopentyl-2-fur-2-yl-2-hydroxyacetoxy; 2-cyclohexyl-2-hydroxy-2-phenylacetoxy; 2-cyclohexyl-2-fur-2-yl-2-hydroxyacetoxy, 2-cyclopentyl-2-hydroxy-2-phenylacetoxy, 2-cyclohexyl-2-hydroxy-2-thien-2-ylacetoxy and 2-hydroxy-4-phenyl-2-thien-2-ylbutanoyloxy. Examples of the group —O—CO—C($R^4$)($R^5$)($R^6$) are 2-cyclopentyl-2-hydroxy-2-thien-2-ylacetoxy; 2,3-diphenylpropionyloxy; 2-hydroxymethyl-2,3-diphenylpropionyloxy; 2-hydroxy-2,3-diphenylpropionyloxy; 2-hydroxy-3-phenyl-2-thien-2-ylpropionyloxy; 2-hydroxy-2-thien-2-ylpent-4-enoyloxy; 2-hydroxy-2-thien-2-ylheptanoyloxy; 2-hydroxy-2-thien-2-ylpent-3-ynoyloxy; 2-hydroxy-2-thien-2-ylbut-3-enoyloxy; 2-cyclopentyl-2-fur-2-yl-2-hydroxyacetoxy; 2-cyclohexyl-2-hydroxy-2-phenylacetoxy and 2-cyclohexyl-2-fur-2-yl-2-hydroxyacetoxy.

In the most preferred embodiments of the invention p is 2, the azoniabicyclo[2.2.2]octane ring is substituted in the 3 position, and this substituted carbon atom has (R)-configuration.

The following compounds are intended to illustrate but not to limit the scope of the present invention:

(3R)-3-(2,3-Diphenylpropionyloxy)-1-(3-phenoxypropyl)-1-azoniabicyclo[2.2.2]octane trifluoroacetate (3R)-3-(2,3-Diphenylpropionyloxy)-1-(3-thien-2-ylpropyl)-1-azoniabicyclo[2.2.2]octane trifluoroacetate (3R)-3-[(2*)-2-Hydroxymethyl-2,3-diphenylpropionyloxy]-1-(3-thien-2-ylpropyl)-1-azoniabicyclo[2.2.2]octane trifluoroacetate (diastereomer 1)

(3R)-3-[(2*)-2-Hydroxymethyl-2,3-diphenylpropionyloxy]-1-phenethyl-1-azoniabicyclo[2.2.2]octane trifluoroacetate (diastereomer 1)

(3R)-3-[(2*)-2-Hydroxymethyl-2,3-diphenylpropionyloxy]-1-(3-thien-2-ylpropyl)-1-azoniabicyclo[2.2.2]octane trifluoroacetate (diastereomer 2)

(3R)-3-[(2*)-2-Hydroxymethyl-2,3-diphenylpropionyloxy]-1-phenethyl-1-azoniabicyclo[2.2.2]octane trifluoroacetate (diastereomer 2)

(3R)-3-[(2*)-2-Hydroxy-2,3-diphenylpropionyloxy]-1-(3-phenoxypropyl)-1-azoniabicyclo[2.2.2]octane bromide (diastereomer 1)

(3R)-3-[(2*)-2-Hydroxy-2,3-diphenylpropionyloxy]-1-(2-phenoxyethyl)-1-azoniabicyclo[2.2.2]octane bromide (diastereomer 1)

(3R)-3-[(2*)-2-Hydroxy-2,3-diphenylpropionyloxy]-1-(3-phenoxypropyl)-1-azoniabicyclo[2.2.2]octane trifluoroacetate (diastereomer 2)

(3R)-3-[(2*)-2-Hydroxy-2,3-diphenylpropionyloxy]-1-(2-phenoxyethyl)-1-azoniabicyclo[2.2.2]octane trifluoroacetate (diastereomer 2)

(3R)-3-(2-Hydroxy-3-phenyl-2-thien-2-ylpropionyloxy)-1-(3-phenoxypropyl)-1-azoniabicyclo[2.2.2]octane trifluoroacetate (3R)-3-(2-Hydroxy-3-phenyl-2-thien-2-ylpropionyloxy)-1-(3-thien-2-ylpropyl)-1-azoniabicyclo[2.2.2]octane trifluoroacetate (3R)-3-(2-Hydroxy-2-thien-2-ylpent-4-enoyloxy)-1-(3-phenoxypropyl)-1-azoniabicyclo[2.2.2]octane bromide (3R)-3-(2-Hydroxy-2-thien-2-ylpent-4-enoyloxy)-1-(3-thien-2-ylpropyl)-1-azoniabicyclo[2.2.2]octane trifluoroacetate (3R)-3-(2-Hydroxy-2-thien-2-ylpent-4-enoyloxy)-1-(2-phenoxyethyl)-1-azoniabicyclo[2.2.2]octane bromide (3R)-3-(2-Hydroxy-2-thien-2-ylheptanoyloxy)-1-(3-phenoxypropyl)-1-azoniabicyclo[2.2.2]octane trifluoroacetate (3R)-3-(2-Hydroxy-2-thien-2-ylheptanoyloxy)-1-(3-thien-2-ylpropyl)-1-azoniabicyclo[2.2.2]octane trifluoroacetate (3R)-3-(2-Hydroxy-2-thien-2-ylpent-3-ynoyloxy)-1-(3-phenoxypropyl)-1-azoniabicyclo[2.2.2]octane trifluoroacetate (3R)-3-(2-Hydroxy-2-thien-2-ylpent-3-ynoyloxy)-1-(3-thien-2-ylpropyl)-1-azoniabicyclo[2.2.2]octane trifluoroacetate (3R)-3-(2-Hydroxy-2-thien-2-ylbut-3-enoyloxy)-1-(3-phenoxypropyl)-1-azoniabicyclo[2.2.2]octane trifluoroacetate (3R)-3-(2-Hydroxy-2-thien-2-ylbut-3-enoyloxy)-1-(3-thien-2-ylpropyl)-1-azoniabicyclo[2.2.2]octane trifluoroacetate (3R)-3-[(2S)-2-Cyclopentyl-2-hydroxy-2-thien-2-ylacetoxy]-1-(3-phenoxypropyl)-1-azoniabicyclo[2.2.2]octane bromide (3R)-3-[(2S)-2-Cyclopentyl-2-hydroxy-2-thien-2-ylacetoxy]-1-(3-thien-2-ylpropyl)-1-azoniabicyclo[2.2.2]octane trifluoroacetate (3R)-3-[(2S)-2-Cyclopentyl-2-hydroxy-2-thien-2-ylacetoxy]-1-(2-phenoxyethyl)-1-azoniabicyclo[2.2.2]octane bromide (3R)-3-[(2S)-2-Cyclopentyl-2-hydroxy-2-thien-2-ylacetoxy]-1-phenethyl-1-azoniabicyclo[2.2.2]octane trifluoroacetate (3R)-3-[(2S)-2-Cyclopentyl-2-hydroxy-2-thien-2-ylacetoxy]-1-(3-phenylpropyl)-1-azoniabicyclo[2.2.2]octane trifluoroacetate (3R)-3-[(2S)-2-Cyclopentyl-2-hydroxy-2-thien-2-ylacetoxy]-1-(3-phenylallyl)-1-azoniabicyclo[2.2.2]octane trifluoroacetate (3R)-3-[(2S)-2-Cyclopentyl-2-hydroxy-2-thien-2-ylacetoxy]-1-[3-(4-fluorophenoxy)propyl]-1-azoniabicyclo[2.2.2]octane trifluoroacetate (3R)-3-[(2)-2-Cyclopentyl-2-hydroxy-2-thien-2-ylacetoxy]-1-(4-oxo-4-thien-2-ylbutyl)-1-azoniabicyclo[2.2.2]octane trifluoroacetate (3R)-3-[(2S)-2-Cyclopentyl-2-hydroxy-2-thien-2-ylacetoxy]-1-[4-(4-fluorophenyl)-4-oxobutyl]-1-azoniabicyclo[2.2.2]octane trifluoroacetate (3R)-3-[(2S)-2-Cyclopentyl-2-hydroxy-2-thien-2-ylacetoxy]-1-[3-(3-hydroxyphenoxy)propyl]-1-azoniabicyclo[2.2.2]octane trifluoroacetate 1-(2-Benzyloxyethyl)-(3R)-3-[(2S)-2-cyclopentyl-2-hydroxy-2-thien-2-ylacetoxy]-1-azoniabicyclo[2.2.2]octane trifluoroacetate (3R)-3-[(2S)-2-Cyclopentyl-2-hydroxy-2-thien-2-ylacetoxy]-1-(3-o-tolyloxypropyl)-1-azoniabicyclo[2.2.2]octane trifluoroacetate 1-[3-(3-Cyanophenoxy)propyl]-(3R)-3-[(2S)-2-cyclopentyl-2-hydroxy-2-thien-2-ylacetoxy]-1-azoniabicyclo[2.2.2]octane trifluoroacetate (3R)-3-[(2S)-2-Cyclopentyl-2-hydroxy-2-thien-2-ylacetoxy]-1-[3-(naphthalen-1-yloxy)propyl]-1-azoniabicyclo[2.2.2]octane trifluoroacetate (3R)-3-[(2S)-2-Cyclopentyl-2-hydroxy-2-thien-2-ylacetoxy]-1-[3-(methylphenylamino)propyl]-1-azoniabicyclo[2.2.2]octane trifluoroacetate (3R)-3-[(2S)-2-Cyclopentyl-2-hydroxy-2-thien-2-ylacetoxy]-1-(3-phenylsulfanylpropyl)-1-azoniabicyclo[2.2.2]octane trifluoroacetate (3R)-3-[(2S)-2-Cyclopentyl-2-hydroxy-2-thien-2-ylacetoxy]-1-(4-oxo-4-phenylbutyl)-1-azoniabicyclo[2.2.2]octane trifluoroacetate (3R)-3-[(2S)-2-Cyclopentyl-2-hydroxy-2-thien-2-ylacetoxy]-1-[3-(2,4,6-trimethylphenoxy)propyl]-1-azoniabicyclo[2.2.2]octane trifluoroacetate 1-[3-(2-Chlorophenoxy)propyl]-(3R-3-[(2S)-2-cyclopentyl-2-hydroxy-2-thien-2-ylacetoxy]-1-azoniabicyclo[2.2.2]octane trifluoroacetate (3R)-3-[(2S)-2-Cyclopentyl-2-hydroxy-2-thien-2-ylacetoxy]-1-[3-(3-trifluoromethylphenoxy)propyl]-1-azoniabicyclo[2.2.2]octane trifluoroacetate 1-[3-(Biphenyl-4-yloxy)propyl]-(3R)-3-[(2)-2-cyclopentyl-2-hydroxy-2-thien-2-ylacetoxy]-1-azoniabicyclo[2.2.2]octane trifluoroacetate (3R)-3-[(2S)-2-Cyclopentyl-2-hydroxy-2-thien-2-ylacetoxy]-1-[3-(2,4-difluorophenoxy)propyl]-1-azoniabicyclo[2.2.2]octane trifluoroacetate (3R)-3-[(2S)-2-Cyclopentyl-2-hydroxy-2-thien-2-ylacetoxy]-1-[3-(4-methoxyphenoxy)propyl]-1-azoniabicyclo[2.2.2]octane trifluoroacetate (3R)-3-[(2S)-2-Cyclopentyl-2-hydroxy-2-thien-2-ylacetoxy]-1-[3-(5,6,7,8-tetrahydronaphthalen-2-yloxy)propyl]-1-azoniabicyclo[2.2.2]octane trifluoroacetate 1-[3-(Benzo[1,3]dioxol-5-yloxy)propyl]-(3R)-3-[(2S)-2-cyclopentyl-2-hydroxy-2-thien-2-ylacetoxy]-1-azoniabicyclo[2.2.2]octane trifluoroacetate 1-[3-(2-Carbamoylphenoxy)propyl]-(3R)-3-[(2S)-2-cyclopentyl-2-hydroxy-2-thien-2-ylacetoxy]-1-azoniabicyclo[2.2.2]octane trifluoroacetate (3R)-3-[(2S)-2-Cyclopentyl-2-hydroxy-2-thien-2-ylacetoxy]-1-[3-(3-dimethylaminophenoxy)propyl]-1-azoniabicyclo[2.2.2]octane trifluoroacetate 1-[3-(4-Acetylaminophenoxy)propyl]-(3R)-3-[(2S)-2-cyclopentyl-2-hydroxy-2-thien-2-ylacetoxy]-1-azoniabicyclo[2.2.2]octane trifluoroacetate (3R)-3-[(2S)-2-Cyclopentyl-2-hydroxy-2-thien-2-ylacetoxy]-1-[3-(4-methoxycarbonylphenoxy)propyl]-1-azoniabicyclo[2.2.2]octane trifluoroacetate (3R)-3-[(2S)-2-Cyclopentyl-2-hydroxy-2-thien-2-ylacetoxy]-1-[3-(4-nitrophenoxy)propyl]-1-azoniabicyclo[2.2.2]octane trifluoroacetate (3R)-3-[(2S)-2-Cyclopentyl-2-hydroxy-2-thien-2-ylacetoxy]-1-[3-(4-hydroxymethylphenoxy)propyl]-1-azoniabicyclo[2.2.2]octane trifluoroacetate (3R)-3-[(2R)-2-cyclopentyl-2-hydroxy-2-thien-2-ylacetoxy]-1-(3-phenoxypropyl)-1-azoniabicyclo[2.2.2]octane bromide (3R)-3-[(2R)-2-Cyclopentyl-2-hydroxy-2-thien-2-ylacetoxy]-1-(3-thien-2-ylpropyl)-1-azoniabicyclo[2.2.2]octane trifluoroacetate (3R)-3-[(2R)-2-Cyclopentyl-2-hydroxy-2-thien-2-ylacetoxy]-1-(2-phenoxyethyl)-1-azoniabicyclo[2.2.2]octane trifluoroacetate (3R)-3-[(2R)-2-Cyclopentyl-2-hydroxy-2-thien-2-ylacetoxy]-1-phenethyl-1-azoniabicyclo[2.2.2]octane trifluoroacetate (3R)-3-[(2R)-2-Cyclopentyl-2-hydroxy-2-thien-2-ylacetoxy]-1-(3-phenylpropyl)-1-azoniabicyclo[2.2.2]octane trifluoroacetate (3R)-3-[(2R)-2-Cyclopentyl-2-hydroxy-2-thien-2-ylacetoxy]-1-(3-phenylallyl)-1-azoniabicyclo[2.2.2]octane trifluoroacetate (3R)-3-[(2R)-2-Cyclopentyl-2-hydroxy-2-thien-2-ylacetoxy]-1-[3-(4-fluorophenoxy)propyl]-1-azoniabicyclo[2.2.2]octane trifluoroacetate (3R)-3-[(2S)-2-Cyclopentyl-2-fur-2-yl-2-hydroxyacetoxy]-1-(3-phenoxypropyl)-1-azoniabicyclo[2.2.2]octane trifluoroacetate (3R)-3-[(2S)-2-Cyclopentyl-2-fur-2-yl-2-hydroxyacetoxy]-1-(3-thien-2-ylpropyl)-1-azoniabicyclo[2.2.2]octane trifluoroacetate (3R)-3-[(2)-2-Cyclopentyl-2-fur-2-yl-2-hydroxyacetoxy]-1-phenethyl-1-azoniabicyclo[2.2.2]octane trifluoroacetate (3R)-3-[(2)-2-Cyclopentyl-2-fur-2-yl-2-hydroxyacetoxy]-1-(3-phenylpropyl)-1-azoniabicyclo[2.2.2]octane trifluoroacetate (3R)-3-[(2R)-2-Cyclopentyl-2-fur-2-yl-2-hydroxyacetoxy]-1-(3-phenoxypropyl)-1-azoniabicyclo[2.2.2]octane trifluoroacetate (3R)-3-[(2R)-2-Cyclopentyl-2-fur-2-yl-2-hydroxyacetoxy]-1-(3-thien-2-ylpropyl)-1-azoniabicyclo[2.2.2]octane trifluoroacetate (3R)-3-[(2R)-2-Cyclopentyl-2-fur-2-yl-2-hydroxyacetoxy]-1-phenethyl-1-azoniabicyclo[2.2.2]octane trifluoroacetate (3R)-3-[(2R)-2-Cyclopentyl-2-fur-2-yl-2-hydroxyacetoxy]-1-(3-phenylpropyl)-1-azoniabicyclo[2.2.2]octane trifluoroacetate (3R)-3-[(2R)-2-Cyclohexyl-2-hydroxy-2-phenylacetoxy]-1-(3-phenoxypropyl)-1-azoniabicyclo[2.2.2]octane trifluoroacetate (3R)-3-[(2R)-2-Cyclohexyl-2-hydroxy-2-phenylacetoxy]-1-(3-thien-2-ylpropyl)-1-azoniabicyclo[2.2.2]octane trifluoroacetate (3R)-3-[(2R)-2-Cyclohexyl-2-hydroxy-2-phenylacetoxy]-1-phenethyl-1-azoniabicyclo[2.2.2]octane trifluoroacetate (3R)-3-[(2S)-2-Cyclohexyl-2-hydroxy-2-phenylacetoxy]-1-(3-phenoxypropyl)-1-azoniabicyclo[2.2.2]octane trifluoroacetate (3R)-3-[(2S)-2-Cyclohexyl-2-hydroxy-2-phenylacetoxy]-1-(3-thien-2-ylpropyl)-1-azoniabicyclo[2.2.2]octane trifluoroacetate (3R)-3-[(2S)-2-Cyclohexyl-2-hydroxy-2-phenylacetoxy]-1-phenethyl-1-azoniabicyclo[2.2.2]octane trifluoroacetate (3R)-3-[(2S)-2-Cyclohexyl-fur-2-yl-2-hydroxyacetoxy]-1-(3-phenoxypropyl)-1-azoniabicyclo[2.2.2]octane trifluoroacetate (3R)-3-[(2S)-2-Cyclohexyl-fur-2-yl-2-hydroxyacetoxy]-1-(3-thien-2-ylpropyl)-1-azoniabicyclo[2.2.2]octane trifluoroacetate (3R)-3-[(2S)-2-Cyclohexyl-fur-2-yl-2-hydroxyacetoxy]-1-phenethyl-1-azoniabicyclo[2.2.2]octane trifluoroacetate (3R)-3-[(2S)-2-Cyclohexyl-fur-2-yl-2-hydroxyacetoxy]-1-(3-phenylpropyl)-1-azoniabicyclo[2.2.2]octane trifluoroacetate (3R)-3-[(2R)-2-Cyclohexyl-fur-2-yl-2-hydroxyacetoxy]-1-(3-phenoxypropyl)-1-azoniabicyclo[2.2.2]octane trifluoroacetate (3R)-3-[(2R)-2-Cyclohexyl-fur-2-yl-2-hydroxyacetoxy]-1-(3-thien-2-ylpropyl)-1-azoniabicyclo[2.2.2]octane trifluoroacetate (3R)-3-[(2R)-2-Cyclohexyl-fur-2-yl-2-hydroxyacetoxy]-1-phenethyl-1-azoniabicyclo[2.2.2]octane trifluoroacetate (3R)-3-[(2R)-2-Cyclohexyl-fur-2-yl-2-hydroxyacetoxy]-1-(3-phenylpropyl)-1-azoniabicyclo[2.2.2]octane trifluoroacetate (3R)-3-[(2R)-2-Cyclopentyl-2-hydroxy-2-phenylacetoxy]-1-(3-phenoxypropyl)-1-azoniabicyclo[2.2.2]octane trifluoroacetate (3R)-3-[(2R)-2-Cyclopentyl-2-hydroxy-2-phenylacetoxy]-1-phenethyl-1-azoniabicyclo[2.2.2]octane trifluoroacetate (3R)-3-[(2R)-2-Cyclopentyl-2-hydroxy-2-phenylacetoxy]-1-(3-phenylsulfanylpropyl)-1-azoniabicyclo[2.2.2]octane trifluoroacetate (3R)-3-[(2S)-2-Cyclopentyl-2-hydroxy-2-phenylacetoxy]-1-(3-phenoxypropyl)-1-azoniabicyclo[2.2.2]octane trifluoroacetate (3R)-3-[(2S)-2-Cyclopentyl-2-hydroxy-2-phenylacetoxy]-1-phenethyl-1-azoniabicyclo[2.2.2]octane trifluoroacetate (3R)-3-[(2S)-2-Cyclopentyl-2-hydroxy-2-phenylacetoxy]-1-(3-phenylsulfanylpropyl)-1-azoniabicyclo[2.2.2]octane trifluoroacetate (3R)-3-[(2S)-2-Cyclohexyl-2-hydroxy-2-thien-2-ylacetoxy]-1-(3-phenoxypropyl)-1-azoniabicyclo[2.2.2]octane trifluoroacetate (3R)-3-[(2S)-2-Cyclohexyl-2-hydroxy-2-thien-2-ylacetoxy]-1-phenethyl-1-azoniabicyclo[2.2.2]octane trifluoroacetate 1-[3-(3-Cyanophenoxy)propyl]-(3R)-3-[(2S)-2-cyclohexyl-2-hydroxy-2-thien-2-ylacetoxy]-1-azoniabicyclo[2.2.2]octane trifluoroacetate (3R)-3-[(2R)-2-Cyclohexyl-2-hydroxy-2-thien-2-ylacetoxy]-1-(3-phenoxypropyl)-1-azoniabicyclo[2.2.2]octane trifluoroacetate (3R)-3-[(2R)-2-Cyclohexyl-2-hydroxy-2-thien-2-ylacetoxy]-1-phenethyl-1-azoniabicyclo[2.2.2]octane trifluoroacetate 1-[3-(3-Cyanophenoxy)propyl]-(3R)-3-[(2R)-2-cyclohexyl-2-hydroxy-2-thien-2-ylacetoxy]-1-azoniabicyclo[2.2.2]octane trifluoroacetate (3R)-3-(2-Hydroxy-4-phenyl-2-thien-2-ylbutanoyloxy)-1-(3-phenoxypropyl)-1-azoniabicyclo[2.2.2]octane trifluoroacetate (3S)-3-[(2S)-2-Cyclopentyl-2-hydroxy-2-thien-2-ylacetoxy]-1-(3-phenoxypropyl)-1-azoniabicyclo[2.2.2]octane bromide (3S)-3-[(2S)-2-Cyclopentyl-2-hydroxy-2-thien-2-ylacetoxy]-1-(3-thien-2-ylpropyl)-1-azoniabicyclo[2.2.2]octane trifluoroacetate (3S)-3-[(2S)-2-Cyclopentyl-2-hydroxy-2-thien-2-ylacetoxy]-1-(3-phenylpropyl)-1-azoniabicyclo[2.2.2]octane trifluoroacetate 4-[(2R)-2-Cyclohexyl-2-hydroxy-2-phenylacetoxy]-1-(3-thien-2-ylpropyl)-1-azoniabicyclo[2.2.2]octane trifluoroacetate 4-[(2R)-2-Cyclohexyl-2-hydroxy-2-phenylacetoxy]-1-(3-phenoxypropyl)-1-azoniabicyclo[2.2.2]octane trifluoroacetate ((*): Configuration not assigned; either the (2R)- or the (2S)-isomers of the above compounds may be produced).

The present invention also provides processes for preparing compounds of formula (I). The quaternary ammonium derivatives of general formula (I), may be prepared by reaction of an alkylating agent of general formula (II) with compounds of general formula (III). In formulae (I), (II) and (III), $R^1$, $R^2$, $R^3$, B, A, $X^-$, $R^4$, $R^5$, $R^6$, n, m and p are as defined above.

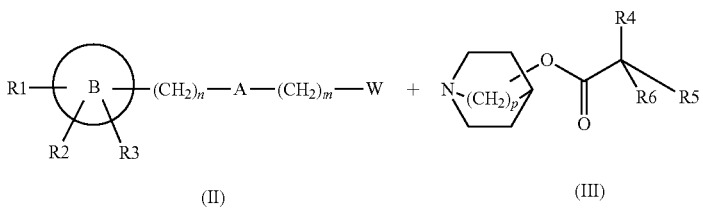

(II)　　(III)

Methods a), b)

-continued

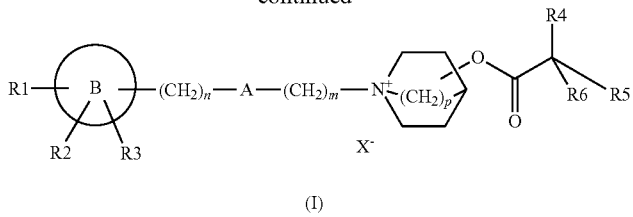

(I)

In formula (II), W represents any suitable leaving group, such as a group X as defined above. Preferably, W represents a group X.

This alkylation reaction may be carried out by two different experimental procedures, a) and b) which are described above. In particular method b) provides a new experimental process, using solid phase extraction methodologies, that allows the parallel preparation of several compounds. Methods a) and b) are described in the experimental section. If W represents a group other than X, the quaternary ammonium salt of formula (I) is produced from the product of method (a) or (b) by carrying out an exchange reaction according to standard methods to replace the anion W⁻ with the desired anion X⁻.

Compounds of general formula (II) which are not commercially available have been prepared by synthesis according to standard methods. For example, compounds wherein n=0 and A=—O—, —S— or —NR⁹—, wherein R⁹ is as defined above, were obtained by reaction of the corresponding aromatic derivative or its potassium salt with an alkylating agent of general formula Y—(CH$_2$)m-X, wherein X may be a halogen and Y may be a halogen or a sulphonate ester. In other examples, compounds of general formula (II), where n≧1 were synthesised from the corresponding alcohol derivative of general formula (IV) by known methods

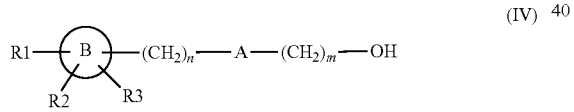

(IV)

wherein R¹, R², R³, n, m, and A are as defined above.

Compounds of general formula (III) may be prepared by different methods. These procedures are illustrated in the following schemes and detailed in the experimental section.

Method C)

Compounds of general formula (III) may be synthesised by transesterification of a compound of formula (V) with a compound of formula (VI).

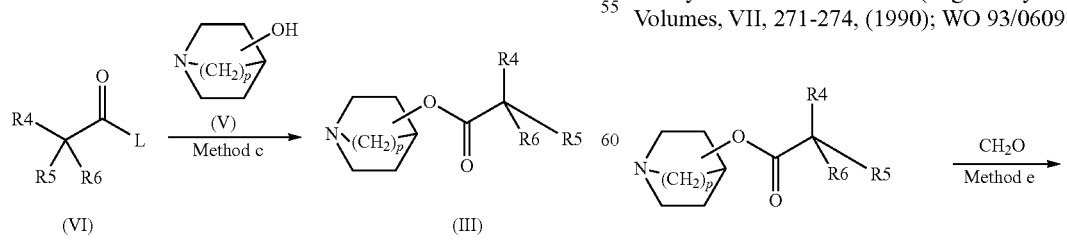

in which formulae R⁴, R⁵, R⁶ and p are as defined above and L represents a leaving group. For example L may be a chlorine atom, an imidazol-1-yl group, or a group —OR¹⁴ wherein R¹⁴ represents a straight or branched, substituted or unsubstituted lower alkyl group or a —COR¹⁵ group wherein R¹⁵ represents —COCR⁴R⁵R⁶. Typically L is —OR¹⁴ wherein R¹⁴ is methyl, ethyl or propyl, or L is an imidazol-1-yl group. Intermediates of formula (VI) may be prepared by standard methods described in the literature, for example as in FR 2012964.

Method D)

Compounds of formula (III) where R⁶ is a hydroxy group and p, R⁴ and R⁵ are as described above, may also be prepared from the glyoxalate esters of general formula (VII) by reaction with the corresponding Grignard reagent.

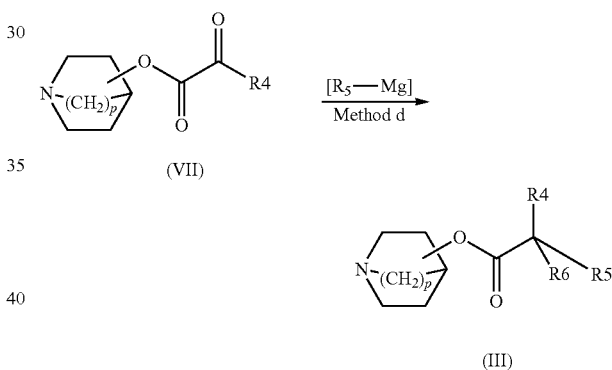

Compounds of general formula (VII) may be prepared by standard methods described in the literature (WO 01/04118; WO 92/04346)

Method E)

Compounds of formula (III) where R⁶ is a group —CH$_2$OH, and p, R⁴ and R⁵ are as described above, may also be prepared from the corresponding compound of formula (III), where R⁶ is an hydrogen atom, by reaction with formaldehyde in basic conditions. (Organic Syntheses Collective Volumes, VII, 271-274, (1990); WO 93/06098)

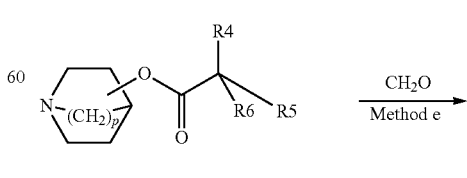

R6 = H

-continued

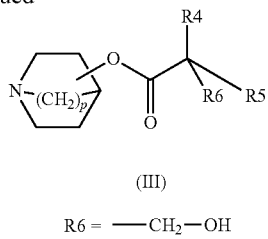

(III)

R6 = —CH$_2$—OH

As will be described in the experimental part, the diastereomers of the compounds of formula (III) may be separated by conventional methods, for example by column chromatography or crystallisation.

The following compounds are compounds of general formula (III) which have not been described before: compounds of formula (III)

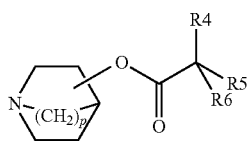

(III)

wherein p, R4, R5 and R6 are as defined above, the substituent on the azabicyclo group is at position 3 or 4 and when it is at position 3 this substituted carbon has an enantiomerically pure R or S configuration, provided that when R4 is a 3-thienyl group and R5 is a cyclohexyl group R6 is not a hydroxy group.

The substituent on the azabicyclo group is preferably at position 3 and may have R or S configuration. The carbon substituted by R$^4$, R$^5$ and R$^6$ may have R or S configuration. The compound may be a single isomer.

Examples of the new compounds of formula (III) include:
(2S)-2-Cyclopentyl-2-fur-2-yl-2-hydroxyacetic acid (3R)-1-azabicyclo[2.2.2]oct-3-yl ester ($[\alpha]^{22}_D$=+19.7° (c=1, CHCl$_3$)).
(2R)-2-Cyclopentyl-2-fur-2-yl-2-hydroxyacetic acid (3R)-1-azabicyclo[2.2.2]oct-3-yl ester ($[\alpha]^{22}_D$=−14.2° (c=1, CHCl$_3$)).
(2S)-2-Cyclohexyl-2-fur-2-yl-2-hydroxyacetic acid (3R)-1-azabicyclo[2.2.2]oct-3-yl ester ($[\alpha]^{22}_D$=+21.1° (c=1, CHCl$_3$)).
(2R)-2-Cyclohexyl-2-fur-2-yl-2-hydroxyacetic acid (3R)-1-azabicyclo[2.2.2]oct-3-yl ester ($[\alpha]^{22}_D$=−23.5° (c=1, CHCl$_3$)).
(2R)-2-Cyclohexyl-2-hydroxy-2-phenylacetic acid 1-azabicyclo[2.2.2]oct-4-yl ester ($[\alpha]^{22}_D$=−27.6° (c=1, CHCl$_3$)).
In particular:
(2S)-2-Cyclopentyl-2-fur-2-yl-2-hydroxyacetic acid (3R)-1-azabicyclo[2.2.2]oct-3-yl ester ($[\alpha]^{22}_D$=+19.7° (c=1, CHCl$_3$)).
(2R)-2-Cyclopentyl-2-fur-2-yl-2-hydroxyacetic acid (3R)-1-azabicyclo[2.2.2]oct-3-yl ester ($[\alpha]^{22}_D$=−14.2° (c=1, CHCl$_3$)).
(2S)-2-Cyclohexyl-2-fur-2-yl-2-hydroxyacetic acid (3R)-1-azabicyclo[2.2.2]oct-3-yl ester ($[\alpha]^{22}_D$=+21.1° (c=1, CHCl$_3$)).
(2R)-2-Cyclohexyl-2-fur-2-yl-2-hydroxyacetic acid (3R)-1-azabicyclo[2.2.2]oct-3-yl ester ($[\alpha]^{22}_D$=−23.5° (c=1, CHCl$_3$)).

Compounds of Formula (V) Could Be:
4-hydroxy-1-azabicyclo[2.2.1]heptane, described in WO93/15080
4-hydroxy-1-azabicyclo[2.2.2]octane, described in Grob, C. A. et. al. Helv. Chim. Acta (1958), 41, 1184-1190
(3R)-3-hydroxy-1-azabicyclo[2.2.2]octane or (3S)-3-hydroxy-1-azabicyclo[2.2.2]octane, described in Ringdahl, R. Acta Pharm Suec. (1979), 16, 281-283 and commercially available from CU Chemie Uetikon GmbH.

The following examples are intended to illustrate, but not to limit, the experimental procedures that have been described above.

The structures of the prepared compounds were confirmed by $^1$H-NMR and MS. The NMR spectra were recorded using a Varian 300 MHz instrument and chemical shifts are expressed as parts per million (δ) from the internal reference tetramethylsilane. Their purity was determined by HPLC, using reverse phase chromatography on a Waters instrument, with values greater than 95% being obtained. Molecular ions were obtained by electrospray ionization mass spectrometry on a Hewlett Packard instrument. Optical rotations were obtained using a PERKIN-ELMER 241 MC Polarimeter.

Method—a—

EXAMPLE 13

Preparation of (3R)-3-(2-Hydroxy-2-thien-2-ylpent-4-enoyloxy)-1-(3-phenoxypropyl)-1-azoniabicyclo[2.2.2]octane bromide 250 mg (0.81 mmol) of 2-Hydroxy-2-thien-2-ylpent-4-enoic acid (3R)-1-azabicyclo[2.2.2]oct-3-yl ester, Intermediate I-3, were dissolved in 5 ml of acetonitrile and 7.5 ml of chloroform. To this solution were added 0.63 ml (4.1 mmol) of phenoxypropylbromide. After stirring for 48 h at room temperature under a N$_2$ atmosphere, solvents were evaporated. Ether was added and the mixture stirred. The solid obtained was filtered and washed several times with ether. The yield was 0.3 g (71%) of the title compound as a mixture of diastereomers; mp: 157° C.

$^1$H-NMR (DMSO-d$_6$): δ 1.70-2.05 (m, 4H), 2.05-2.35 (m, 3H), 2.70-2.83 (m, 1H), 2.90-3.02 (m, 1H), 3.25-3.60 (m, 7H), 3.82-3.97 (m, 1H); 3.97-4.10 (m, 2H), 5.05-5.25 (m, 3H), 5.70-5.90 (m, 1H), 6.50 (d, 1H, OH), 6.90-7.05 (m, 4H), 7.10-7.20 (m, 1H), 7.27-7.35 (m, 2H), 7.45 (m, 1H).

MS: [M-Br]$^+$: 442.

Method—b—

EXAMPLE 35

Preparation of (3R)-3-[(2S)-2-Cyclopentyl-2-hydroxy-2-thien-2-ylacetoxy]-1-[3-(naphthalen-1-yloxy)propyl]-1-azoniabicyclo[2.2.2]octane trifluoroacetate 20 mg (0.06 mmols) of (2S)-2-Cyclopentyl-2-hydroxy-2-thien-2-ylacetic acid (3R)-1-azabicyclo[2.2.2]oct-3-yl ester (Intermediate I-15a), were dissolved in 1 ml of DMSO. To this solution 66 mg (0.30 mmol) of 3-(naphthalen-1-yloxy) propyl chloride were added. After stirring overnight at room temperature, the mixture was purified by solid phase extraction with a cation exchange Mega Bond Elut cartridge, previously conditioned at pH=7.5 with 0.1 M NaH$_2$PO4 buffer. The reaction mixture was applied to the cartridge and washed first with 2 ml of DMSO and then three times with 5 ml of CH$_3$CN, rinsing away all starting materials. The ammonium derivative was eluted with 5 ml of 0.03 M TFA solution in CH$_3$CN:CHCl$_3$ (2:1). This solution was neutralized with 300 mg of poly(4-vinylpyridine), filtered and evaporated to dryness. The yield was 10 mg (26%) of title compound.

$^1$H-NMR (DMSO-d$_6$): δ 1.30-1.65 (m, 8H), 1.80-2.10 (m, 4H), 2.20-2.37 (m, 3H), 2.75-2.92 (m, 1H), 3.20-3.65 (m, 7H), 3.90-4.05 (m, 1H), 4.15-4.30 (m, 2H), 5.15-5.22 (m,

1H), 6.24 (s, 1H, OH), 6.95-7.05 (m, 2H), 7.15-7.20 (m, 1H), 7.40-7.60 (m, 5H), 7.85-7.95 (m, 1H), 8.20-8.25 (m, 1H).

MS: [M-CF$_3$COO]$^+$: 520

The spatial configurations of the compounds of general formula (III) have been deduced from the configurations of their corresponding acids. These were determined either comparing the values of [α] obtained with the values described in the literature or applying the Circular Dichroism (CD) technique.

Since the CD curve of (2S)-2-Cyclohexyl-2-hydroxy-2-phenylacetic acid is known (A. Tambuté and A. Collet, Bulletin de la Société Chimique de France, 1984, N° 1-2, pages II77 to II82) and all the acids evaluated are structurally very similar to (2S)-2-Cyclohexyl-2-hydroxy-2-phenylacetic acid, it can be assumed that the relative positions of the aryl, cycloalkyl, carboxyl and hydroxyl substituents may be identified by comparison of their respective Δε values. The resulting configurations have been expressed as R or S according to Cahn-Ingol-Prelog system. (see TABLE 1)

The curves of CD spectra were recorded with a Jasco-720 spectrophotometer (Software J-700) from 0.43 mM MeOH solutions of the samples in 1 mm cells at 25° C.

with replacement with fresh toluene when necessary for 1 hour. The cooled mixture was extracted with 1N HCl acid, the aqueous layer washed with ether, basified with K$_2$CO$_3$ and extracted with CHCl$_3$. The organic layer was washed with water, dried over MgSO$_4$ and evaporated. The yield was 2.85 g (76%) of the title product as a mixture of diastereomers, structure confirmed by $^1$H-NMR.

$^1$H-NMR (CDCl$_3$): δ 0.80-0.95 (m, 3H), 1.20-1.40 (m, 6H), 1.40-1.90 (m, 4H), 1.95-2.25 (m, 3H), 2.50-2.95 (m, 5H), 3.10-3.30 (m, 1H), 4.4 (bs, 1H, OH), 4.82-4.94 (m, 1H), 6.94-7.02 (m, 1H), 7.06-7.14 (m, 1H), 7.20-7.26 (m, 1H).

MS: [M+1]$^+$: 338.

(Compound also prepared following method d)

Intermediate I-2

Preparation of 2,3-Diphenylpropionic acid (3R)-1-azabicyclo[2.2.2]oct-3-yl ester Prepared using the same method as for Intermediate I-1, but from 2,3-diphenylpropionic acid methyl ester. The yield was 1.71 g (61.5%) of the title product as a mixture of diastereomers.

TABLE 1

| Compound | [α]$^{22}_D$ | Circular Dichroism | | Configuration |
|---|---|---|---|---|
| | | λ (nm) | Δε (M$^{-1}$cm$^{-1}$) | |
| (+)-2-Cyclohexyl-2-hydroxy-2-phenylacetic acid | +23.1° (c = 1.4, EtOH) | 224 | +12.1 | S[a] |
| (−)-2-Cyclohexyl-2-hydroxy-2-phenylacetic acid | −23.6° (c = 1.4, EtOH) | 224 | −11.7 | R |
| (−)-2-Cyclopentyl-2-hydroxy-2-phenylacetic acid | −1.52° (c = 3, MeOH) | 224 | −8.93 | R[b] |
| (+)-2-Cyclopentyl-2-hydroxy-2-thien-2-ylacetic acid[c,1] | +6.63° (c = 1, EtOH) | 233 | +4.18 | R |
| (−)-2-Cyclopentyl-2-hydroxy-2-thien-2-ylacetic acid[c,2] | −6.44° (c = 1, EtOH) | 233 | −4.19 | S |
| (−)-2-Cyclohexyl-2-hydroxy-2-thien-2-ylacetic acid[c,3] | −15.1° (c = 1, EtOH) | 235 | −5.40 | S |
| (+)-2-Cyclopentyl-2-fur-2-yl-2-hydroxyacetic acid | +31.95° (c = 1, EtOH) | 230 | +7.64 | S |
| (−)-2-Cyclopentyl-2-fur-2-yl-2-hydroxyacetic acid | −32.10° (c = 1, EtOH) | 230 | −7.44 | R |
| (+)-2-Cyclohexyl-2-fur-2-yl-2-hydroxyacetic acid | +4.90° (c = 1, EtOH) | 230 | +10.9 | S |
| (−)-2-Cyclohexyl-2-fur-2-yl-2-hydroxyacetic acid | −39.7° (c = 1, EtOH) | 230 | −10.8 | R |

[a] A. Tambuté et A. Collet; Bulletin de la Societé Chimique de France, (1984), N°1-2, II-77-II-82: Configuration S assigned: [α]$^{24}_D$ = +25.2° (c = 1.4, EtOH), Δε = +12.9 M$^{-1}$cm$^{-1}$ (λ = 225 nm)
[b] M. Mitsuya et al.; Bioorg. Med. Chem., (1999), Vol 7, 2555–2567: Configuration R assigned [α]$^{20}_D$ = −1.9° (c = 3, MeOH)
[c] E. Atkinson et al. J. Med. Chem., (1977), Vol 20, N° 12, 1612–1617. The values for [α] were given (Configuration not assigned); c, 1 and c, 2: +51.3° and −51.0° (rotations observed at 350 nm (c = 2–5%, MeOH)).

Method—c—

Methyl ester derivatives of general formula (VI) were prepared by standard methods described in the literature or following the procedures described in the examples: Intermediates I-9, I-10, I-11, I-12, I-13.

Intermediate I-1

Preparation of 2-Hydroxy-2-thien-2-ylheptanoic acid (3R)-1-azabicyclo[2.2.2]oct-3-yl ester 2.7 g of 2-Hydroxy-2-thien-2-ylheptanoic acid methyl ester (Intermediate I-9) (0.011 mol) were dissolved in 70 ml of toluene. To this solution were added 1.63 g (0.0128 mol) of (3R)-3-hydroxy-1-azabicyclo[2.2.2]octane and 0.18 g (0.0045 mol) of HNa (60% dispersion in mineral oil). The mixture was refluxed with continuous removal of distillate $^1$H-NMR (DMSO): δ 1.05-1.20 (m, 1H), 1.30-1.60 (m, 3H), 1.65-1.75 (m, 1H), 2.10-2.20 (m, 1H), 2.30-2.70 (m, 4H), 2.85-3.10 (m, 2H), 3.20-3.40 (m, 1H), 3.95-4.10 (m, 1H), 4.50-4.65 (m, 1H), 7.10-7.45 (m, 10H).

MS: [M+1]$^+$: 336

(2,3-diphenylpropionic acid methyl ester may be prepared from the 2,3-diphenylpropionic acid, commercially available)

Intermediate I-3

Preparation of 2-Hydroxy-2-thien-2-ylpent-4-enoic acid (3R)-1-azabicyclo[2.2.2]oct-3-yl ester Prepared using the same method as for Intermediate I-1, but from 2-Hydroxy-2-thien-2-ylpent-4-enoic acid methyl ester (Intermediate I-10). The yield was 1.76 g (63.1%) of the title product as a mixture of diastereomers.

$^1$H-NMR (CDCl$_3$): δ 1.25-1.80 (m, 4H), 1.80-2.10 (m, 1H), 2.50-3.05 (m, 7H), 3.10-3.35 (m, 2H), 4.55 (bs, 1H, OH), 4.75-4.95 (m, 1H), 5.10-5.30 (m, 2H), 5.70-5.95 (m, 1H), 6.95-7.05 (m, 1H), 7.10-7.20 (m, 1H), 7.20-7.30 (m, 1H).

MS: [M+1]$^+$: 308

(Compound also prepared following method d)

Intermediate I-4

Preparation of 2-Cyclohexyl-2-fur-2-yl-2-hydroxyacetic acid (3R)-1-azabicyclo[2.2.2]oct-3-yl ester Prepared using the same method as for Intermediate I-1, but from 13.73 g (0.057 mol) of 2-Cyclohexyl-2-fur-2-yl-2-hydroxyacetic acid methyl ester (Intermediate I-11) dissolved in 350 ml of toluene, 8.6 g (0.067 mol) of (3R)-3-hydroxy-1-azabicyclo[2.2.2]octane and 1.37 g (0.0342 mol) of HNa (60% dispersion in mineral oil). The oil obtained (10.33 g) was purified by chromatography on silica gel eluting with chloroform/methanol/ammonia 97:3:0.3. Appropiate fractions were combined and evaporated to obtain the two diastereomers: I-4a and I-4b.

Intermediate I-4a (2S)-2-Cyclohexyl-2-fur-2-yl-2-hydroxyacetic acid (3R)-1-azabicyclo[2.2.2]oct-3-yl ester 1.59 g of an oil corresponding to the first eluted diastereomer was triturated with a mixture of ethyl ether/isopropyl ether 1:1, to give 0.82 g (8.6%, based on single isomer) of a solid whose structure was confirmed by $^1$H-NMR as a pure diastereomer.

[α]$^{22}_D$=+21.1° (c=1, CHCl$_3$)).

$^1$H-NMR (CDCl$_3$): δ 1.10-1.45 (m, 8H), 1.45-1.60 (m, 2H), 1.60-1.85 (m, 4H), 1.94-2.02 (m, 1H), 2.26-2.38 (m, 1H), 2.70-2.92 (m, 5H), 3.20-3.28 (m, 1H), 3.78 (bs, 1H, OH), 4.90 (m, 1H), 6.30-6.40 (m, 2H), 7.40 (m, 1H).

MS: [M+1]$^+$: 334.

Intermediate I-4a was hydrolised (EtOH/NaOH 2N, 2 h r.t, 1 h 60° C.), to yield (+)-2-Cyclohexyl-2-fur-2-yl-2-hydroxyacetic acid: [α]$^{22}_D$=+40.9° (c=1, EtOH).

Configuration S was assigned (See TABLE 1)

Intermediate I-4b (2R)-2-Cyclohexyl-2-fur-2-yl-2-hydroxyacetic acid (3R)-1-azabicyclo[2.2.2]oct-3-yl ester 1.12 g of an oil corresponding to the second eluted diastereomer was triturated with a mixture of ethyl ether/isopropyl ether 1:1, to give 0.57 g (6%, based on single isomer) of a solid whose structure was confirmed by $^1$H-NMR as a pure diastereomer.

[α]$^{22}_D$=−23.5° (c=1, CHCl$_3$)).

$^1$H-NMR (CDCl$_3$): δ 1.10-1.50 (m, 8H), 1.50-1.90 (m, 6H), 2.04-2.12 (m, 1H), 2.24-2.36 (m, 1H), 2.46-2.58 (m, 1H), 2.68-2.94 (m, 4H), 3.12-3.22 (m, 1H), 3.77 (bs, 1H, OH), 4.90 (m, 1H), 6.40 (m, 2H), 7.42 (m, 1H)

MS: [M+1]$^+$: 334.

Intermediate I-4b was hydrolised (EtOH/NaOH 2N, 2 h r.t, 1 h 60° C.), to yield (−)-2-Cyclohexyl-2-fur-2-yl-2-hydroxyacetic acid: [α]$^{22}_D$=−39.7° (c=1, EtOH).

Configuration R was assigned. (See TABLE 1)

Intermediate I-5

Preparation of 2-Cyclopentyl-2-hydroxy-2-phenylacetic acid (3R)-1-azabicyclo[2.2.2]oct-3-yl ester Prepared using the same method as for Intermediate I-1, but from 13.5 g (0.0576 mol) of 2-Cyclopentyl-2-hydroxy-2-phenylacetic acid methyl ester (commercially available) dissolved in 350 ml of toluene, 8.0 g (0.063 mol) of (3R)-3-hydroxy-1-azabicyclo[2.2.2]octane and 0.91 g (0.023 mol) of HNa (60% dispersion in mineral oil). The yield was 13.1 g (69%) of the title product as an oil mixture of diastereomers, structure confirmed by $^1$H-NMR; The two diastereomers I-5a and I-5b were separated after several crystallizations.

Intermediate I-5a (2R)-2-Cyclopentyl-2-hydroxy-2-phenylacetic acid (3R)-1-azabicyclo[2.2.2]oct-3-yl ester Several treatments of the oil mixture of diastereomers with different mixtures of diethyl ether/hexane and diisopropyl ether/hexane (cooling at −60° C.) yield 4.3 g of a white solid identified by $^1$H-RMN as an enriched diastereomer I-5a. This solid was recrystallised twice from diethyl ether/hexane (cooling at 0° C.) to yield 2 g (21%) of pure diastereomer.

[α]$^{22}_D$=−10.8° (c=1, CHCl$_3$)

$^1$H-NMR (CDCl$_3$): δ 1.25-1.80 (m, 11H), 1.80-1.95 (m, 1H), 2.05-2.15 (m, 1H), 2.40-2.50 (m, 1H), 2.62-3.05 (m, 5H), 3.05-3.18 (m, 1H), 3.80 (s, 1H, OH), 4.85-4.90 (m, 1H), 7.22-7.42 (m, 3H), 7.60-7.75 (m, 2H).

Intermediate I-5a was hydrolised (EtOH/NaOH 2N, 2 h r.t. and 2 h at 60° C.) to give (−)-2-Cyclopentyl-2-hydroxy-2-phenylacetic acid as a pure enantiomer: [α]$^{22}_D$=−1.52° (c=3, MeOH). This value was assigned to the R configuration provided that in the literature (M. Mitsuya et al.; Bioorg. Med. Chem., (1999), 7, 2555-2567) the R enantiomer has been described with [α]$^{20}_D$=−1.9° (c=3, MeOH). (See TABLE 1)

Intermediate I-5b (2S)-2-Cyclopentyl-2-hydroxy-2-phenylacetic acid (3R)-1-azabicyclo[2.2.2]oct-3-yl ester The mother liquors from the first solid I-5a were evaporated and treated with maleic acid in isopropanol/diethyl ether. After cooling at 0-5° C., 7.0 g of a white solid were obtained and identified by $^1$H-RMN as the maleate salt of a mixture enriched with the second diastereomer I-5b. After three crystallisations of this product from acetonitrile/diethyl ether (1:2.2), 2.4 g (18.7%, based on free base) of the maleate salt enriched with the second diastereomer I-5b (in a proportion 88:12 as determined by H-RMN) were obtained.

This maleate salt enriched with the second diastereomer I-5b (88:12) was treated with CHCl$_3$ and K$_2$CO$_3$ solution to obtain the free base.

I-5b (free base):

[α]$^{22}_D$=+19.5° (c=1, CHCl$_3$)

$^1$H-NMR (CDCl$_3$): δ 1.20-1.80 (m, 12H), 1.85-2.0 (m, 1H), 2.60-3.05 (m, 6H), 3.20-3.35 (m, 1H), 3.80 (s, 1H, OH), 4.75-4.82 (m, 1H), 7.20-7.45 (m, 3H), 7.55-7.75 (m, 2H). The signals corresponding to the diastereomer I-5a (12%) were observed at 2.05-2.15, 2.40-2.50, 3.05-3.18, 4.85-4.90 ppm.

Configuration S was assigned in view of the results obtained for Intermediate I-5a. (See TABLE 1).

Intermediate I-6

Preparation of 2-Cyclohexyl-2-hydroxy-2-thien-2-ylacetic acid (3R)-1-azabicyclo[2.2.2]oct-3-yl ester Prepared using the same method as for Intermediate I-1, but from 16.2 g (0.064 mol) of 2-Cyclohexyl-2-hydroxy-2-thien-2-ylacetic acid methyl ester (Intermediate I-12), dissolved in 400 ml of toluene, 9.5 g (0.074 mol) of (3R)-3-hydroxy-1-azabicyclo[2.2.2]octane and 1.51 g (0.038 mol) of HNa (60% dispersion in mineral oil). The oil obtained (10.97 g) was purified by chromatography on silica gel, eluting with chloroform/methanol/ammonia 95:5:0.5, to obtain 8.97 g of a pure product as a mixture of diastereomers, structure confirmed by $^1$H-RMN. Three crystallisations of this mixture from ethyl ether yield 1.68 g (15.2%) of a pure diastereomer (Intermediate I-6a). The mother liquors of the crystallisations were enriched with the other diastereomer (Intermediate I-6b).

Intermediate I-6a (2S)-2-Cyclohexyl-2-hydroxy-2-thien-2-ylacetic acid (3R)-1-azabicyclo[2.2.2]oct-3-yl ester $[\alpha]^{22}_D = -16.5°$ (c=1, CHCl$_3$).
$^1$H-NMR (CDCl$_3$): δ 1.05-1.85 (m, 13H), 1.85-2.0 (m, 1H), 2.0-2.16 (m, 2H), 2.58-2.68 (m, 1H), 2.70-3.0 (m, 4H), 3.14-3.24 (m, 1H), 4.0 (s, 1H, OH), 4.90-5.0 (m, 1H), 6.95-7.05 (m, 1H), 7.10-7.15 (m, 1H), 7.20-7.30 (m, 1H).
MS: [M+1]$^+$: 350.
Intermediate I-6a was hydrolised (EtOH/NaOH 2N, 2 h r.t, 1 h 60° C.), to yield (−)-2-Cyclohexyl-2-hydroxy-2-thien-2-ylacetic acid: $[\alpha]^{22}_D = -15.1°$ (c=1, EtOH).
Configuration S was assigned. (See TABLE 1).

Intermediate I-6b (2R)-2-Cyclohexyl-2-hydroxy-2-thien-2-ylacetic acid (3R)-1-azabicyclo[2.2.2]oct-3(R)-yl ester $^1$H-NMR (CDCl$_3$): δ 1.05-2.0 (m, 14H), 2.0-2.20 (m, 2H), 2.65-3.02 (m, 5H), 3.24-3.36 (m, 1H), 4.0 (s, 1H, OH), 4.80-4.90 (m, 1H), 6.95-7.05 (m, 1H), 7.10-7.20 (m, 1H), 7.20-7.30 (m, 1H).
The signals corresponding to the Intermediate I-6a (aprox. 25%) were observed at 2.58-2.68, 3.14-3.24 and 4.90-5.0 ppm.
MS: [M+1]$^+$: 350.
Configuration R was assigned in view of the results obtained with Intermediate I-6a. (See TABLE 1).

Intermediate I-7

(2S)-2-Cyclopentyl-2-hydroxy-2-thien-2-ylacetic acid (3S)-1-azabicyclo[2.2.2]oct-3-yl ester 510 mg (0.00225 mol) of (2S)-2-Cyclopentyl-2-hydroxy-2-thien-2-ylacetic acid (obtained by hydrolysis of Intermediate I-15a) were dissolved in 7 ml of DMF. This solution was stirred at room temperature and 638 mg (0.00393 mol) of 1,1'-carbonyldiimidazole were added in several portions. After 4.5 h the reaction mixture was cooled to 0° C. and 315 mg (0.00248 mol) of (3S)-3-hydroxy-1-azabicyclo[2.2.2]octane and 83 mg (0.0021 mol) of HNa (60% dispersion in mineral oil) were added thereto. After stirring 112 h at room temperature the reaction mixture was treated with water and extracted three times with diethyl ether. The organic layers were combined, washed with brine and dried over anhydrous magnesium sulfate. The solvent was evaporated and the residue was purified by silica gel column chromatography (eluent CHCl$_3$/MeOH 15:1) to obtain 360 mg (47.6%) of the title product as an oil, structure confirmed by $^1$H-RMN.

$[\alpha]^{22}_D = -18.16°$ (c=1, CHCl$_3$)
$^1$H-NMR (CDCl$_3$): δ (Same description as in Intermediate I-15b)
MS: [M+1]$^+$: 336.

Intermediate I-8

(2R)-2-Cyclohexyl-2-hydroxy-2-phenylacetic acid 1-azabicyclo[2.2.2]oct-4-yl ester Prepared using the same method as for Intermediate I-7, but from a solution of 660 mg (0.00282 mol) of (2R)-2-Cyclohexyl-2-hydroxy-2-phenylacetic acid (obtained by hydrolysis of Intermediate I-16a) in 9 ml of DMF, 548 mg (0.00338 mol) of 1,1'-carbonyldiimidazole, 394 mg (0.0031 mol) of 4-hydroxy-1-azabicyclo[2.2.2]octane and 104 mg (0.00259 mol) of HNa (60% dispersion in mineral oil). After 44 h of stirring at room temperature the reaction mixture was treated with water and extracted three times with diethyl ether. The organic layers were combined, washed with brine and dried over anhydrous magnesium sulfate. The solvent was evaporated and the residue was purified by silica gel column chromatography eluting with CHCl$_3$ to CHCl$_3$/MeOH 15:1. The yield was 300 mg (31%) of the title product.

$[\alpha]^{22}_D = -27.6°$ (c=1, CHCl$_3$)
$^1$H-NMR (CDCl$_3$): δ 1.0-1.55 (m, 7H), 1.55-1.75 (m, 2H), 1.75-1.85 (m, 1H), 1.85-2.05 (m, 6H), 2.10-2.22 (m, 1H), 2.90-3.10 (m, 6H), 3.60-3.80 (bs, 1H, OH), 7.20-7.40 (m, 3H), 7.57-7.67 (m, 2H).
MS: [M+1]$^+$: 344.

Intermediate I-9

Preparation of 2-Hydroxy-2-thien-2-ylheptanoic acid methyl ester 50 ml of a ether solution of 0.0338 mol of pentylmagnesium bromide prepared from 5.1 g of 1-bromopentane (0.0338 mol) and 0.0372 mols of magnesium, were added to a solution of 5 g of 2-oxo-2-thien-2-ylacetic acid methyl ester dissolved in 40 ml of a solution of ether/THF (50:50), at −70° C. under a N$_2$ atmosphere. The mixture was stirred at this temperature for 10 minutes, and then warmed to room temperature. After 16 h, the reaction mixture was treated with a saturated solution of ammonium chloride and extracted three times with ethyl acetate. The organic phases were combined, washed with water, and dried over MgSO$_4$. After removal of the solvent, the oil obtained was purified by column chromatography (silica gel) using mixtures of hexane/AcOEt (25:1 to 15:1) as eluent. The yield was 2.7 g (38%) of a pure product, whose structure was confirmed by $^1$H-NMR.

$^1$H-NMR (CDCl$_3$): δ 0.80-1.0 (m, 3H), 1.10-1.45 (m, 6H), 1.90-2.30 (m, 2H), 3.80 (s, 3H), 4.05 (s, 1H, OH), 7.0 (m, 1H), 7.10 (m, 1H), 7.30 (m, 1H).

(2-Oxo-2-thien-2-ylacetic acid methyl ester was prepared from the commercially available 2-oxo-2-thien-2-ylacetic acid by a standard method)

Intermediate I-10

Preparation of 2-Hydroxy-2-thien-2-ylpent-4-enoic acid methyl ester

Prepared using the same method as for Intermediate I-9. The yield was 1.92 g. 45.3%.
$^1$H-NMR (CDCl$_3$): δ 2.75-3.0 (m, 2H), 3.80 (s, 3H), 4.0 (s, 1H, OH), 5.10-5.30 (m, 2H), 5.70-5.90 (m, 1H), 6.95-7.05 (m, 1H), 7.10-7.20 (m, 1H), 7.25-7.35 (m, 1H).
MS: [M]$^+$=212.

Intermediate I-11

Preparation of 2-Cyclohexyl-2-fur-2-yl-2-hydroxyacetic acid methyl ester

Prepared using the same method as for Intermediate I-9, but from 73 ml (0.146 mol) of a solution of cyclohexylmagnesium chloride 2M in diethyl ether and 22.51 g (0.146 mol) of 2-fur-2-yl-2-oxoacetic acid methyl ester (dissolved in 330 ml of THF). The oil obtained was purified by column chromatography (silica gel) using a mixture of hexane/AcOEt 9:1 as eluent. After removal of the solvent 13.73 g (39%) of a pure product were obtained whose structure was confirmed by MS and $^1$H-NMR.
$^1$H-NMR (CDCl$_3$): δ 1.05-1.75 (m, 6H), 1.75-1.95 (m, 4H), 2.20-2.40 (m, 1H), 3.80 (s, 3H), 3.95 (s, 1H, OH), 6.30-6.50 (m, 2H), 7.35-7.45 (m, 1H).
MS: [M]$^+$: 238.

(2-Fur-2-yl-2-oxoacetic acid methyl ester was prepared from the commercially available 2-fur-2-yl-2-oxoacetic acid by a standard method).

Intermediate I-12

Preparation of 2-Cyclohexyl-2-hydroxy-2-thien-2-ylacetic acid methyl ester 98.6 ml (0.197 mol) of a 2M solution of Cyclohexylmagnesium chloride in diethyl ether, were added to a solution of 27.97 g (0.164 mol) of 2-oxo-2-thien-2-ylacetic acid methyl ester dissolved in 370 ml of THF, at −78° C. under a N2 atmosphere. The mixture was stirred at this temperature for 10 minutes, and then warmed to room temperature. After 1 h, the reaction mixture was treated with a saturated solution of ammonium chloride and extracted three times with ethyl acetate. The organic phases were combined, washed with water, and dried over MgSO$_4$. After removal of the solvent, the oil obtained was purified by column chromatography (silica gel) using hexane/AcOEt 90:10 as eluent. The yield was 16.2 g (39.5%) of a pure product, whose structure was confirmed by $^1$H-NMR.
$^1$H-NMR (CDCl$_3$): δ 1.0-1.55 (m, 6H), 1.55-1.90 (m, 4H), 2.0-2.20 (m, 1H), 3.80 (s, 3H), 4.0 (s, 1H, OH), 7.0 (m, 1H), 7.10 (m, 1H), 7.20-7.30 (m, 1H).
MS: [M$^+$]: 254.

(Intermediate I-12 is described in E. Atkinson et al. J. Med. Chem., (1977), Vol 20, N° 12, 1612-1617)

Intermediate I-13

Preparation of 2-Cyclopentyl-2-hydroxy-2-thien-2-ylacetic acid methyl ester

Prepared as in Example I-12. The yield was 3.83 g (37%).
$^1$H-NMR (CDCl$_3$): δ 1.35-1.75 (m, 8H), 2.70-2.90 (m, 1H), 3.80 (s, 3H), 4.02 (s, 1H, OH), 6.95-7.05 (m, 1H), 7.10-7.20 (m, 1H), 7.20-7.25 (m, 1H).
(Intermediate I-13 is described in E. Atkinson et al. J. Med. Chem., (1977), Vol 20, N° 12, 1612-1617)

Method—d—

Intermediate I-14

Preparation of 2-Cyclopentyl-2-fur-2-yl-2-hydroxyacetic acid (3R)-1-azabicyclo[2.2.2]oct-3-yl ester Cyclopentylmagnesium cloride, 0.0472 mol (23.6 ml of a solution 2M in ether) was added to a solution of 9.4 g (0.0377 mol) of 2-fur-2-yl-2-oxoacetic acid (3R)-1-azabicyclo[2.2.2]oct-3-yl ester dissolved in 125 ml of THF, at −70° C. under a N$_2$ atmosphere. The mixture was stirred at this temperature for 10 minutes, and then warmed to room temperature. After 16 h, the reaction mixture was treated with a saturated solution of ammonium chloride and extracted twice with ethyl acetate. The organic phases were combined, washed with water, and dried over MgSO$_4$. After removal of the solvent, the oil obtained (7.5 g) was purified by chromatography on silica gel eluting with chloroform/methanol/ammonia 95:5:0.5. Appropiate fractions were combined and evaporated to obtain the two diastereomers: I-14a, I-14b Intermediate I-14a (2S)-2-Cyclopentyl-2-fur-2-yl-2-hydroxyacetic acid (3R)-1-azabicyclo[2.2.2]oct-3-yl ester 1.55 g of an oil corresponding to the first eluted diastereomer was triturated with a mixture of isopropyl ether/petroleum ether 1:1, to give 0.24 g (4%, based on single isomer) of a solid whose structure was confirmed by $^1$H-NMR as a pure diastereomer; mp=109.6-110.6° C.
$[\alpha]^{22}_D$=+19.7° (c=1, CHCl$_3$)
$^1$H-NMR (CDCl$_3$): δ 1.22-1.37 (m, 1H), 1.40-1.80 (m, 11H), 1.97 (m, 1H), 2.74-2.96 (m, 6H), 3.19-3.30 (m, 1H), 3.80 (bs, 1H, OH), 4.85-4.89 (m, 1H), 6.34-6.37 (m, 2H), 7.35 (m, 1H)
MS: [M+1]$^+$=320.
Intermediate I-14a was hydrolised (EtOH/NaOH 2N, 2 h r.t.) to give (+)-2-Cyclopentyl-2-fur-2-yl-2-hydroxyacetic acid: $[\alpha]^{22}_D$=+31.95° (c=1, EtOH).
Configuration S was assigned. (See TABLE 1).

Intermediate I-14b (2R)-2-Cyclopentyl-2-fur-2-yl-2-hydroxyacetic acid (3R)-1-azabicyclo[2.2.2]oct-3-yl ester 1.10 g of a solid corresponding to the second eluted diastereomer was triturated with a mixture of isopropyl ether/petroleum ether 1:1, to give 0.42 g (7%, based on single isomer) of a solid whose structure was confirmed by $^1$H-NMR as a pure diastereomer; mp=119.9-122.1° C.
$[\alpha]^{22}_D$=−14.2° (c=1, CHCl$_3$)

¹H-NMR (CDCl₃): δ 1.40-1.90 (m, 12H), 2.07 (m, 1H), 2.49-2.56 (m, 1H), 2.67-2.86 (m, 5H), 3.12-3.24 (m, 1H), 3.80 (bs, 1H, OH), 4.87-4.91 (m, 1H), 6.35-6.39 (m, 2H), 7.38 (m, 1H)

MS: [M+1]⁺=320

Intermediate I-14b was hydrolised (EtOH/NaOH 2N, 2 h r.t.) to give (−)-2-Cyclopentyl-2-fur-2-yl-2-hydroxyacetic acid: $[\alpha]^{22}_D$=−32.10° (c=1, EtOH).

Configuration R was assigned. (See TABLE 1).

(2-Fur-2-yl-2-oxoacetic acid (3R)-1-azabicyclo[2.2.2]oct-3-yl ester may be prepared as described in WO 01/04118)

Intermediate I-15

Preparation of 2-Cyclopentyl-2-hydroxy-2-thien-2-ylacetic acid (3R)-1-azabicyclo[2.2.2]oct-3-yl ester Prepared using the same method as for Intermediate I-14, but from 20.8 g (0.0784 mol) of 2-oxo-2-thien-2-ylacetic acid (3R)-1-azabicyclo[2.2.2]oct-3-yl ester and cyclopentylmagnesium cloride, 0.08 mol (40 ml of a solution 2M in ether). The oil obtained (15.64 g) was purified by chromatography on silica gel eluting with chloroform/methanol/ammonia 97:3:0.5 to obtain 8.38 g (32%) of a pure product, mixture of diastereomers: I-15a and I-15b. Structure confirmed by ¹H-NMR.

Intermediate I-15a (2S)-2-Cyclopentyl-2-hydroxy-2-thien-2-ylacetic acid (3R)-1-azabicyclo[2.2.2]oct-3-yl ester The oil mixture of diastereomers was treated with isopropyl ether to obtain a solid, that was treated again with isopropyl ether to yield 2.2 g of a pure diastereomer (Intermediate I-15a, 16.7% based on a single isomer).

$[\alpha]^{22}_D$=−5.75° (c=1, CHCl₃); mp: 152-157° C.

¹H-NMR (CDCl₃): δ 1.40-1.80 (m, 11H), 1.80-2.0 (m, 1H), 2.10 (m, 1H), 2.52-2.65 (m, 1H), 2.70-2.95 (m, 5H), 3.10-3.22 (m, 1H), 4.07 (s, 1H, OH), 4.85-4.95 (m, 1H), 6.95-7.05 (m, 1H), 7.10-7.20 (m, 1H), 7.20-7.27 (m, 1H).

MS: [M+1]⁺=336

Intermediate I-15a was hydrolised (EtOH/NaOH 2N, 2 h r.t. and 2 h at 60° C.) to give (−)-2-Cyclopentyl-2-hydroxy-2-thien-2-ylacetic acid: $[\alpha]^{22}_D$=−6.44° (c=1, EtOH).

Configuration S was assigned. (See TABLE 1).

Intermediate I-15b (2R)-2-Cyclopentyl-2-hydroxy-2-thien-2-ylacetic acid (3R)-1-azabicyclo[2.2.2]oct-3-yl ester The mother liquors of the first crystallization of intermediate I-15a were evaporated, and the oil obtained treated with isopropyl ether to give a solid, that was treated again with isopropyl ether to yield 1.47 g of the second diastereomer intermediate I-15b (11.2% based on single isomer).

$[\alpha]^{22}_D$=+22.49° (c=1, CHCl₃); mp: 99-102° C.

¹H-NMR (CDCl₃): δ 1.25-1.85 (m, 12H), 2.0 (m, 1H), 2.65-2.95 (m, 6H), 3.22-3.34 (m, 1H), 4.05 (s, 1H, OH), 4.80-4.92 (m, 1H), 6.90-7.0 (m, 1H), 7.10-7.16 (m, 1H), 7.20-7.27 (m, 1H).

MS: [M+1]⁺=336

Intermediate I-15b was hydrolised (EtOH/NaOH 2N, 2 h r.t. and 2 h at 60° C.) to give (+)-2-Cyclopentyl-2-hydroxy-2-thien-2-ylacetic acid: $[\alpha]^{22}_D$=+6.63° (c=1, EtOH).

Configuration R was assigned. (See TABLE 1).

(Intermediates I-15a and I-15b have also been prepared following method c)

(2-Oxo-2-thien-2-ylacetic acid (3R)-1-azabicyclo[2.2.2]oct-3-yl ester may be prepared as described in WO 01/04118)

Intermediate I-16

Preparation of 2-Cyclohexyl-2-hydroxy-2-phenylacetic acid (3R)-1-azabicyclo[2.2.2]oct-3-yl ester Cyclohexylmagnesium cloride, 0.127 mol (63.6 ml of a solution 2M in ether), was added to a solution of 28.7 g (0.111 mol) of 2-oxo-2-phenylacetic acid (3R)-1-azabicyclo[2.2.2]oct-3-yl ester dissolved in 350 ml of THF, at −70° C. under a N₂ atmosphere. The mixture was stirred at this temperature for 10 minutes, and then warmed to room temperature. After 1 h, the reaction mixture was treated with a saturated solution of ammonium chloride and extracted twice with ethyl acetate. The organic phases were combined, washed with water, and dried over MgSO₄. After removal of the solvent, the oil obtained (27.0 g) was purified by chromatography on silica gel eluting with chloroform/methanol 10:1. The yield was 18.7 g (49.2%) of a pure product, mixture of diastereomers: I-16a and I-16b.

Intermediate I-16a (2R)-2-Cyclohexyl-2-hydroxy-2-phenylacetic acid (3R)-1-azabicyclo[2.2.2]oct-3-yl ester 16 g of the oil mixture of diastereomers were dissolved in isopropanol and treated with 5.4 g of fumaric acid. After cooling to 0-5° C., 8 g of the fumarate salt of the first diastereomer (Intermediate I-16a) were obtained.

Fumarate salt: MS: [M (free base)+1]⁺=344.

The 8 g of this salt were recrystallised from isopropanol to obtain 5 g of a more pure product. This salt was treated with CHCl₃ and K₂CO₃ solution to obtain the free base Intermediate I-16a.

I-16a (free base):

$[\alpha]^{22}_D$=−14.9° (c=1, CHCl₃).

¹H-NMR (COCl₃): δ 1.0-1.95 (m, 14H), 2.04-2.12 (m, 1H), 2.16-2.32 (m, 1H), 2.38-2.50 (m, 1H), 2.64-2.96 (m, 4H), 3.04-3.16 (m, 1H), 3.70-3.85 (s, 1H, OH), 4.85-4.90 (m, 1H), 7.25-7.40 (m, 3H), 7.60-7.70 (m, 2H).

Intermediate I-16a (free base) was hydrolised (EtOH/NaOH 2N, 7 h at 60° C.) to give (−)-2-Cyclohexyl-2-hydroxy-2-phenylacetic acid as a pure enantiomer $[\alpha]^{22}_D$=−23.6° (c=1.4, EtOH). This value was assigned to the R configuration provided that in the literature (A. Tambuté, A. Collet; Bulletin de la Société Chimique de France, 1984, N° 1-2, pages II-77 to II-82) the (2S)-2-Cyclohexyl-2-hydroxy-2-phenylacetic acid has been described with $[\alpha]^{24}_D$=+25.2° (c=1.4, EtOH). (See TABLE 1).

Intermediate I-16b (2S)-2-Cyclohexyl-2-hydroxy-2-phenylacetic acid (3R)-1-azabicyclo[2.2.2]oct-3-yl ester The mother liquors of the fumarate salt of the Intermediate I-16a were evaporated and the residue dissolved in water. The obtained solution was washed with ether, basified with K₂CO₃ and extracted with CHCl₃. The organic layer was dried over MgSO₄ and the solvent was evaporated. The oil obtained (7.5 g) was dissolved in 50 ml of isopropanol and treated with EtOH/HCl(g). After the addition of 75 ml of ethyl ether, 3.1 g of the chlorhidrate salt of the second diasteroemer, Intermediate I-16b, were obtained.

Chlorhidrate salt: MS: [M (free base)+1]$^+$=344.

The chlorhidrate salt was treated with $CHCl_3$ and $K_2CO_3$ solution to obtain the free base Intermediate I-16b.

I-16b (free base):

$[\alpha]^{22}_D$=+25.3° (c=1, $CHCl_3$).

$^1$H-NMR ($CDCl_3$): δ 1.0-1.78 (m, 13H), 1.78-1.90 (m, 1H), 1.92-2.0 (m, 1H), 2.20-2.34 (m, 1H), 2.66-2.96 (m, 5H), 3.20-3.32 (m, 1H), 3.70-3.85 (s, 1H, OH), 4.75-4.85 (m, 1H), 7.25-7.40 (m, 3H), 7.60-7.70 (m, 2H).

Intermediate I-16b (free base) was hydrolised (EtOH/ NaOH 2N, 60° C., 8 h) to give (+)-2-Cyclohexyl-2-hydroxy-2-phenylacetic acid as a pure enantiomer $[\alpha]^{22}_D$=+23.1° (c=1.4, EtOH). This value was assigned to the S configuration according with the results obtained with Intermediate I-16a. (See TABLE 1).

(2-Oxo-2-phenylacetic acid (3R)-1-azabicyclo[2.2.2]oct-3-yl ester may be prepared as described in WO 92/04346.)

Intermediate I-17

2-hydroxy-2,3-diphenylpropionic acid (3R)-1-azabicyclo[2.2.2]oct-3-yl ester

Prepared using the same method as for Intermediate I-16 as a mixture of diastereomers I-17a and I-17b, which were separated by crystallisation using ether/isopropyl ether.

Intermediate I-17a (2*)-2-hydroxy-2,3-diphenylpropionic acid (3R)-1-azabicyclo[2.2.2]oct-3-yl ester, first diastereomer obtained The yield was 0.87 g (42.6% based on single isomer), mp: 132° C.

$^1$H-NMR ($CDCl_3$): δ 1.30-1.60 (m, 2H), 1.60-1.90 (m, 2H), 2.05 (m, 1H), 2.20-2.35 (m, 1H), 2.50-2.90 (m, 4H), 3.0-3.15 (m, 1H), 3.25 and 3.60 (dd, 2H), 3.70 (bs, 1H, OH), 4.70-4.80 (m, 1H), 7.15-7.45 (m, 8H), 7.65-7.75 (m, 2H).

MS: [M+1]$^+$=352

((*): Configuration not assigned)

Intermediate I-17b (2*)-2-hydroxy-2,3-diphenylproplonic acid (3R)-1-azabicyclo[2.2.2]oct-3-yl ester, second diastereomer obtained The yield was 0.23 g (11.2% based on single isomer), mp: 107° C.

$^1$H-NMR ($CDCl_3$): δ 1.20-1.35 (m, 1H), 1.35-1.55 (m, 2H), 1.55-1.70 (m, 1H), 1.80-1.95 (m, 1H), 2.55-2.90 (m, 5H), 3.10-3.20 (m, 1H), 3.25 and 3.60 (dd, 2H), 3.80 (bs, 1H, OH), 4.65-4.80 (m, 1H), 7.20-7.50 (m, 8H), 7.65-7.75 (m, 2H).

MS: [M+1]$^+$=352

((*): Configuration not assigned)

Intermediate I-18

2-Hydroxy-3-phenyl-2-thien-2-ylpropionic acid (3R)-1-azabicyclo[2.2.2]oct-3-yl ester Prepared using the same method as for Intermediate I-15 as a mixture of diastereomers. The yield was 0.81 g (54%). The product was purified by preparation of the chlorhidrate salt, 0.57 g of this salt were obtained (63% from the free base).

Chlorhidrate salt:

$^1$H-NMR (DMSO-$d_6$): δ 1.40-1.60 (m, 1H), 1.60-1.95 (m, 3H), 2.05 and 2.10 (m, 1H), 2.75-3.65 (m, 8H), 4.90-5.05 (m, 1H), 6.50 and 6.55 (s, 1H, OH), 6.95-7.05 (m, 1H), 7.10-7.30 (m, 6H), 7.40-7.50 (m, 1H), 10.9 (bs, 1H, NH$^+$).

MS: [M+1]$^+$=358

Intermediate I-19

2-Hydroxy-2-thien-2-ylpent-3-ynoic acid (3R)-1-azabicyclo[2.2.2]oct-3-yl ester

Prepared using the same method as for Intermediate I-15 as a mixture of diastereomers. The yield was 1.88 g (25.6%)

$^1$H-NMR ($CDCl_3$): δ 1.20-1.90 (m, 4H), 1.92 and 1.96 (s, 3H, CH3), 2.0 and 2.16 (m, 1H), 2.45-2.90 (m, 5H), 3.05-3.20 and 3.15-3.27 (m, 1H), 4.85-4.92 (m, 1H), 6.94-7.0 (m, 1H), 7.24-7.30 (m, 2H), the signal for OH group is observed between 4.5 and 5.5 as a broad band.

MS: [M+1]$^+$=306

Intermediate I-20

2-Hydroxy-2-thien-2-ylbut-3-enoic acid (3R)-1-azabicyclo[2.2.2]oct-3-yl ester

Prepared using the same method as for Intermediate I-15 as a mixture of diastereomers. The yield was 1.74 g (18.8%)

$^1$H-NMR ($CDCl_3$): δ 1.30-1.90 (m, 4H), 2.05-2.15 (m, 1H), 2.60-3.0 (m, 5H), 3.15-3.35 (m, 1H), 3.40-4.70 (broad band, 1H, OH), 4.85-4.95 (m, 1H), 5.30-5.40 (m, 1H), 5.60-5.75 (m, 1H), 6.30-6.50 (m, 1H), 6.95-7.05 (1H), 7.10-7.15 (m, 1H), 7.25-7.30 (m, 1H).

MS: [M+1]$^+$=294

Intermediate I-21

2-Hydroxy-4-phenyl-2-thien-2-ylbutyric acid (3R)-1-azabicyclo[2.2.2]oct-3-yl ester Prepared using the same method as for Intermediate I-15 as a mixture of diastereomers. The yield was 0.29 g (2.4%).

$^1$H-NMR ($CDCl_3$): δ 1.25-1.95 (m, 4H), 1.95-2.10 (m, 1H), 2.30-3.0 (m, 9H), 3.10-3.25 (m, 1H), 4.80-4.90 (m, 1H), 6.95-7.05 (m, 1H), 7.05-7.40 (m, 7H).

MS: [M+1]$^+$=372

Method—e—

Intermediate I-22

Preparation of 2-Hydroxymethyl-2,3-diphenylpropionic acid (3R)-1-azabicyclo[2.2.2]oct-3-yl ester Lithium diisopropylamide (0.0048 mol) 2.40 ml of a 2M solution (in heptane/THF/ethylbenzene) was added to a stirred solution of 1.5 g (0.0045 mol) of 2,3-diphenylpropionic acid (3R)-1-azabicyclo[2.2.2]oct-3-yl ester in 30 ml of THF at −70° C. under a $N_2$ atmosphere. $CH_2O$ (gas) was bubbled into the reaction mixture via a steady stream of dry $N_2$ during 10 min at −70° C. and then while the mixture was warmed at room temperature. The reaction was quenched by addition of saturated ammonium chloride solution (100 ml) and the resultant mixture was extracted twice with 100 ml of ethyl acetate. The organic layers were combined, dried over MgSO$_4$ and evaporated to yield 1.9 g of an oil. This 1.9 g were combined with 3.28 g of a previous preparation and the product obtained (5.18 g) was purified by chromatography on silica gel eluting with chloroform/methanol/ammonia from 97.5:2.5:0.25 to 90:10:1. Appropiate fractions were combined and evaporated to obtain the two diastereomers: Intermediates I-22a and I-22b Intermediate I-22a (2*)-2-Hydroxymethyl-2,3-diphenylpropionic acid (3R)-1-azabicyclo[2.2.2]oct-3-yl ester 1.25 g of a solid corresponding to the first eluted diastereomer was triturated with isopropyl ether, to give 0.95 g (42%, based on single isomer) of a white solid whose structure was confirmed by $^1$H-NMR as a pure diastereomer; mp: 119° C.

$^1$H-NMR (CDCl$_3$): δ 1.20-1.35 (m, 1H), 1.40-1.70 (m, 3H), 1.90 (m, 1H), 2.5 (bs, OH) 2.60-2.85 (m, 5H), 3.15-3.25 (m, 1H), 3.40-3.50 (dd, 2H), 3.95-4.10 (dd, 2H), 4.85 (m, 1H), 7.05 (m, 2H), 7.15-7.40 (m, 8H)

MS: [M+1]$^+$=366

((*): Configuration not assigned)

Intermediate I-22b (2*)-2-Hydroxymethyl-2,3-diphenylpropionic acid (3R)-1-azabicyclo[2.2.2]oct-3-yl ester 1.84 g of an oil corresponding to the second eluted diastereomer was purified by column chromatography (in the above described conditions) to yield 1.26 g of a solid that after trituration with isopropyl ether yield 0.95 g of a white solid whose structure was confirmed by $^1$H-NMR as a pure diastereomer (42%, based on single isomer);

mp: 154° C.

$^1$H-NMR (CDCl$_3$): δ 1.20-1.35 (m, 1H), 1.50-1.75 (m, 3H), 2.0 (m, 1H), 2.35 (bs, OH), 2.50-2.80 (m, 5H), 3.10-3.20 (m, 1H), 3.35-3.50 (dd, 2H), 3.95-4.10 (dd, 2H), 4.85 (m, 1H), 7.0 (m, 2H), 7.15-7.40 (m, 8H).

MS: [M+1]$^+$=366

((*): Configuration not assigned)

Also included within the scope of the present invention are pharmaceutical compositions which comprise, as the active ingredient, at least one quinuclidine derivative of general formula (I) in association with a pharmaceutically acceptable carrier or diluent. Preferably the composition is made up in a form suitable for oral administration.

The pharmaceutically acceptable carrier or diluents which are mixed with the active compound or compounds, to form the composition of this invention are well-known per se and the actual excipients used depend inter alia on the intended method of administration of the composition.

Compositions of this invention are preferably adapted for oral administration. In this case, the composition for oral administration may take the form of tablets, film-coated tablets, liquid inhalant, powder inhalant and inhalation aerosol; all containing one or more compounds of the invention; such preparations may be made by methods well-known in the art.

The diluents which may be used in the preparations of the compositions include those liquid and solid diluents which are compatible with the active ingredient, together with colouring or flavouring agents, if desired. Tablets or film-coated tablets may conveniently contain between 1 and 500 mg, preferably from 5 to 300 mg of active ingredient. The inhalant compositions may contain between 1 μg and 1,000 μg, preferably from 10 μg to 800 μg of active ingredient. In human therapy, the dose of the compound of general formula (I) depend on the desired effect and duration of treatment; adult doses are generally between 3 mg and 300 mg per day as tablets and 10 μg and 800 μg per day as inhalant composition.

Pharmacological Action

The results on human muscarinic receptors binding and in the test on bronchospasm in guinea pig, were obtained as described below.

Human Muscarinic Receptor Studies.

The binding of [3H]-NMS to human muscarinic receptors was performed according to Waelbroek et al (1990), Mol. Pharmacol., 38: 267-273. Assays were carried out at 25° C. Membrane preparations from stably transfected chinese hamster ovary-K1 cells (CHO) expressing the genes for the human muscarinic receptors M3 were used.

For determination of IC$_{50}$, membrane preparations were suspended in DPBS to a final concentration of 89 μg/ml for the M3 subtype. The membrane suspension was incubated with the tritiated compound for 60 min. After incubation the membrane fraction was separated by filtration and the bound radioactivity determined. Non specific binding was determined by addition of 10$^{-4}$ M atropine. At least six concentrations were assayed in duplicate to generate individual displacement curves.

Our results show that the compounds of the present invention have high affinities for muscarinic M3 receptors, preferably human muscarinic receptors. Affinity levels have been measured by in vitro assays as described above at 100 nM and 10 nM. Preferred compounds of the invention produce an inhibition of [3H]-NMS binding of at least 35% at 10 nM and of at least 65% at 100 nM (Table 2).

TABLE 2

| N° COMPOUND | % INHIBITION concentration: 1,00E-07 M | % INHIBITION concentration: 1,00E-08 M |
|---|---|---|
| Atropine | 88.3 | 69.75 |
| Ipratropium bromide | 93.75 | 67.25 |
| 13 | 76 | 36 |
| 14 | 76.5 | 39.0 |
| 16 | 74.2 | 36.3 |
| 22 | 81.5 | 72 |
| 23 | 75.6 | 63.3 |
| 24 | 78 | 56.6 |
| 25 | 76.1 | 62.6 |
| 26 | 75.6 | 63.8 |
| 28 | 78.3 | 60.6 |
| 29 | 79.0 | 53.8 |
| 31 | 74.3 | 54.3 |
| 32 | 73.9 | 44.5 |
| 33 | 72.8 | 46.7 |
| 34 | 85.3 | 68.3 |
| 36 | 84.2 | 42.0 |
| 37 | 88.1 | 72.6 |
| 38 | 86.3 | 57.7 |
| 40 | 86.9 | 72.7 |
| 43 | 83.4 | 58.7 |
| 44 | 84.6 | 44.6 |
| 46 | 87.1 | 57.6 |
| 53 | 81.5 | 58 |
| 54 | 72.5 | 44.1 |
| 56 | 77.3 | 53.8 |
| 57 | 77.4 | 47.1 |
| 61 | 75.1 | 39.9 |
| 64 | 78.6 | 64.5 |
| 65 | 79.8 | 66.0 |
| 67 | 75.1 | 52.5 |
| 69 | 70.8 | 43.9 |
| 70 | 71.2 | 50.0 |
| 80 | 72.4 | 55.8 |

TABLE 2-continued

| N° COMPOUND | % INHIBITION concentration: 1,00E-07 M | % INHIBITION concentration: 1,00E-08 M |
|---|---|---|
| 81 | 70.1 | 45.4 |
| 82 | 70.6 | 55.3 |
| 83 | 72.7 | 60.3 |
| 84 | 68.3 | 41.0 |
| 86 | 68.2 | 37.2 |
| 88 | 65.5 | 35.7 |
| 89 | 68.5 | 51.3 |
| 92 | 69.4 | 49.2 |

Test on Bronchospasm in Guinea Pig

The studies were performed according to H. Konzett and F. Rössler (1940), Arch. Exp. Path. Pharmacol. 195: 71-74. Aqueous solutions of the agents to be tested were nebulized and inhaled by anaesthetized ventilated male guinea pigs (Dunkin-Hartley). Bronchial response to intravenous acetylcholine challenge was determined before and after drug administration and the changes in pulmonary resistance at several time-points were expressed as percent of inhibition of bronchoespasm.

The compounds of the present invention inhibited the bronchospasm response to acetylcholine with high potency and a long duration of action.

From the above described results one of ordinary skill in the art can readily understand that the compounds of the present invention have excellent antimuscarinic activity (M3) and thus are useful for the treatment of diseases in which the muscarinic M3 receptor is implicated, including respiratory disorders such as chronic obstructive pulmonary disease (COPD), bronchitis, bronchial hyperreactivity, asthma, cough and rhinitis; urological disorders such as urinary incontinence, pollakiuria, neurogenic or unstable bladder, cystospasm and chronic cystitis; gastrointestinal disorders such as irritable bowel syndrome, spastic colitis, diverticulitis and peptic ulceration; and cardiovascular disorders such as vagally induced sinus bradycardia. For example, the compounds of the present invention are useful for the treatment of respiratory diseases such as chronic obstructive pulmonary disease, chronic bronchitis, asthma, and rhinitis; urinary diseases such as urinary incontinence and pollakinuria in neuripenia pollakinuria, neurogenic bladder, nocturnal enuresis, unstable bladder, cytospasm and chronic cystitis; and gastrointestinal diseases such as irritable bowel syndrome, spastic colitis and diverticulitis.

The present invention further provides a compound of formula (I) or a pharmaceutically acceptable composition comprising a compound of formula (I) for use in a method of treatment of the human or animal body by therapy, in particular for the treatment of respiratory, urological or gastrointestinal disease or disorder.

The present invention further provides the use of a compound of formula (I) or a pharmaceutically acceptable composition comprising a compound of formula (I) for the manufacture of a medicament for the treatment of a respiratory, urological or gastrointestinal disease or disorder.

Further, the compounds of formula (I) and pharmaceutical compositions comprising a compound of formula (I) can be used in a method of treating a respiratory, urological or gastrointestinal disease or disorder, which method comprises administering to a human or animal patient in need of such treatment an effective, non-toxic, amount of a compound of formula (I) or a pharmaceutical composition comprising a compound of formula (I).

Further, the compounds of formula (I) and pharmaceutical compositions comprising a compound of formula (I) can be used in combination with other drugs effective in the treatment of these diseases. For example with $\beta_2$ agonists, steroids, antiallergic drugs, phosphodiesterase IV inhibitors and/or leukotriene D4 (LTD4) inhibitors, for simultaneous, separate or sequential use in the treatment of a respiratory disease.

The present invention therefore further provides a combination product comprising
  (i) a compound according to the invention; and
  (ii) another compound effective in the treatment of a respiratory, urological or gastrointestinal disease or disorder
for simultaneous, separate or sequential use.

The compound (ii) which is effective in the treatment of a respiratory, urological or gastrointestinal disease or disorder may be a $\beta_2$ agonist, steroid, antiallergic drug, phosphodiesterase IV inhibitor and/or leukotriene D4 (LTD4) antagonist when the product is for simultaneous, separate or sequential use in the treatment of a respiratory disease. Alternatively, the compound (ii) may be a $\beta_2$ agonist, steroid, antiallergic drug and/or phosphodiesterase IV inhibitor when the product is for simultaneous, separate or sequential use in the treatment of a respiratory disease.

The present invention will be further illustrated by the following examples. The examples are given by way of illustration only and are not to be construed as limiting.

EXAMPLE 1

(3R)-3-(2,3-Diphenylpropionyloxy)-1-(3-phenoxypropyl)-1-azoniabicyclo[2.2.2]octane trifluoroacetate The title compound was synthesised as a mixture of diastereomers according to methods c, and b from the Intermediate I-2. The yield of the final step was 20 mg, 71%.

MS [M-CF$_3$COO]$^+$: 470.

$^1$H-NMR (DMSO-d$_6$): δ 1.50-1.72 (m, 2H), 1.75-1.95 (m, 2H), 1.97-2.15 (m, 3H), 2.95-3.15 (m, 4H), 3.20-3.50 (m, 5H), 3.75-3.85 (m, 1H), 3.95-4.15 (m, 3H), 4.95-5.05 (m, 1H), 6.90-7.0 (m, 4H), 7.15-7.45 (m, 11H).

EXAMPLE 2

(3R)-3-(2,3-Diphenylpropionyloxy)-1-(3-thien-2-ylpropyl)-1-azoniabicyclo[2.2.2]octane trifluoroacetate The title compound was synthesised as a mixture of diastereomers according to methods c, and b from the Intermediate I-2. The yield of the final step was 15 mg, 55%.

MS [M-CF$_3$COO]$^+$: 460.

$^1$H-NMR (DMSO-d$_6$): δ 1.50-1.70 (m, 2H), 1.70-2.0 (m, 4H), 2.0-2.15 (m, 1H), 2.75-2.85 (m, 2H), 2.85-3.20 (m, 4H), 3.20-3.45 (m, 5H), 3.70-3.82 (m, 1H), 4.02-4.12 (m, 1H), 4.95-5.02 (m, 1H), 6.90-7.05 (m, 2H), 7.10-7.45 (m, 11H)

EXAMPLE 3

(3R)-3-[(2*)-2-Hydroxymethyl-2,3-diphenylpropionyloxy]-1-(3-thien-2-ylpropyl)-1-azoniabicyclo[2.2.2]octane trifluoroacetate (diastereomer 1)

The title compound was synthesised according to methods e, and b from the Intermediate I-22a. The yield of the final step was 15 mg, 52%.

MS [M-CF$_3$COO]$^+$: 490.

¹H-NMR (DMSO-d₆): δ 1.55-1.75 (m, 2H), 1.75-2.05 (m, 4H), 2.21 (m, 1H), 2.75-2.85 (m, 2H), 2.85-2.95 (m, 1H), 3.05-3.45 (m, 8H), 3.75-3.87 (m, 2H), 3.92-4.0 (m, 1H), 5.08 (m, 1H), 5.20-5.23 (t, 1H, OH), 6.82-6.90 (m, 2H), 6.90-6.95 (m, 1H), 6.95-7.02 (m, 1H), 7.05-7.20 (m, 5H), 7.20-7.35 (m, 3H), 7.37-7.42 (m, 1H).

EXAMPLE 4

(3R)-3-[(2*)-2-Hydroxymethyl-2,3-diphenylpropionyloxy]-1-phenethyl-1-azoniabicyclo[2.2.2]octane trifluoroacetate (diastereomer 1)

The title compound was synthesised according to methods e, and b from the Intermediate I-22a. The yield of the final step was 18 mg, 64%.

MS $[M-CF_3COO]^+$: 470.

¹H-NMR (DMSO-d₆): δ 1.62-1.75 (m, 2H), 1.80-2.05 (m, 2H), 2.26 (m, 1H), 2.90-3.12 (m, 3H), 3.20-3.55 (m, 8H), 3.80-4.02 (m, 3H), 5.10-5.17 (m, 1H), 5.20-5.25 (t, 1H, OH); 6.82-6.90 (m, 2H), 7.10-7.20 (m, 5H), 7.22-7.40 (m, 8H).

EXAMPLE 5

(3R)-3-[(2*)-2-Hydroxymethyl-2,3-diphenylpropionyloxy]-1-(3-thien-2-ylpropyl)-1-azoniabicyclo[2.2.2]octane trifluoroacetate (diastereomer 2)

The title compound was synthesised according to methods e, and b from the Intermediate I-22b. The yield of the final step was 10.1 mg, 37.5%.

MS $[M-CF_3COO]^+$: 490.

¹H-NMR (DMSO-d₆): δ 1.45-1.60 (m, 1H), 1.60-1.75 (m, 1H), 1.80-2.05 (m, 4H), 2.18 (m, 1H), 2.75-2.90 (m, 2H), 2.95-3.10 (m, 1H), 3.10-3.55 (m, 8H), 3.75-3.92 (m, 2H), 4.0-4.12 (m, 1H), 5.05-5.15 (m, 1H), 5.25-5.35 (t, 1H, OH), 6.70-6.85 (m, 2H), 6.90-7.20 (m, 7H), 7.20-7.35 (m, 3H), 7.35-7.42 (m, 1H).

EXAMPLE 6

(3R)-3-[(2*)-2-Hydroxymethyl-2,3-diphenylpropionyloxy]-1-phenethyl-1-azoniabicyclo[2.2.2]octane trifluoroacetate (diastereomer 2)

The title compound was synthesised according to methods e, and b from the Intermediate I-22b. The yield of the final step was 22 mg, 76%.

MS $[M-CF_3COO]^+$: 470.

¹H-NMR (DMSO-d₆): δ 1.50-1.60 (m, 1H), 1.60-1.80 (m, 1H), 1.85-2.05 (m, 2H), 2.21 (m, 1H), 2.90-3.10 (m, 2H), 3.12-3.55 (m, 9H), 3.78-3.83 (m, 1H), 3.88-3.95 (m, 1H), 4.07-4.12 (m, 1H), 5.15-5.20 (m, 1H), 5.35-5.40 (t, 1H, OH), 6.75-6.80 (m, 2H), 7.0-7.15 (m, 3H), 7.20-7.40 (m, 8H).

EXAMPLE 7

(3R)-3-[(2*)-2-Hydroxy-2,3-diphenylpropionyloxy]-1-(3-phenoxypropyl)-1-azoniabicyclo[2.2.2]octane bromide (diastereomer 1)

The title compound was synthesised according to methods d, and a from the Intermediate I-17a. The yield of the final step was 380 mg, 96%.

MS $[M-Br]^+$: 486, mp: 1.03° C.

¹H-NMR (DMSO-d₆): δ 1.65-1.75 (m, 2H), 1.75-2.02 (m, 2H), 2.02-2.15 (m, 2H), 2.24 (m, 1H), 3.05-3.25 (m, 2H), 3.25-3.55 (m, 7H), 3.78-3.90 (m, 1H), 3.98-4.08 (m, 2H), 5.02-5.10 (m, 1H), 6.20 (s, 1H, OH), 6.92-7.0 (m, 3H), 7.10-7.22 (m, 5H), 7.25-7.40 (m, 5H), 7.52-7.58 (m, 2H).

EXAMPLE 8

(3R)-3-[(2*)-2-Hydroxy-2,3-diphonylpropionyloxy]-1-(2-phenoxyethyl)-1-azoniabicyclo[2.2.2]octane bromide (diastereomer 1)

The title compound was synthesised according to methods d, and a from the Intermediate I-17a. The yield of the final step was 320 mg, 83%.

MS $[M-Br]^+$: 472, mp: 223° C.

¹H-NMR (DMSO-d₆): δ 1.70-1.80 (m, 2H), 1.80-2.0 (m, 2H), 2.20 (m, 1H), 3.15-3.55 (m, 7H), 3.55-3.70 (m, 2H), 3.85-4.0 (m, 1H), 4.30-4.45 (m, 2H), 5.0-5.10 (m, 1H), 6.10 (s, 1H, OH), 6.90-7.05 (m, 3H), 7.05-7.20 (m, 5H), 7.20-7.40 (m, 5H), 7.45-7.55 (m, 2H).

EXAMPLE 9

(3R)-3-[(2*)-2-Hydroxy-2,3-diphenylpropionyloxy]-1-(3-phenoxypropyl)-1-azoniabicyclo[2.2.2]octane trifluoroacetate (diastereomer 2)

The title compound was synthesised according to methods d, and b from the Intermediate I-17b. The yield of the final step was 7.2 mg, 25%.

MS $[M-CF_3COO]^+$: 486.

¹H-NMR (DMSO-d₆): δ 1.40-1.55 (m, 1H), 1.55-1.70 (m, 1H), 1.75-2.0 (m, 2H), 2.11 (m, 3H), 3.10-3.60 (m, 9H), 3.77-3.87 (m, 1H), 4.0-4.1 (m, 2H), 5.0-5.1 (m, 1H), 6.14 (s, 1H, OH), 6.90-7.0 (m, 3H), 7.15-7.25 (m, 5H), 7.25-7.42 (m, 5H), 7.60-7.67 (m, 2H).

EXAMPLE 10

(3R)-3-[(2*)-2-Hydroxy-2,3-diphenylpropionyloxy]-1-(2-phenoxyethyl)-1-azoniabicyclo[2.2.2]octane trifluoroacetate (diastereomer 2)

The title compound was synthesised according to methods d, and b from the Intermediate I-17b. The yield of the final step was 5.4 mg, 19%.

MS $[M-CF_3COO]^+$: 472.

¹H-NMR (DMSO-d₆): δ 1.40-1.55 (m, 1H), 1.55-1.70 (m, 1H), 1.80-2.0 (m, 2H), 2.12 (m, 1H), 3.20-3.60 (m, 7H), 3.60-3.70 (m, 2H), 3.90-4.0 (m, 1H), 4.42 (m, 2H), 5.0-5.1 (m, 1H), 6.15 (s, 1H, OH), 6.95-7.05 (m, 3H), 7.10-7.22 (m, 5H), 7.25-7.40 (m, 5H), 7.57-7.65 (m, 2H).

EXAMPLE 11

(3R)-3-(2-Hydroxy-3-phenyl-2-thien-2-ylpropionyloxy)-1-(3-phenoxypropyl)-1-azoniabicyclo[2.2.2]octane trifluoroacetate The title compound was synthesised as a mixture of diastereomers according to methods d, and b from Intermediate I-18. The yield of the final step was 15 mg, 52%.

MS $[M-CF_3COO]^+$: 492.

¹H-NMR (DMSO-d₆): δ 1.45-1.70 (m, 1H), 1.75-2.0 (m, 3H), 2.0-2.30 (m, 3H), 3.0-3.17 (m, 1H), 3.17-3.57 (m, 8H), 3.80-3.90 (m, 1H), 3.97-4.10 (m, 2H), 5.02-5.05 (m, 1H), 6.52-6.60 (d, 1H, OH), 6.90-7.04 (m, 4H), 7.14-7.28 (m, 6H), 7.28-7.38 (m, 2H), 7.42-7.50 (m, 1H).

EXAMPLE 12

(3R)-3-(2-Hydroxy-3-phenyl-2-thien-2-ylpropiony-loxy)-1-(3-thien-2-ylpropyl)-1-azoniabicyclo[2.2.2]octane trifluoroacetate The title compound was synthesised as a mixture of diastereomers according to methods d, and b from Intermediate I-18. The yield of the final step was 21 mg, 74%.

MS [M-CF$_3$COO]$^+$: 482

$^1$H-NMR (DMSO-d$_6$): δ 1.45-1.70 (m, 1H), 1.75-2.05 (m, 5H), 2.05-2.3 (m, 1H), 2.77-2.87 (m, 2H), 2.90-3.10 (m, 1H), 3.10-3.52 (m, 8H), 3.75-3.82 (m, 1H), 5.0-6.07 (m, 1H), 6.52-6.57 (d, 1H, OH), 6.92-7.05 (m, 3H), 7.10-7.27 (m, 6H), 7.37-7.47 (m, 2H).

EXAMPLE 13

(3R)-3-(2-Hydroxy-2-thien-2-ylpent-4-enoyloxy)-1-(3-phenoxypropyl)-1-azoniabicyclo[2.2.2]octane bromide The title compound was obtained as a mixture of diastereomers according to methods c, and a from Intermediate I-3. The yield of the final step was 300 mg, 71%.

MS [M-Br]$^+$: 442, mp: 157°, (described in experimental section, method a)

$^1$H-NMR (DMSO-d$_6$): δ 1.70-2.05 (m, 4H), 2.05-2.35 (m, 3H), 2.70-2.83 (m, 1H), 2.90-3.02 (m, 1H), 3.25-3.60 (m, 7H), 3.82-3.97 (m, 1H), 3.9-74.10 (m, 2H), 5.05-5.25 (m, 3H), 5.70-5.90 (m, 1H), 6.50 (d, 1H, OH), 6.90-7.05 (m, 4H), 7.10-7.20 (m, 1H), 7.27-7.35 (m, 2H), 7.45 (m, 1H).

EXAMPLE 14

(3R)-3-(2-Hydroxy-2-thien-2-ylpent-4-enoyloxy)-1-(3-thien-2-ylpropyl)-1-azoniabicyclo[2.2.2]octane trifluoroacetate The title compound was obtained as a mixture of diastereomers according to methods c, and b from Intermediate I-3. The yield of the final step was 10 mg, 39.3%.

MS [M-CF$_3$COO]$^+$: 432.

$^1$H-NMR (DMSO-d$_6$): δ 1.65-2.18 (m, 6H), 2.18-2.30 (m, 1H), 2.70-3.05 (m, 4H), 3.10-3.55 (m, 4H), 3.55-3.68 (m, 1H), 3.78-3.92 (m, 2H), 4.0-4.1 (m, 1H), 5.0-5.20 (m, 3H), 5.70-5.85 (m, 1H), 6.48-6.52 (d, 1H, OH), 6.90-7.02 (m, 3H), 7.10-7.20 (m, 1H), 7.35-7.42 (m, 1H), 7.42-7.50 (m, 1H).

EXAMPLE 15

(3R)-3-(2-Hydroxy-2-thien-2-ylpent-4-enoyloxy)-1-(2-phenoxyethyl)-1-azoniabicyclo[2.2.2]octane bromide The title compound was obtained as a mixture of diastereomers according to methods c, and a from Intermediate I-3. The yield of the final step was 270 mg, 66%.

MS [M-Br]$^+$: 428, mp: 82° C.

$^1$H-NMR (DMSO-d$_6$): δ 1.72-2.10 (m, 4H), 2.20-2.35 (m, 1H), 2.70-2.85 (m, 1H), 2.90-3.05 (m, 1H), 3.25-3.85 (m, 7H), 3.92-4.12 (m, 1H), 4.35-4.45 (m, 2H), 4.95-5.20 (m, 3H), 5.70-5.90 (m, 1H), 6.50 (s, 1H, OH), 6.90-7.05 (m, 4H), 7.10-7.18 (m, 1H), 7.25-7.45 (m, 3H).

EXAMPLE 16

(3R)-3-(2-Hydroxy-2-thien-2-ylheptanoyloxy)-1-(3-phenoxypropyl)-1-azoniabicyclo[2.2.2]octane trifluoroacetate The title compound was obtained as a mixture of diastereomers according to methods c, and b from Intermediate I-1. The yield of the final step was 16.2 mg, 57%.

MS [M-CF$_3$COO]$^+$: 472.

$^1$H-NMR (DMSO-d$_6$): δ 0.80-0.90 (m, 3H), 1.15-1.40 (m, 6H), 1.65-2.30 (m, 9H), 3.20-3.60 (m, 5H), 3.85-3.95 (m, 1H), 3.95-4.10 (m, 2H), 5.05-5.17 (m, 1H), 6.30-6.35 (d, 1H, OH), 6.90-7.05 (m, 4H), 7.10-7.17 (m, 1H), 7.25-7.35 (m, 2H), 7.42-7.48 (m, 1H).

EXAMPLE 17

(3R)-3-(2-Hydroxy-2-thien-2-ylheptanoyloxy)-1-(3-thien-2-ylpropyl)-1-azoniabicyclo[2.2.2]octane trifluoroacetate The title compound was obtained as a mixture of diastereomers according to methods c, and b from Intermediate I-1. The yield of the final step was 6.8 mg, 12%.

MS [M-CF$_3$COO]$^+$: 462.

$^1$H-NMR (DMSO-d$_6$): δ 0.80-0.90 (m, 3H), 1.15-1.40 (m, 6H), 1.65-2.30 (m, 9H), 2.80-2.85 (m, 2H), 3.10-3.55 (m, 7H), 3.75-3.90 (m, 1H), 5.10 (m, 1H), 6.30-6.32 (d, 1H, OH), 6.90-6.95 (m, 1H), 6.95-7.02 (m, 2H), 7.09-7.13 (m, 1H), 7.37-7.39 (m, 1H), 7.40-7.45 (m, 1H).

EXAMPLE 18

(3R)-3-(2-Hydroxy-2-thien-2-ylpent-3-ynoyloxy)-1-(3-phenoxypropyl)-1-azoniabicyclo[2.2.2]octane trifluoroacetate The title compound was obtained as a mixture of diastereomers according to methods d, and b from Intermediate I-19. The yield of the final step was 6.4 mg, 12%.

MS [M-CF$_3$COO]$^+$: 440.

$^1$H-NMR (DMSO-d$_6$): δ 1.60-2.05 (m, 7H), 2.05-2.20 (m, 2H), 2.20-2.35 (m, 1H), 3.10-3.60 (m, 7H), 3.82-3.97 (m, 1H), 3.97-4.10 (m, 2H), 5.13 (m, 1H), 6.90-7.06 (m, 4H), 7.20-7.38 (m, 4H), 7.50-7.56 (m, 1H).

EXAMPLE 19

(3R)-3-(2-Hydroxy-2-thien-2-ylpent-3-ynoyloxy)-1-(3-thien-2-ylpropyl)-1-azoniabicyclo[2.2.2]octane trifluoroacetate The title compound was obtained as a mixture of diastereomers according to methods d, and b from Intermediate I-19. The yield of the final step was 2.4 mg, 4.3%.

MS [M-CF$_3$COO]$^+$: 430

$^1$H-NMR (DMSO-d$_6$): δ 1.60-2.10 (m, 9H), 2.20-2.35 (m, 1H), 2.75-2.90 (m, 2H), 3.10-3.70 (m, 7H), 3.75-3.95 (m, 1H), 5.12 (m, 1H), 6.91-7.04 (m, 3H), 7.19-7.42 (m, 3H), 7.48-7.55 (m, 1H).

EXAMPLE 20

(3R)-3-(2-Hydroxy-2-thien-2-ylbut-3-enoyloxy)-1-(3-phenoxypropyl)-1-azoniabicyclo[2.2.2]octane trifluoroacetate The title compound was obtained as a mixture of diastereomers according to methods d, and b from Intermediate I-20. The yield of the final step was 9.6 mg, 16%.

MS [M-CF$_3$COO]$^+$: 428

$^1$H-NMR (DMSO-d$_6$): δ 1.60-2.05 (m, 4H), 2.05-2.20 (m, 2H), 2.20-2.38 (m, 1H), 3.15-3.60 (m, 7H), 3.82-3.95 (m, 1H), 3.98-4.10 (m, 2H), 5.10-5.20 (m, 1H), 5.25-5.35 (m, 1H), 5.45-5.55 (m, 1H), 6.45-6.55 (m, 1H), 6.75-6.82 (d, 1H, OH), 6.92-6.96 (m, 3H), 6.98-7.03 (m, 1H), 7.13-7.15 (m, 1H), 7.28-7.34 (m, 1H), 7.48-7.52 (m, 1H).

EXAMPLE 21

(3R)-3-(2-Hydroxy-2-thien-2-ylbut-3-enoyloxy)-1-(3-thien-2-ylpropyl)-1-azoniabicyclo[2.2.2]octane trifluoroacetate The title compound was obtained as a mixture of diastereomers according to methods d, and b from Intermediate I-20. The yield of the final step was 5.8 mg, 10%.

MS [M-CF$_3$COO]$^+$: 418

$^1$H-NMR (DMSO-d$_6$): δ 1.60-2.20 (m, 6H), 2.20-2.35 (m, 1H), 2.79-2.84 (m, 2H), 3.10-3.55 (m, 7H), 3.80-3.90 (m, 1H), 5.10-5.20 (m, 1H), 5.25-5.35 (m, 1H), 5.45-5.55 (m, 1H), 6.45-6.55 (m, 1H), 6.75-6.78 (d, 1H, OH), 6.92-6.95 (m, 1H), 6.95-7.05 (m, 2H), 7.10-7.15 (m, 1H), 7.35-7.42 (m, 1H), 7.45-7.52 (m, 1H).

EXAMPLE 22

(3R)-3-[(2S)-2-Cyclopentyl-2-hydroxy-2-thien-2-ylacetoxy]-1-(3-phenoxypropyl)-1-azoniabicyclo[2.2.2]octane bromide The title compound was synthesised according to methods d, and a from the Intermediate I-15a. The yield of the final step was 230 mg, 85%.

MS [M-Br]$^+$: 470, mp: 171° C.

$^1$H-NMR (DMSO-d$_6$): δ 1.27-1.67 (m, 8H), 1.8-2.05 (m, 4H), 2.05-2.20 (m, 2H), 2.25-2.35 (m, 1H), 2.70-2.92 (m, 1H), 3.20-3.25 (m, 1H), 3.25-3.60 (m, 6H), 3.80-3.95 (m, 1H), 3.95-4.08 (m, 2H), 5.10-5.20 (m, 1H), 6.18 (s, 1H, OH), 6.87-7.05 (m, 4H), 7.08-7.20 (m, 1H), 7.25-7.37 (m, 2H), 7.40-7.47 (m, 1H).

EXAMPLE 23

(3R)-3-[(2S)-2-Cyclopentyl-2-hydroxy-2-thien-2-yl-acetoxy]-1-(3-thien-2-ylpropyl)-1-azoniabicyclo[2.2.2]octane trifluoroacetate The title compound was synthesised according to methods d, and b from the Intermediate I-15a. The yield of the final step was 21 mg, 75%.

MS [M-CF$_3$COO]$^+$: 460

$^1$H-NMR (DMSO-d$_6$): δ 1.30-1.65 (m, 8H), 1.80-2.10 (m, 6H), 2.28 (m, 1H), 2.75-2.85 (m, 3H), 3.10-3.55 (m, 7H), 3.80-3.90 (m, 1H), 5.05-5.15 (m, 1H), 6.20 (s, 1H, OH), 6.90-6.95 (m, 1H), 6.95-7.05 (m, 2H), 7.10-7.20 (m, 1H), 7.35-7.45 (m, 2H).

EXAMPLE 24

(3R)-3-[(2S)-2-Cyclopentyl-2-hydroxy-2-thien-2-ylacetoxy]-1-(2-phenoxyethyl)-1-azoniabicyclo[2.2.2]octane bromide The title compound was synthesised according to methods c, and a from the Intermediate I-15a. The yield of the final step was 338 mg, 92%.

MS [M-Br]$^+$: 456; mp: 75° C.

$^1$H-NMR (DMSO-d$_6$): δ 1.25-1.65 (m, 8H), 1.75-2.10 (m, 4H), 2.27-2.35 (m, 1H), 2.70-2.90 (m, 1H), 3.30-3.68 (m, 5H), 3.68-3.83 (m, 2H), 3.92-4.10 (m, 1H), 4.32-4.50 (m, 2H), 5.10-5.20 (m, 1H), 6.20 (s, 1H, OH), 6.90-7.05 (m, 4H), 7.10-7.20 (m, 1H), 7.30-7.42 (m, 3H).

EXAMPLE 25

(3R)-3-[(2S)-2-Cyclopentyl-2-hydroxy-2-thien-2-ylacetoxy]-1-phenethyl-1-azoniabicyclo[2.2.2]octane trifluoroacetate The title compound was synthesised as in Example 23. The yield of the final step was 17 mg, 64%.

MS [M-CF$_3$COO]$^+$: 440

$^1$H-NMR (DMSO-d$_6$): δ 1.30-1.65 (m, 8H), 1.80-2.10 (m, 4H), 2.32 (m, 1H), 2.75-2.85 (m, 1H), 2.95-3.05 (m, 2H), 3.20-3.50 (m, 6H), 3.50-3.65 (m, 1H), 3.85-3.95 (m, 1H), 5.10-5.20 (m, 1H), 6.22 (s, 1H, OH), 6.95-7.05 (m, 1H), 7.10-7.20 (m, 1H), 7.20-7.40 (m, 5H), 7.40-7.55 (m, 1H)

EXAMPLE 26

(3R)-3-[(2S)-2-Cyclopentyl-2-hydroxy-2-thien-2-ylacetoxy]-1-(3-phenylpropyl)-1-azoniabicyclo[2.2.2]octane trifluoroacetate The title compound was synthesised as in Example 23. The yield of the final step was 20 mg, 74%.

MS [M-CF$_3$COO]$^+$: 454

$^1$H-NMR (DMSO-d$_6$): δ 1.30-1.65 (m, 8H), 1.75-2.05 (m, 6H), 2.28 (m, 1H), 2.55-2.65 (m, 2H), 2.75-2.85 (m, 1H), 3.10-3.40 (m, 6H), 3.40-3.55 (m, 1H), 3.77-3.87 (m, 1H), 5.05-5.15 (m, 1H), 6.20 (s, 1H, OH), 6.95-7.0 (m, 1H), 7.10-7.15 (m, 1H), 7.20-7.35 (m, 5H), 7.38-7.42 (m, 1H).

EXAMPLE 27

(3R)-3-[(2S)-2-Cyclopentyl-2-hydroxy-2-thien-2-ylacetoxy]-1-(3-phenylallyl)-1-azoniabicyclo[2.2.2]octane trifluoroacetate The title compound was synthesised as in Example 23. The yield of the final step was 3 mg, 12%.

MS [M-CF$_3$COO]$^+$: 452

$^1$H-NMR (DMSO-d$_6$): δ 1.25-1.60 (m, 8H), 1.80-2.10 (m, 4H), 2.31 (m, 1H), 2.72-2.85 (m, 1H), 3.12-3.22 (m, 1H), 3.22-3.45 (m, 3H), 3.45-3.60 (m, 1H), 3.82-3.92 (m, 1H), 3.95-4.10 (m, 2H), 5.10-5.20 (m, 1H), 6.20 (s, 1H, OH), 6.35-6.50 (m, 1H), 6.82-6.95 (m, 2H), 7.10-7.15 (m, 1H), 7.25-7.47 (m, 4H), 7.55-7.62 (m, 2H).

EXAMPLE 28

(3R)-3-[(2S)-2-Cyclopentyl-2-hydroxy-2-thien-2-ylacetoxy]-1-[3-(4-fluorophenoxy)propyl]-1-azoniabicyclo[2.2.2]octane trifluoroacetate The title compound was synthesised as in Example 23. The yield of the final step was 15 mg, 52%.

MS [M-CF$_3$COO]$^+$: 488

$^1$H-NMR (DMSO-d$_6$): δ 1.25-1.65 (m, 8H), 1.80-2.05 (m, 4H), 2.05-2.17 (m, 2H), 2.30 (m, 1H), 2.75-2.90 (m, 1H), 3.17-3.27 (m, 1H), 3.27-3.60 (m, 6H), 3.82-3.95 (m, 1H), 3.97-4.05 (m, 2H), 5.14 (m, 1H), 6.22 (s, 1H, OH), 6.92-7.05 (m, 3H), 7.10-7.20 (m, 3H), 7.40-7.55 (m, 1H).

EXAMPLE 29

(3R)-3-[(2S)-2-Cyclopentyl-2-hydroxy-2-thien-2-ylacetoxy]-1-(4-oxo-4-thien-2-ylbutyl)-1-azoniabicyclo[2.2.2]octane trifluoroacetate The title compound was synthesised as in Example 23. The yield of the final step was 4 mg, 14%.

MS [M-CF$_3$COO]$^+$: 488

$^1$H-NMR (DMSO-d$_6$): δ 1.25-1.65 (m, 8H), 1.70-2.05 (m, 6H), 2.30 (m, 1H), 2.75-2.90 (m, 1H), 3.05-3.12 (m, 2H), 3.15-3.60 (m, 7H), 3.80-3.92 (m, 1H), 5.13 (m, 1H), 6.22 (s, 1H, OH), 6.98-7.02 (m, 1H), 7.12-7.18 (m, 1H), 7.25-7.30 (m, 1H), 7.40-7.55 (m, 1H), 7.95-8.0 (m, 1H), 8.02-8.07 (m, 1H).

EXAMPLE 30

(3R)-3-[(2S)-2-Cyclopentyl-2-hydroxy-2-thien-2-ylacetoxy]-1-[4-(4-fluorophenyl)-4-oxobutyl]-1-azoniabicyclo[2.2.2]octane trifluoroacetate The title compound was synthesised as in Example 23. The yield of the final step was 9 mg, 29%.

MS [M-CF$_3$COO]$^+$: 500

$^1$H-NMR (DMSO-d$_6$): δ 1.25-1.65 (m, 8H), 1.75-2.05 (m, 6H), 2.30 (m, 1H), 2.75-2.90 (m, 1H), 3.05-3.60 (m, 9H), 3.80-3.95 (m, 1H), 5.14 (m, 1H), 6.22 (s, 1H, OH), 6.98-7.02 (m, 1H), 7.12-7.20 (m, 1H), 7.35-7.45 (m, 3H), 8.02-8.12 (m, 2H).

EXAMPLE 31

(3R)-3-[(2S)-2-Cyclopentyl-2-hydroxy-2-thien-2-ylacetoxy]-1-[3-(3-hydroxyphenoxy)propyl]-1-azoniabicyclo[2.2.2]octane trifluoroacetate The title compound was synthesised as in, Example 23. The yield of the final step was 14 mg, 48%.

MS [M-CF$_3$COO]$^+$: 486

$^1$H-NMR (DMSO-d$_6$): δ 1.25-1.65 (m, 8H), 1.80-2.0 (m, 4H), 2.0-2.20 (m, 2H), 2.30 (m, 1H), 2.75-2.90 (m, 1H), 3.17-3.25 (m, 1H), 3.25-3.60 (m, 6H), 3.82-3.92 (m, 1H), 3.94-4.02 (m, 2H), 5.14 (m, 1H), 6.21 (s, 1H, OH), 6.30-6.42 (m, 3H), 6.95-7.10 (m, 2H), 7.12-7.20 (m, 1H), 7.20-7.45 (m, 1H), 9.47 (s, 1H, OH).

EXAMPLE 32

1-(2-Benzyloxyethyl)-(3R)-3-[(2S)-2-cyclopentyl-2-hydroxy-2-thien-2-ylacetoxy]-1-azoniabicyclo[2.2.2]octane trifluoroacetate The title compound was synthesised as in Example 23. The yield of the final step was 10 mg, 35%.

MS [M-CF$_3$COO]$^+$: 470

$^1$H-NMR (DMSO-d$_6$): δ 1.25-1.62 (m, 8H), 1.80-2.07 (m, 4H), 2.30 (m, 1H), 2.75-2.85 (m, 1H), 3.0-3.65 (m, 7H), 3.75-4.0 (m, 3H), 4.50 (s, 2H), 5.10-5.17 (m, 1H), 6.21 (s, 1H, OH), 6.95-7.0 (m, 1H), 7.10-7.17 (m, 1H), 7.27-7.45 (m, 6H).

EXAMPLE 33

(3R)-3-[(2S)-2-Cyclopentyl-2-hydroxy-2-thien-2-ylacetoxy]-1-(3-o-tolyloxypropyl)-1-azoniabicyclo[2.2.2]octane trifluoroacetate The title compound was synthesised as in Example 23. The yield of the final step was 13 mg, 45%.

MS [M-CF$_3$COO]$^+$: 484

$^1$H-NMR (DMSO-d$_6$): δ 1.23-1.65 (m, 8H), 1.80-2.05 (m, 4H), 2.05-2.20 (m, 5H), 2.31 (m, 1H), 2.75-2.90 (m, 1H), 3.15-3.25 (m, 1H), 3.27-3.60 (m, 6H), 3.85-3.95 (m, 1H), 3.97-4.05 (m, 2H), 5.15 (m, 1H), 6.22 (s, 1H, OH), 6.83-6.93 (m, 2H), 6.98-7.02 (m, 1H), 7.12-7.20 (m, 3H), 7.40-7.46 (m, 1H).

EXAMPLE 34

1-[3-(3-Cyanophenoxy)propyl]-(3R)-3-[(2S)-2-cyclopentyl-2-hydroxy-2-thien-2-ylacetoxy]-1-azoniabicyclo[2.2.2]octane trifluoroacetate The title compound was synthesised as in Example 23. The yield of the final step was 11 mg, 32%.

MS [M-CF$_3$COO]$^+$: 495

$^1$H-NMR (DMSO-d$_6$): δ 1.25-1.65 (m, 8H), 1.75-2.05 (m, 4H), 2.05-2.20 (m, 2H), 2.30 (m, 1H), 2.75-2.90 (m, 1H), 3.20-3.25 (m, 1H), 3.25-3.60 (m, 6H), 3.82-3.95 (m, 1H), 4.05-4.15 (m, 2H), 5.07-5.20 (m, 1H), 6.20 (s, 1H, OH), 6.95-7.05 (m, 1H), 7.12-7.20 (m, 1H), 7.25-7.35 (m, 1H), 7.40-7.57 (m, 4H)

EXAMPLE 35

(3R)-3-[(2S)-2-Cyclopentyl-2-hydroxy-2-thien-2-ylacetoxy]-1-[3-(naphthalen-1-yloxy)propyl]-1-azoniabicyclo[2.2.2]octane trifluoroacetate The title compound was synthesised as in Example 23. The yield of the final step was 10 mg, 26%.

MS [M-CF$_3$COO]$^+$: 520, (described in experimental section, method b).

$^1$H-NMR (DMSO-d$_6$): δ 1.30-1.65 (m, 8H), 1.80-2.10 (m, 4H), 2.20-2.37 (m, 3H), 2.75-2.92 (m, 1H), 3.20-3.65 (m, 7H), 3.90-4.05 (m, 1H), 4.15-4.30 (m, 2H), 5.15-5.22 (m, 1H), 6.24 (s, 1H, OH), 6.95-7.05 (m, 2H), 7.15-7.20 (m, 1H), 7.40-7.60 (m, 5H), 7.85-7.95 (m, 1H), 8.20-8.25 (m, 1H)

EXAMPLE 36

(3R)-3-[(2S)-2-Cyclopentyl-2-hydroxy-2-thien-2-ylacetoxy]-1-[3-(methylphenylamino)propyl]-1-azoniabicyclo[2.2.2]octane trifluoroacetate The title compound was synthesised as in Example 23. The yield of the final step was 12 mg, 35%.

MS [M-CF$_3$COO]$^+$: 483

$^1$H-NMR (DMSO-d$_6$): δ 1.25-1.65 (m, 8H), 1.75-2.02 (m, 6H), 2.28 (m, 1H), 2.75-2.85 (m, 1H), 2.87 (s, 3H), 3.09-3.14 (m, 1H), 3.15-3.55 (m, 8H), 3.75-3.87 (m, 5.05-5.15 (m, 1H), 6.20 (s, 1H, OH), 6.60-6.70 (m, 1H), 6.70-6.77 (m, 2H), 6.92-7.0 (m, 1H), 7.10-7.25 (m, 3H), 7.35-7.45 (m, 1H).

EXAMPLE 37

(3R)-3-[(2S)-2-Cyclopentyl-2-hydroxy-2-thien-2-ylacetoxy]-1-(3-phenylsulfanylpropyl)-1-azoniabicyclo[2.2.2]octane trifluoroacetate The title compound was synthesised as in Example 23. The yield of the final step was 7 mg, 22%.

MS [M-CF$_3$COO]$^+$: 486

$^1$H-NMR (DMSO-d$_6$): δ 1.25-1.65 (m, 8H), 1.75-2.02 (m, 6H), 2.27 (m, 1H), 2.75-2.90 (m, 1H), 2.95-3.05 (m, 2H), 3.07-3.15 (m, 1H), 3.15-3.52 (m, 6H), 3.75-3.87 (m, 1H), 5.05-5.15 (m, 1H), 6.20 (s, 1H, OH), 6.95-7.0 (m, 1H), 7.12-7.17 (m, 1H), 7.20-7.30 (m, 1H), 7.30-7.45 (m, 5H).

EXAMPLE 38

(3R)-3-[(2S)-2-Cyclopentyl-2-hydroxy-2-thien-2-ylacetoxy]-1-(4-oxo-4-phenylbutyl)-1-azoniabicyclo[2.2.2]octane trifluoroacetate The title compound was synthesised as in Example 23. The yield of the final step was 9 mg, 26%.

MS [M-CF$_3$COO]$^+$: 482

$^1$H-NMR (DMSO-d$_6$): δ 1.30-1.67 (m, 8H), 1.72-2.10 (m, 6H), 2.30 (m, 1H), 2.75-2.90 (m, 1H), 3.10-3.60 (m, 9H), 3.85-3.95 (m, 1H), 5.10-5.20 (m, 1H), 6.23 (s, 1H, OH), 6.95-7.05 (m, 1H), 7.12-7.20 (m, 1H), 7.40-7.47 (m, 1H), 7.52-7.60 (m, 2H), 7.62-7.72 (m, 1H), 7.95-8.05 (m, 1H).

EXAMPLE 39

(3R)-3-[(2S)-2-Cyclopentyl-2-hydroxy-2-thien-2-ylacetoxy]-1-[3-(2,4,6-trimethylphenoxy)propyl]-1-azoniabicyclo[2.2.2]octane trifluoroacetate The title compound was synthesised as in Example 23. The yield of the final step was 13 mg, 35%.

MS [M-CF$_3$COO]$^+$: 512

$^1$H-NMR (DMSO-d$_6$): δ 1.30-1.65 (m, 8H), 1.80-2.02 (m, 4H), 2.02-2.25 (m, 11H), 2.32 (m, 1H), 2.75-2.90 (m, 1H), 3.23-3.28 (m, 1H), 3.28-3.62 (m, 6H), 3.65-3.80 (m, 2H), 3.85-3.97 (m, 1H), 5.10-5.20 (m, 1H), 6.22 (s, 1H, OH), 6.82 (s, 2H), 6.97-7.05 (m, 1H), 7.12-7.20 (m, 1H), 7.40-7.47 (m, 1H)

EXAMPLE 40

1-[3-(2-Chlorophenoxy)-propyl]-(3R)-3-[(2S)-2-cyclopentyl-2-hydroxy-2-thien-2-ylacetoxy]-1-azoniabicyclo[2.2.2]octane trifluoroacetate The title compound was synthesised as in Example 23. The yield of the final step was 13 mg, 36%.

MS [M-CF$_3$COO]$^+$: 505

$^1$H-NMR (DMSO-d$_6$): δ 1.30-1.65 (m, 8H), 1.75-2.05 (m, 4H), 2.05-2.25 (m, 2H), 2.31 (m, 1H), 2.75-2.90 (m, 1H), 3.19-3.23 (m, 1H), 3.23-3.62 (m, 6H), 3.85-4.0 (m, 1H), 4.07-4.15 (m, 2H), 5.10-5.20 (m, 1H), 6.22 (s, 1H, OH), 6.92-7.05 (m, 2H), 7.12-7.22 (m, 2H), 7.27-7.37 (m, 1H), 7.40-7.50 (m, 2H).

EXAMPLE 41

(3R)-3-[(2S)-2-Cyclopentyl-2-hydroxy-2-thien-2-ylacetoxy]-1-[3-(3-trifluoromethylphenoxy)propyl]-1-azoniabicyclo[2.2.2]octane trifluoroacetate The title compound was synthesised as in Example 23. The yield of the final step was 13 mg, 33%.

MS [M-CF$_3$COO]$^+$: 538

$^1$H-NMR (DMSO-d$_6$): δ 1.25-1.65 (m, 8H), 1.75-2.05 (m, 4H), 2.05-2.25 (m, 2H), 2.31 (m, 1H), 2.75-2.90 (m, 1H), 3.20-3.25 (m, 1H), 3.25-3.62 (m, 6H), 3.82-3.97 (m, 1H), 4.05-4.20 (m, 2H), 5.10-5.20 (m, 1H), 6.22 (s, 1H, OH), 6.95-7.05 (m, 1H), 7.12-7.20 (m, 1H), 7.22-7.30 (m, 2H), 7.30-7.37 (m, 1H), 7.40-7.47 (m, 1H), 7.50-7.62 (m, 1H).

EXAMPLE 42

1-[3-(Biphenyl-4-yloxy)propyl]-(3R)-3-[(2S)-2-cyclopentyl-2-hydroxy-2-thien-2-ylacetoxy]-1-azoniabicyclo[2.2.2]octane trifluoroacetate The title compound was synthesised as in Example 23. The yield of the final step was 11 mg, 30%.

MS [M-CF$_3$COO]$^+$: 546

$^1$H-NMR (DMSO-d$_6$): δ 1.25-1.65 (m, 8H), 1.77-2.05 (m, 4H), 2.05-2.25 (m, 2H), 2.31 (m, 1H), 2.75-2.92 (m, 1H), 3.20-3.23 (m, 1H), 3.23-3.62 (m, 6H), 3.85-3.97 (m, 1H), 4.05-4.15 (m, 2H), 5.10-5.20 (m, 1H), 6.22 (s, 1H, OH), 6.95-7.10 (m, 3H), 7.12-7.20 (m, 1H), 7.27-7.37 (m, 1H), 7.40-7.50 (m, 3H), 7.55-7.70 (m, 4H).

EXAMPLE 43

(3R)-3-[(2S)-2-Cyclopentyl-2-hydroxy-2-thien-2-ylacetoxy]-1-[3-(2,4-difluorophenoxy)propyl]-1-azoniabicyclo[2.2.2]octane trifluoroacetate The title compound was synthesised as in Example 23. The yield of the final step was 10 mg, 28%.

MS [M-CF$_3$COO]$^+$: 506

$^1$H-NMR (DMSO-d$_6$): δ 1.25-1.65 (m, 8H), 1.75-2.05 (m, 4H), 2.05-2.15 (m, 2H), 2.30 (m, 1H), 2.82 (m, 1H), 3.17-3.28 (m, 1H), 3.28-3.47 (m, 5H), 3.47-3.60 (m, 1H), 3.82-3.95 (m, 1H), 4.05-4.15 (m, 2H), 5.14 (m, 1H), 6.22 (s, 1H, OH), 6.95-7.10 (m, 2H), 7.12-7.38 (m, 3H), 7.40-7.45 (m, 1H).

EXAMPLE 44

(3R)-3-[(2S)-2-Cyclopentyl-2-hydroxy-2-thien-2-ylacetoxy]-1-[3-(4-methoxyphenoxy)propyl]-1-azoniabicyclo[2.2.2]octane trifluoroacetate The title compound was synthesised as in Example 23. The yield of the final step was 11 mg, 32%.

MS [M-CF$_3$COO]$^+$: 500

$^1$H-NMR (DMSO-d$_6$): δ 1.25-1.65 (m, 8H), 1.75-2.15 (m, 6H), 2.30 (m, 1H), 2.82 (m, 1H), 3.18-3.25 (m, 1H), 3.25-3.45 (m, 5H), 3.45-3.60 (m, 1H), 3.70 (s, 3H), 3.82-3.92 (m, 1H), 3.92-4.02 (m, 2H), 5.14 (m, 1H), 6.22 (s, 1H, OH), 6.88 (m, 4H), 6.98-7.02 (m, 1H), 7.15-7.16 (m, 1H), 7.42-7.44 (m, 1H).

EXAMPLE 45

(3R)-3-[(2S)-2-Cyclopentyl-2-hydroxy-2-thien-2-ylacetoxy]-1-[3-(5,6,7,8-tetrahydronaphthalen-2-yloxy)propyl]-1-azoniabicyclo[2.2.2]octane trifluoroacetate The title compound was synthesised as in Example 23. The yield of the final step was 14 mg, 38%.

MS [M-CF$_3$COO]$^+$: 524

$^1$H-NMR (DMSO-d$_6$): δ 1.30-1.65 (m, 8H), 1.65-1.75 (m, 4H), 1.75-2.20 (m, 6H), 2.30 (m, 1H), 2.50-2.70 (m, 4H), 2.75-2.95 (m, 1H), 3.17-3.25 (m, 1H), 3.25-3.45 (m, 5H), 3.45-3.60 (m, 1H), 3.80-3.92 (m, 1H), 3.92-4.02 (m, 2H), 5.14 (m, 1H), 6.22 (s, 1H, OH), 6.60-6.70 (m, 2H), 6.95-7.02 (m, 2H), 7.15-7.20 (m, 1H), 7.42-7.45 (m, 1H).

EXAMPLE 46

1-[3-(Benzo[1,3]dioxol-5-yloxy)propyl]-(3R)-3-[(2S)-2-cyclopentyl-2-hydroxy-2-thien-2-ylacetoxy]-1-azoniabicyclo[2.2.2]octane trifluoroacetate The title compound was synthesised as in Example 23. The yield of the final step was 13 mg, 38%.

MS [M-CF$_3$COO]$^+$: 514

$^1$H-NMR (DMSO-d$_6$): δ 1.25-1.65 (m, 8H), 1.75-2.15 (m, 6H), 2.30 (m, 1H), 2.75-2.90 (m, 1H), 3.15-3.25 (m, 1H), 3.25-3.42 (m, 5H), 3.42-3.60 (m, 1H), 3.82-3.92 (m, 1H), 3.92-4.0 (m, 2H), 5.13 (m, 1H), 5.97 (s, 2H), 6.20 (s, 1H, OH), 6.36-6.40 (m, 1H), 6.64-6.65 (m, 1H), 6.81-6.84 (m, 1H), 6.98-7.02 (m, 1H), 7.15-7.17 (m, 1H), 7.42-7.44 (m, 1H).

EXAMPLE 47

1-[3-(2-Carbamoyl-phenoxy)-propyl]-(3R)-3-[(2S)-2-cyclopentyl-2-hydroxy-2-thien-2-yl-acetoxy]-1-azoniabicyclo[2.2.2]octane trifluoroacetate The title compound was synthesised as in Example 23. The yield of the final step was 13 mg, 36%.

MS [M-CF$_3$COO]$^+$: 513

$^1$H-NMR (DMSO-d$_6$): δ 1.27. 1.65 (m, 8H), 1.80-2.07 (m, 4H), 2.12-2.27 (m, 2H), 2.31 (m, 1H), 2.82 (m, 1H), 3.17-3.25 (m, 1H), 3.25-3.45 (m, 5H), 3.45-3.60 (m, 1H), 3.82-3.92 (m, 1H), 4.10-4.17 (m, 2H), 5.15 (m, 1H), 6.23 (s, 1H, OH), 6.98-7.16 (m, 4H), 7.42-7.50 (m, 2H), 7.50-7.55 (bs, 2H), 7.68-7.72 (m, 1H).

EXAMPLE 48

(3R)-3-[(2S)-2-Cyclopentyl-2-hydroxy-2-thien-2-ylacetoxy]-1-[3-(3-dimethylaminophenoxy)propyl]-1-azoniabicyclo[2.2.2]octane trifluoroacetate The title compound was synthesised as in Example 23. The yield of the final step was 14 mg, 40%.

MS [M-CF$_3$COO]$^+$: 513

$^1$H-NMR (DMSO-d$_6$): δ 1.25-1.65 (m, 8H), 1.70-2.20 (m, 6H), 2.30 (m, 1H), 2.75-2.95 (m, 7H), 3.15-3.65 (m, 7H), 3.80-4.05 (m, 3H), 5.14 (m, 1H), 6.15-6.30 (m, 3H), 6.32-6.36 (m, 1H), 6.95-7.22 (m, 3H), 7.40-7.45 (m, 1H).

EXAMPLE 49

1-[3-(4-Acetylaminophenoxy)propyl]-(3R)-3-[(2S)-2-cyclopentyl-2-hydroxy-2-thien-2-ylacetoxy]-1-azoniabicyclo[2.2.2]octane trifluoroacetate The title compound was synthesised as in Example 23. The yield of the final step was 12 mg, 34%.

MS [M-CF$_3$COO]$^+$: 527

$^1$H-NMR (DMSO-d$_6$): δ 1.25-1.65 (m. 8H), 1.75-2.20 (m, 9H), 2.30 (m, 1H), 2.82 (m, 1H), 3.17-3.28 (m, 1H), 3.28-3.45 (m, 5H), 3.45-3.60 (m, 1H), 3.84-3.92 (m, 1H), 3.96-4.02 (m, 2H), 5.13 (m, 1H), 6.22 (s, 1H, OH), 6.86-6.90 (m, 2H), 6.98-7.02 (m, 1H), 7.15-7.17 (m, 1H), 7.42-7.44 (m, 1H), 7.48-7.52 (m, 2H), 9.85 (s, 1H, NH(CO)).

EXAMPLE 50

(3R)-3-[(2S)-2-Cyclopentyl-2-hydroxy-2-thien-2-ylacetoxy]-1-[3-(4-methoxycarbonylphenoxy)propyl]-1-azoniabicyclo[2.2.2]octane trifluoroacetate The title compound was synthesised as in Example 23. The yield of the final step was 14 mg, 37%.

MS [M-CF$_3$COO]$^+$: 528

$^1$H-NMR (DMSO-d$_6$): δ 1.25-1.65 (m, 8H), 1.80-2.05 (m, 4H), 2.05-2.25 (m, 2H), 2.31 (m, 1H), 2.82 (m, 1H), 3.17-3.28 (m, 1H), 3.28-3.45 (m, 5H), 3.45-3.60 (m, 1H), 3.82 (s, 3H), 3.82-3.95 (m, 1H), 4.10-4.15 (m, 2H), 5.14 (m, 1H), 6.22 (s, 1H, OH), 6.95-7.10 (m, 3H), 7.15-7.17 (m, 1H), 7.43-7.45 (m, 1H), 7.92-7.97 (m, 2H).

EXAMPLE 51

(3R)-3-[(2S)-2-Cyclopentyl-2-hydroxy-2-thien-2-ylacetoxy]-1-[3-(4-nitrophenoxy)propyl]-1-azoniabicyclo[2.2.2]octane trifluoroacetate The title compound was synthesised as in Example 23. The yield of the final step was 15 mg, 41%.

MS [M-CF$_3$COO]$^+$: 515

$^1$H-NMR (DMSO-d$_6$): δ 1.27-1.65 (m, 8H), 1.77-2.07 (m, 4H), 2.10-2.27 (m, 2H), 2.31 (m, 1H), 2.82 (m, 1H), 3.17-3.28 (m, 1H), 3.28-3.45 (m, 5H), 3.45-3.60 (m, 1H), 3.85-3.95 (m, 1H), 4.15-4.25 (m, 2H), 5.15 (m, 1H), 6.22 (s, 1H, OH), 6.97-7.02 (m, 1H), 7.14-7.18 (m, 3H), 7.42-7.45 (m, 1H), 8.22-8.27 (m, 2H).

EXAMPLE 52

(3R)-3-[(2S)-2-Cyclopentyl-2-hydroxy-2-thien-2-ylacetoxy]-1-[3-(4-hydroxymethylphenoxy)propyl]-1-azoniabicyclo[2.2.2]octane trifluoroacetate The title compound was synthesised as in Example 23. The yield of the final step was 13 mg, 36%.

MS [M-CF$_3$COO]$^+$: 500

$^1$H-NMR (DMSO-d$_6$): δ 1.25-1.65 (m, 8H), 1.77-2.05 (m, 4H), 2.05-2.20 (m, 2H), 2.30 (m, 1H), 2.82 (m, 1H), 3.17-3.60 (m, 7H), 3.82-3.95 (m, 1H), 3.95-4.05 (m, 2H), 4.35-4.45 (m, 2H), 5.05-5.11 (t, 1H, OH), 5.11-5.20 (m, 1H), 6.22 (s, 1H, OH), 6.86-6.95 (m, 2H), 6.95-7.05 (m, 1H), 7.15-7.17 (m, 1H), 7.22-7.26 (m, 2H), 7.42-7.44 (m, 1H).

EXAMPLE 53

(3R)-3-[(2R)-2-cyclopentyl-2-hydroxy-2-thien-2-ylacetoxy]-1-(3-phenoxypropyl)-1-azoniabicyclo[2.2.2]octane bromide The title compound was synthesised according to methods d, and a from the Intermediate I-15b. The yield of the final step was 1.2 g (73%).

mp: 181° C. MS: [M-Br]$^+$: 470.

$^1$H-NMR (DMSO-d$_6$): δ 1.30-1.70 (m, 8H), 1.70-1.80 (m, 2H), 1.80-2.05 (m, 2H), 2.05-2.30 (m, 3H), 2.80-2.95 (m, 1H), 3.25-3.62 (m, 7H), 3.87-4.0 (m, 1H), 4.0-4.10 (m, 2H), 5.10-5.20 (m, 1H), 6.20 (s, 1H, OH), 6.95-7.05 (m, 4H), 7.15-7.25 (m, 1H), 7.25-7.37 (m, 2H), 7.42-7.45 (m, 1H).

EXAMPLE 54

(3R)-3-[(2R)-2-Cyclopentyl-2-hydroxy-2-thien-2-ylacetoxy]-1-(3-thien-2-ylpropyl)-1-azoniabicyclo[2.2.2]octane trifluoroacetate The title compound was synthesised according to methods d, and b from the Intermediate I-15b. The yield of the final step was 15 mg (54%).

MS [M-CF$_3$COO]$^+$: 460

$^1$H-NMR (DMSO-d$_6$): δ 1.30-1.65 (m 8H), 1.65-1.80 (m, 2H), 1.80-2.10 (m, 4H), 2.21 (m, 1H), 2.77-2.90 (m, 3H), 3.15-3.40 (m, 6H), 3.40-3.55 (m, 1H), 3.80-3.92 (m, 1H), 5.05-5.18 (m, 1H), 6.20 (s, 1H, OH), 6.92-6.96 (m, 1H), 6.96-7.02 (m, 2H), 7.12-7.20 (m, 1H), 7.36-7.40 (m, 1H), 7.40-7.46 (m, 1H)

EXAMPLE 55

(3R)-3-[(2R)-2-Cyclopentyl-2-hydroxy-2-thien-2-ylacetoxy]-1-(2-phenoxyethyl)-1-azoniabicyclo[2.2.2]octane trifluoroacetate The title compound was synthesised as in Example 54. The yield of the final step was 16 mg, 58%.

MS [M-CF$_3$COO]$^+$: 456.

$^1$H-NMR (DMSO-d$_6$): δ 1.30-1.65 (m, 8H), 1.75-1.85 (m, 2H), 1.85-2.05 (m, 2H), 2.23 (m, 1H), 2.75-2.90 (m, 1H), 3.40-3.57 (m, 4H), 3.57-3.70 (m, 1H), 3.70-3.80 (m, 2H), 3.97-4.10 (m, 1H), 4.37-4.47 (m, 2H), 5.10-5.18 (m, 1H), 6.20 (s, 1H, OH), 6.92-7.05 (m, 4H), 7.10-7.18 (m, 1H), 7.30-7.38 (m, 2H), 7.38-7.44 (m, 1H).

EXAMPLE 56

(3R)-3-[(2R)-2-Cyclopentyl-2-hydroxy-2-thien-2-ylacetoxy]-1-phenethyl-1-azoniabicyclo[2.2.2]octane trifluoroacetate The title compound was synthesised as in Example 54. The yield of the final step was 13 mg, 50%.

MS [M-CF$_3$COO]$^+$: 440.

$^1$H-NMR (DMSO-d$_6$): δ 1.35-1.65 (m, 8H), 1.65-1.85 (m, 2H), 1.85-2.05 (m, 2H), 2.25 (m, 1H), 2.85-2.92 (m, 1H), 2.95-3.10 (m, 2H), 3.30-3.50 (m, 6H), 3.50-3.65 (m, 1H), 3.85-4.0 (m, 1H), 5.12-5.20 (m, 1H), 6.21 (s, 1H, OH), 6.95-7.05 (m, 1H), 7.15-7.20 (m, 1H), 7.25-7.40 (m, 5H), 7.40-7.47 (m, 1H).

EXAMPLE 57

(3R)-3-[(2R)-2-Cyclopentyl-2-hydroxy-2-thien-2-ylacetoxy]-1-(3-phenylpropyl)-1-azoniabicyclo[2.2.2]octane trifluoroacetate The title compound was synthesised as in Example 54. The yield of the final step was 14 mg, 53%.

MS [M-CF$_3$COO]$^+$: 454.

$^1$H-NMR (DMSO-d$_6$): δ 1.30-1.65 (m, 8H), 1.65-1.77 (m, 2H), 1.77-2.05 (m, 4H), 2.21 (s, 1H), 2.55-2.65 (m, 2H), 2.75-2.92 (m, 1H), 3.15-3.40 (m, 6H), 3.40-3.55 (m, 1H), 3.80-3.90 (m, 1H), 5.06-5.16 (m, 1H), 6.19 (s, 1H, OH), 6.95-7.02 (m, 1H), 7.12-7.18 (m, 1H), 7.20-7.36 (m, 5H), 7.38-7.46 (m, 1H).

EXAMPLE 58

(3R)-3-[(2R)-2-Cyclopentyl-2-hydroxy-2-thien-2-ylacetoxy]-1-(3-phenylallyl)-1-azoniabicyclo[2.2.2]octane trifluoroacetate The title compound was synthesised as in Example 54. The yield of the final step was 7 mg, 26%.

MS [M-CF$_3$COO]$^+$: 452.

$^1$H-NMR (DMSO-d$_6$): δ 1.30-1.65 (m, 8H), 1.75-2.05 (m, 4H), 2.24 (m, 1H), 2.75-2.90 (m, 1H), 3.25-3.45 (m, 4H), 3.45-3.55 (m, 1H), 3.72-3.95 (m, 1H), 4.0-4.15 (m, 2H), 5.10-5.17 (m, 1H), 6.19 (s, 1H, OH), 6.40-6.55 (m, 1H), 6.82-6.70 (m, 2H), 7.12-7.17 (m, 1H), 7.30-7.45 (m, 4H), 7.55-7.62 (m, 2H)

EXAMPLE 59

(3R)-3-[(2R)-2-Cyclopentyl-2-hydroxy-2-thien-2-ylacetoxy]-1-[3-(4-fluorophenoxy)propyl]-1-azoniabicyclo[2.2.2]octane trifluoroacetate The title compound was synthesised as in Example 54. The yield of the final step was 19 mg, 64%.

MS [M-CF$_3$COO]$^+$: 488.

$^1$H-NMR (DMSO-d$_6$): δ 1.30-1.65 (m, 8H), 1.65-1.80 (m, 2H), 1.80-2.05 (m, 2H), 2.05-2.20 (m, 2H), 2.23 (m, 1H), 2.80-2.95 (m, 1H), 3.20-3.60 (m, 7H), 3.85-3.95 (m, 1H), 3.97-4.07 (m, 2H), 5.14 (m, 1H), 6.20 (s, 1H, OH), 6.90-7.05 (m, 3H), 7.10-7.20 (m, 3H), 7.40-7.47 (m, 1H).

EXAMPLE 60

(3R)-3-[(2S)-2-Cyclopentyl-2-fur-2-yl-2-hydroxyacetoxy]-1-(3-phenoxypropyl)-1-azoniabicyclo[2.2.2]octane trifluoroacetate The title compound was synthesised according to methods d, and b from Intermediate I-14a The yield of the final step was 4 mg, 15%.

MS [M-CF$_3$COO]$^+$: 454

$^1$H-NMR (DMSO-d$_6$): δ 1.45-1.67 (m, 9H), 1.67-1.80 (m, 1H), 1.80-2.05 (m, 2H), 2.05-2.22 (m, 3H), 2.85-2.95 (m, 1H), 3.20-3.55 (m, 7H), 3.85-3.95 (m, 1H), 4.0-4.10 (m, 2H), 5.10-5.20 (m, 1H), 6.03 (s, 1H), 6.40-6.45 (m, 2H), 6.90-7.0 (m, 3H), 7.27-7.35 (m, 2H), 7.62 (m, 1H)

EXAMPLE 61

(3R)-3-[(2S)-2-Cyclopentyl-2-fur-2-yl-2-hydroxyacetoxy]-1-(3-thien-2-ylpropyl)-1-azoniabicyclo[2.2.2]octane trifluoroacetate The title compound was synthesised as in Example 60. The yield of the final step was 2 mg, 7%.

MS [M-CF$_3$COO]$^+$: 444

$^1$H-NMR (DMSO-d$_6$): δ 1.40-1.66 (m, 9H), 1.66-2.10 (m, 5H), 2.17 (m, 1H), 2.78-2.90 (m, 3H), 3.14-3.50 (m, 7H), 3.80-3.90 (m, 1H), 5.10-5.18 (m, 1H), 6.02 (s, 1H), 6.38-6.46 (m, 2H), 6.92-7.02 (m, 2H), 7.36-7.40 (m, 1H), 7.60 (m, 1H).

EXAMPLE 62

(3R)-3-[(2S)-2-Cyclopentyl-2-fur-2-yl-2-hydroxyacetoxy]-1-phenethyl-1-azoniabicyclo[2.2.2]octane trifluoroacetate The title compound was synthesised as in Example 60. The yield of the final step was 4 mg, 17%.

MS [M-CF$_3$COO]$^+$: 424

$^1$H-NMR (DMSO-d$_6$): δ 1.40-2.05 (m, 12H), 2.20 (m, 1H), 2.88 (m, 1H), 2.95-3.05 (m, 2H), 3.20-3.60 (m, 7H), 3.85-3.95 (m, 1H), 5.18 (m, 1H), 6.03 (s, 1H, OH), 6.40-6.45 (m, 2H), 7.25-7.40 (m, 5H), 7.62 (m, 1H).

EXAMPLE 63

(3R)-3-[(2S)-2-Cyclopentyl-2-fur-2-yl-2-hydroxyacetoxy]-1-(3-phenylpropyl)-1-azoniabicyclo[2.2.2]octane trifluoroacetate The title compound was synthesised as in Example 60. The yield of the final step was 10 mg, 36.2%.

MS [M-CF$_3$COO]$^+$: 438

$^1$H-NMR (DMSO-d$_6$): δ 1.35-2.05 (m, 14H), 2.16 (m, 1H), 2.55-2.65 (m, 2H), 2.75-2.95 (m, 1H), 3.10-3.55 (m, 7H), 3.77-3.92 (m, 1H), 5.05-5.15 (m, 1H), 6.02 (s, 1H, OH), 6.35-6.45 (m, 2H), 7.17-7.40 (m, 5H), 7.60 (m, 1H).

EXAMPLE 64

(3R)-3-[(2R)-2-Cyclopentyl-2-fur-2-yl-2-hydroxyacetoxy]-1-(3-phenoxypropyl)-1-azoniabicyclo[2.2.2]octane trifluoroacetate The title compound was synthesised according to methods d, and b from Intermediate I-14b. The yield of the final step was 12 mg, 46%.

MS [M-CF$_3$COO]$^+$: 454

$^1$H-NMR (DMSO-d$_6$): δ 1.40-1.60 (m, 8H), 1.75-2.05 (m, 4H), 2.05-2.20 (m, 2H), 2.30 (m, 1H), 2.75-2.87 (m, 1H), 3.10-3.60 (m, 7H), 3.85-3.95 (m, 1H), 3.97-4.07 (m, 2H), 5.10-5.17 (m, 1H), 6.04 (s, 1H), 6.40-6.50 (m, 2H), 6.90-7.0 (m, 3H), 7.27-7.37 (m, 2H), 7.60-7.65 (m, 1H).

EXAMPLE 65

(3R)-3-[(2R)-2-Cyclopentyl-2-fur-2-yl-2-hydroxyacetoxy]-1-(3-thien-2-ylpropyl)-1-azoniabicyclo[2.2.2]octane trifluoroacetate The title compound was synthesised as in Example 64. The yield of the final step was 14 mg, 55%.

MS [M-CF$_3$COO]$^+$: 444

$^1$H-NMR (DMSO-d$_6$): δ 1.40-1.65 (m, 8H), 1.75-2.10 (m, 6H), 2.27 (m, 1H), 2.70-2.90 (m, 3H), 3.0-3.55 (m, 7H), 3.77-3.82 (m, 1H), 5.05-5.15 (m, 1H), 6.03 (s, 1H), 6.40-6.45 (m, 2H), 6.90-7.05 (m, 2H), 7.35-7.42 (m, 1H), 7.55-7.65 (m, 1H).

EXAMPLE 66

(3R)-3-[(2R)-2-Cyclopentyl-2-fur-2-yl-2-hydroxyacetoxy]-1-phenethyl-1-azoniabicyclo[2.2.2]octane trifluoroacetate The title compound was synthesised as in Example 64. The yield of the final step was 15 mg, 57%.

MS [M-CF$_3$COO]$^+$: 424

$^1$H-NMR (DMSO-d$_6$): δ 1.30-2.40 (m, 13H), 2.75-2.85 (m, 1H), 2.95-3.05 (m, 2H), 3.10-3.75 (m, 7H), 3.85-4.0 (m, 1H), 5.05-5.15 (m, 1H), 6.02 (s, 1H, OH), 6.44 (m, 2H), 7.20-7.40 (m, 5H), 7.63 (m, 1H).

EXAMPLE 67

(3R)-3-[(2R)-2-Cyclopentyl-2-fur-2-yl-2-hydroxyacetoxy]-1-(3-phenylpropyl)-1-azoniabicyclo[2.2.2]octane trifluoroacetate The title compound was synthesised as in Example 64. The yield of the final step was 10 mg, 38%.

MS [M-CF$_3$COO]$^+$: 438

$^1$H-NMR (DMSO-d$_6$): δ 1.40-1.60 (m, 8H), 1.75-2.05 (m, 6H), 2.27 (m, 1H), 2.55-2.60 (m, 2H), 2.79 (m, 1H), 3.04-3.10 (m, 1H), 3.12-3.40 (m, 5H), 3.40-3.52 (m, 1H), 3.80-3.90 (m, 1H), 5.10 (m, 1H), 6.02 (s, 1H, OH), 6.40 (m, 2H), 7.20-7.35 (m, 5H), 7.58 (m, 1H)

EXAMPLE 68

(3R)-3-[(2R)-2-Cyclohexyl-2-hydroxy-2-phenylacetoxy]-1-(3-phenoxypropyl)-1-azoniabicyclo[2.2.2]octane trifluoroacetate The title compound was synthesised according to methods d, and b from the Intermediate I-16a. The yield of the final step was 28 mg, 1100%.

MS [M-CF$_3$COO]$^+$: 478.

$^1$H-NMR (DMSO-d$_6$): δ 0.95-1.18 (m, 4H), 1.18-1.65 (m, 5H), 1.70-2.05 (m, 5H), 2.05-2.17 (m, 2H), 2.17-2.30 (m, 2H), 3.15-3.25 (m, 1H), 3.25-3.55 (m, 6H), 3.75-3.90 (m, 1H), 3.95-4.07 (m, 2H), 5.05-5.15 (m, 1H), 5.78 (s, 1H, OH), 6.90-7.0 (m, 3H), 7.25-7.45 (m, 5H), 7.55-7.65 (m, 2H).

EXAMPLE 69

(3R)-3-[(2R)-2-Cyclohexyl-2-hydroxy-2-phenylacetoxy]-1-(3-thien-2-ylpropyl)-1-azoniabicyclo[2.2.2]octane trifluoroacetate The title compound was synthesised as in Example 68. The yield of the final step was 22 mg, 78%.

MS [M-CF$_3$COO]$^+$: 468.

$^1$H-NMR (DMSO-d$_6$): δ 0.95-1.18 (m, 4H), 1.18-1.65 (m, 5H), 1.70-2.0 (m, 7H), 2.20 (m, 2H), 2.75-2.85 (m, 2H), 3.05-3.15 (m, 1H), 3.15-3.50 (m, 6H), 3.70-3.85 (m, 1H), 5.05-5.15 (m, 1H), 5.76 (s, 1H, OH), 6.90-7.05 (m, 2H), 7.20-7.45 (m, 4H), 7.55-7.65 (m, 2H)

EXAMPLE 70

(3R)-3-[(2R)-2-Cyclohexyl-2-hydroxy-2-phenylacetoxy]-1-phenethyl-1-azoniabicyclo[2.2.2]octane trifluoroacetate The title compound was synthesised as in Example 68. The yield of the final step was 14 mg, 50%.

MS [M-CF$_3$COO]$^+$: 448.

$^1$H-NMR (DMSO-d$_6$): δ 0.97-1.15 (m, 3H), 1.15-2.05 (m, 1H), 2.15-2.30 (m, 2H), 2.90-3.05 (m, 2H), 3.20-3.30 (m, 1H), 3.30-3.50 (m, 5H), 3.50-3.62 (m, 1H), 3.82-3.92 (m, 1H), 5.16 (m, 1H), 5.78 (s, 1H, OH), 7.25-7.45 (m, 8H), 7.58-7.64 (m, 2H).

EXAMPLE 71

(3R)-3-[(2S)-2-Cyclohexyl-2-hydroxy-2-phenylacetoxy]-1-(3-phenoxypropyl)-1-azoniabicyclo[2.2.2]octane trifluoroacetate The title compound was synthesised according to methods d, and b from the Intermediate I-16b. The yield of the final step was 18 mg, 63%.

MS [M-CF$_3$COO]$^+$: 478.

$^1$H-NMR (DMSO-d$_6$): δ 0.95-1.17 (m, 4H), 1.20-2.0 (m, 10H), 2.02-2.35 (m, 4H), 3.15-3.55 (m, 7H), 3.80-3.90 (m, 1H), 3.97-4.10 (m, 2H), 5.05-5.15 (m, 1H), 5.75 (s, 1H, OH), 6.90-7.02 (m, 3H), 7.25-7.45 (m, 5H), 7.57-7.67 (m, 2H)

EXAMPLE 72

(3R)-3-[(2S)-2-Cyclohexyl-2-hydroxy-2-phenylacetoxy]-1-(3-thien-2-ylpropyl)-1-azoniabicyclo[2.2.2]octane trifluoroacetate The title compound was synthesised as in Example 71. The yield of the final step was 19 mg, 66%.

MS [M-CF$_3$COO]$^+$: 468.

$^1$H-NMR (DMSO-d$_6$): δ 0.95-1.17 (m, 4H), 1.20-2.10 (m, 12H), 2.15-2.35 (m, 2H), 2.75-2.97 (m, 2H), 3.10-3.37 (m, 6H), 3.37-3.55 (m, 1H), 3.75-3.87 (m, 1H), 5.05-5.12 (m, 1H), 5.74 (s, 1H, OH), 6.90-7.05 (m, 2H), 7.22-7.45 (m, 4H), 7.55-7.67 (m, 2H).

EXAMPLE 73

(3R)-3-[(2S)-2-Cyclohexyl-2-hydroxy-2-phenylacetoxy]-1-phenethyl-1-azoniabicyclo[2.2.2]octane trifluoroacetate The title compound was synthesised as in Example 71. The yield of the final step was 16 mg, 58%.

MS [M-CF$_3$COO]$^+$: 448.

$^1$H-NMR (DMSO-d$_6$): δ 0.98-1.15 (m, 3H), 1.20-2.05 (m, 11H), 2.20-2.35 (m, 2H), 2.90-3.10 (m, 2H), 3.20-3.50 (m, 6H), 3.50-3.60 (m, 1H), 3.80-3.92 (m, 1H), 5.12 (m, 1H), 5.75 (s, 1H, OH), 7.25-7.40 (m, 8H), 7.60-7.65 (m, 1H).

EXAMPLE 74

(3R)-3-[(2S)-2-Cyclohexyl-2-fur-2-yl-2-hydroxyacetoxy]-1-(3-phenoxypropyl)-1-azoniabicyclo[2.2.2]octane trifluoroacetate The title compound was synthesised according to methods c, and b from the intermediate I-4a. The yield of the final step was 3.8 mg, 6.2%.

MS [M-CF$_3$COO]$^+$: 468.

$^1$H-NMR (DMSO-d$_6$): δ 1.0-1.50 (m, 7H), 1.50-2.05 (m, 7H), 2.05-2.35 (m, 4H), 3.15-3.65 (m, 7H), 3.82-3.95 (m, 1H), 4.0-4.1 (m, 2H), 5.16 (m, 1H), 5.99 (s, 1H, OH), 6.40-6.45 (m, 2H), 6.90-7.0 (m, 3H), 7.25-7.35 (m, 2H), 7.64 (m, 1H).

EXAMPLE 75

(3R)-3-[(2S)-2-Cyclohexyl-2-fur-2-yl-2-hydroxyacetoxy]-1-(3-thien-2-ylpropyl)-1-azoniabicyclo[2.2.2]octane trifluoroacetate The title compound was synthesised as in Example 74. The yield of the final step was 3.6 mg, 6%.

MS [M-CF$_3$COO]$^+$: 458.

$^1$H-NMR (DMSO-d$_6$): δ 1.0-1.45 (m, 7H), 1.50-2.10 (m, 9H), 2.15-2.30 (m, 2H), 2.75-2.90 (m, 2H), 3.10-3.55 (m, 7H), 3.77-3.92 (m, 1H), 5.13 (m, 1H), 5.98 (s, 1H, OH), 6.36-6.46 (m, 2H), 6.92-7.02 (m, 2H), 7.36-7.40 (m, 1H), 7.62 (m, 1H).

EXAMPLE 76

(3R)-3-[(2S)-2-Cyclohexyl-2-fur-2-yl-2-hydroxyacetoxy]-1-phenethyl-1-azoniabicyclo[2.2.2]octane trifluoroacetate The title compound was synthesised as in Example 74. The yield of the final step was 2.4 mg, 4.2%.

MS [M-CF$_3$COO]$^+$: 438.

$^1$H-NMR (DMSO-d$_6$): δ 1.0-1.45 (m, 7H), 1.50-2.05 (m, 7H), 2.20-2.35 (m, 2H), 2.92-3.15 (m, 2H), 3.20-3.65 (m, 7H), 3.85-3.95 (m, 1H), 5.18 (m, 1H), 6.0 (s, 6.37-6.47 (m, 2H), 7.25-7.45 (m, 5H), 7.64 (m, 1H).

EXAMPLE 77

(3R)-3-[(2S)-2-Cyclohexyl-2-fur-2-yl-2-hydroxyacetoxy]-1-(3-phenylpropyl)-1-azoniabicyclo[2.2.2]octane trifluoroacetate The title compound was synthesised as in Example 74. The yield of the final step was 2.8 mg, 4.8%.

MS [M-CF$_3$COO]$^+$: 452.

¹H-NMR (DMSO-d₆): δ 0.95-1.50 (m, 7H), 1.50-2.10 (m, 9H), 2.15-2.32 (m, 2H), 2.55-2.65 (m, 2H), 3.10-3.60 (m, 7H), 3.77-3.80 (m, 1H), 5.12 (m, 1H), 5.98 (s, 1H, OH), 6.36-6.46 (m, 2H), 7.18-7.40 (m, 5H), 7.62 (m, 1H).

EXAMPLE 78

(3R)-3-[(2R)-2-Cyclohexyl-2-fur-2-yl-2-hydroxyacetoxy]-1-(3-phenoxypropyl)-1-azoniabicyclo[2.2.2]octane trifluoroacetate The title compound was synthesised according to methods c, and b from the Intermediate I-4b. The yield of the final step was 3.0 mg, 5%.

MS [M-CF₃COO]⁺: 468.

¹H-NMR (DMSO-d₆): δ 1.0-1.45 (m, 7H), 1.55-1.75 (m, 3H), 1.80-2.05 (m, 4H), 2.05-2.25 (m, 3H), 2.30 (m, 1H), 3.10-3.20 (m, 1H), 3.20-3.60 (m, 6H), 3.85-3.95 (m, 1H), 3.95-4.10 (m, 2H), 5.16 (m, 1H), 5.99 (s. 1H, OH), 6.40-6.50 (m, 2H), 6.90-7.0 (m, 3H), 7.25-7.38 (m, 2H), 7.64 (m, 1H).

EXAMPLE 79

(3R)-3-[(2R)-2-Cyclohexyl-2-fur-2-yl-2-hydroxyacetoxy]-1-(3-thien-2-ylpropyl)-1-azoniabicyclo[2.2.2]octane trifluoroacetate The title compound was synthesised as in Example 78. The yield of the final step was 9.1 mg, 33.1%.

MS [M-CF₃COO]⁺: 458.

¹H-NMR (DMSO-d₆): δ 0.95-1.55 (m, 7H), 1.55-2.10 (m, 9H), 2.10-2.40 (m, 2H), 2.75-2.95 (m, 2H), 3.0-3.12 (m, 1H), 3.12-3.70 (m, 6H), 3.80-3.95 (m, 1H), 5.14 (m, 1H), 6.0 (s, 1H, OH), 6.35-6.55 (m, 2H), 6.90-7.10 (m, 2H), 7.35-7.45 (m, 1H), 7.60-7.70 (m, 1H).

EXAMPLE 80

(3R)-3-[(2R)-2-Cyclohexyl-2-fur-2-yl-2-hydroxyacetoxy]-1-phenethyl-1-azoniabicyclo[2.2.2]octane trifluoroacetate The title compound was synthesised as in Example 78. The yield of the final step was 3.6 mg, 6%.

MS [M-CF₃COO]⁺: 438.

¹H-NMR (DMSO-d₆): δ 1.0-1.45 (m, 7H), 1.55-1.80 (m, 3H), 1.80-2.10 (m, 4H), 2.12-2.28 (m, 1H), 2.30 (m, 1H), 2.90-3.05 (m, 2H), 3.15-3.25 (m, 1H), 3.25-3.50 (m, 5H), 3.50-3.65 (m, 1H), 3.85-3.95 (m, 1H), 5.18 (m, 1H), 6.0 (s, 1H, OH), 6.38-6.48 (m, 2H), 7.24-7.40 (m, 5H), 7.65 (m, 1H).

EXAMPLE 81

(3R)-3-[(2R)-2-Cyclohexyl-2-fur-2-yl-2-hydroxyacetoxy]-1-(3-phenylpropyl)-1-azoniabicyclo[2.2.2]octane trifluoroacetate The title compound was synthesised as in Example 78. The yield of the final step was 5.8 mg, 10%.

MS [M-CF₃COO]⁺: 452.

¹H-NMR (DMSO-d₆): δ 1.0-1.42 (m, 7H), 1.55-1.77 (m, 3H), 1.77-2.05 (m, 6H), 2.18 (m, 1H), 2.27 (m, 1H), 2.55-2.65 (m, 2H), 3.02-3.12 (m, 1H), 3.12-3.60 (m, 6H), 3.77-3.90 (m, 1H), 5.13 (m, 1H), 5.98 (s, 1H, OH), 6.40 (m, 2H), 7.20-7.35 (m, 5H), 7.61 (m, 1H).

EXAMPLE 82

(3R)-3-[(2R)-2-Cyclopentyl-2-hydroxy-2-phenylacetoxy]-1-(3-phenoxypropyl)-1-azoniabicyclo[2.2.2]octane trifluoroacetate The title compound was synthesised according to methods c, and b from Intermediate I-5a. The yield of the final step was 9.4 mg, 15.6%.

MS [M-CF₃COO]⁺: 464

¹H-NMR (DMSO-d₆): δ 1.10-1.70 (m, 8H), 1.70-2.02 (m, 4H), 2.05-2.15 (m, 2H), 2.24 (m, 1H), 2.90-2.97 (m, 1H), 3.15-3.25 (m, 1H), 3.25-3.60 (m, 6H), 3.75-3.92 (m, 1H), 3.95-4.10 (m, 2H), 5.10 (m, 1H), 5.86 (s, 1H, OH), 6.90-7.0 (m, 3H), 7.20-7.40 (m, 5H), 7.56-7.66 (m, 2H).

EXAMPLE 83

(3R)-3-[(2R)-2-Cyclopentyl-2-hydroxy-2-phenylacetoxy]-1-phenethyl-1-azoniabicyclo[2.2.2]octane trifluoroacetate The title compound was synthesised as in Example 82. The yield of the final step was 5.0 mg, 8.8%.

MS [M-CF₃COO]⁺: 434

¹H-NMR (DMSO-d₆): δ 1.12-1.70 (m, 8H), 1.75-2.05 (m, 4H), 2.26 (m, 1H), 2.87-3.05 (m, 3H), 3.15-3.62 (m, 7H), 3.80-3.92 (m, 1H), 5.13 (m, 1H), 5.86 (s, 1H, OH), 7.24-7.44 (m 8H), 7.56-7.66 (m, 2H).

EXAMPLE 84

(3R)-3-[(2R)-2-Cyclopentyl-2-hydroxy-2-phenylacetoxy]-1-(3-phenylsulfanylpropyl)-1-azoniabicyclo[2.2.2]octane trifluoroacetate The title compound was synthesised as in Example 82. The yield of the final step was 3.2 mg, 5.1%.

MS [M-CF₃COO]⁺: 480

¹H-NMR (DMSO-d₆): δ 1.12-1.65 (m, 8H), 1.65-2.0 (m, 6H), 2.21 (m, 1H), 2.85-3.15 (m, 4H), 3.15-3.55 (m, 6H), 3.70-3.85 (m, 1H), 5.06 (m, 1H), 5.83 (s, 1H, OH), 7.20-7.46 (m, 8H), 7.54-7.64 (m, 2H).

EXAMPLE 85

(3R)-3-[(2S)-2-Cyclopentyl-2-hydroxy-2-phenylacetoxy]-1-(3-phenoxypropyl)-1-azoniabicyclo[2.2.2]octane trifluoroacetate The title compound was synthesised according to methods c, and b from Intermediate I-5b. The yield of the final step was 7.8 mg, 12.9%.

MS [M-CF₃COO]⁺: 464

¹H-NMR (DMSO-d₆): δ 1.15-1.35 (m, 2H), 1.35-2.0 (m, 10H), 2.0-2.30 (m, 3H), 2.95-3.10 (m, 1H), 3.20-3.60 (m, 7H), 3.80-3.95 (m, 1H), 3.97-4.10 (m, 2H), 5.09 (m, 1H), 5.84 (s, 1H, OH), 6.90-7.0 (m, 3H), 7.24-7.44 (m, 5H), 7.60-7.70 (m, 2H).

EXAMPLE 86

(3R)-3-[(2S)-2-Cyclopentyl-2-hydroxy-2-phenylacetoxy]-1-phenethyl-1-azoniabicyclo[2.2.2]octane trifluoroacetate The title compound was synthesised as in Example 85. The yield of the final step was 5.2 mg, 9.2%.

MS [M-CF$_3$COO]$^+$: 434

$^1$H-NMR (DMSO-d$_6$): δ 1.12-1.32 (m, 2H), 1.32-2.05 (m, 10H), 2.20 (m, 1H), 2.90-3.10 (m, 3H), 3.20-3.62 (m, 7H), 3.82-3.97 (m, 1H), 5.12 (m, 1H), 5.85 (s, 1H, OH), 7.22-7.45 (m, 8H), 7.60-7.70 (m, 2H).

EXAMPLE 87

(3R)-3-[(2S)-2-Cyclopentyl-2-hydroxy-2-phenylacetoxy]-1-(3-phenylsulfanylpropyl)-1-azoniabicyclo [2.2.2]octane trifluoroacetate The title compound was synthesised as in Example 85. The yield of the final step was 4.0 mg, 6.4%.

MS [M-CF$_3$COO]$^+$: 480

$^1$H-NMR (DMSO-d$_6$): δ 1.12-1.32 (m, 2H), 1.32-1.70 (m, 8H), 1.70-2.0 (m, 4H), 2.16 (m, 1H), 2.92-3.05 (m, 3H), 3.15-3.60 (m, 7H), 3.75-3.87 (m, 1H), 5.04 (m, 1H), 5.82 (s, 1H, OH), 7.20-7.44 (m, 8H), 7.58-7.68 (m, 2H).

EXAMPLE 88

(3R)-3-[(2S)-2-Cyclohexyl-2-hydroxy-2-thien-2-ylacetoxy]-1-(3-phenoxypropyl)-1-azoniabicyclo [2.2.2]octane trifluoroacetate The title compound was synthesised according to methods c, and b from intermediate I-6a. The yield of the final step was 3.2 mg, 5.1%.

MS [M-CF$_3$COO]$^+$: 484

$^1$H-NMR (DMSO-d$_6$): δ 1.0-1.45 (m, 7H), 1.55-1.80 (m, 3H), 1.80-2.20 (m, 7H), 2.25-2.35 (m, 1H), 3.20-3.28 (m, 1H), 3.28-3.42 (m, 5H), 3.42-3.55 (m, 1H), 3.85-3.95 (m, 1H), 4.01-4.05 (m, 2H), 5.17 (m, 1H), 6.16 (s, 1H, OH), 6.92-7.03 (m, 4H), 7.13-7.15 (m, 1H), 7.28-7.34 (m, 2H), 7.42-7.45 (m, 1H).

EXAMPLE 89

(3R)-3-[(2S)-2-Cyclohexyl-2-hydroxy-2-thien-2-ylacetoxy]-1-phenethyl-1-azoniabicyclo[2.2.2]octane trifluoroacetate The title compound was synthesised as in Example 88. The yield of the final step was 3.4 mg, 5.8%.

MS [M-CF$_3$COO]$^+$: 454

$^1$H-NMR (DMSO-d$_6$): δ 1.0-1.45 (m, 7H), 1.55-1.80 (m, 3H), 1.80-2.15 (m, 5H), 2.32 (m, 1H), 2.95-3.05 (m, 2H), 3.20-3.52 (m, 6H), 3.52-3.68 (m, 1H), 3.85-3.95 (m, 1H), 5.20 (m, 1H), 6.16 (s, 1H, OH), 7.0-7.04 (m, 1H), 7.10-7.15 (m, 1H), 7.25-7.40 (m, 5H), 7.43-7.46 (m, 1H).

EXAMPLE 90

1-[3-(3-Cyanophenoxy)propyl]-(3R)-3-[(2S)-2-cyclohexyl-2-hydroxy-2-thien-2-ylacetoxy]-1-azoniabicyclo[2.2.2]octane trifluoroacetate The title compound was synthesised as in Example 88. The yield of the final step was 8.4 mg, 12.7%.

MS [M-CF$_3$COO]$^+$: 509

$^1$H-NMR (DMSO-d$_6$): δ 1.0-1.45 (m, 7H), 1.55-1.70 (m, 3H), 1.70-2.20 (m, 7H), 2.31 (m, 1H), 3.20-3.27 (m, 1H), 3.25-3.50 (m, 5H), 3.45-3.60 (m, 1H), 3.85-3.95 (m, 1H), 4.05-4.15 (m, 2H), 5.18 (m, 1H), 6.16 (s, 1H, OH), 7.0-7.03 (m, 1H), 7.13-7.15 (m, 1H), 7.28-7.31 (m, 1H), 7.43-7.46 (m, 3H), 7.50-7.55 (m, 1H).

EXAMPLE 91

(3R)-3-[(2R)-2-Cyclohexyl-2-hydroxy-2-thien-2-ylacetoxy]-1-(3-phenoxypropyl)-1-azoniabicyclo [2.2.2]octane trifluoroacetate The title compound was synthesised according to methods c, and b from Intermediate I-6b (The Intermediate I-6b used herein contains aprox. 25% of I-6a, see previous description in method c). The yield of the final step was 3.0 mg, 4.8%.

MS [M-CF$_3$COO]$^+$: 484

$^1$H-NMR (DMSO-d$_6$): δ 1.0-1.50 (m, 7H), 1.55-2.22 (m, 10H), 2.25-2.35 (m, 1H), 3.20-3.45 (m, 5H), 3.45-3.60 (m, 1H), 3.85-3.95 (m, 1H), 4.0-4.10 (m, 2H), 5.17 (m, 1H), 6.14 (and 6.16) (s, 1H, OH, mixture of diastereomers aprox. 75:25), 6.93-7.03 (m, 4H), 7.13-7.17 (m, 1H), 7.28-7.35 (m, 2H), 7.42-7.45 (m, 1H).

EXAMPLE 92

(3R)-3-[(2R)-2-Cyclohexyl-2-hydroxy-2-thien-2-ylacetoxy]-1-phenethyl-1-azoniabicyclo[2.2.2]octane trifluoroacetate The title compound was synthesised as in Example 91. The yield of the final step was 2.6 mg, 4.4%.

MS [M-CF$_3$COO]$^+$: 454

$^1$H-NMR (DMSO-d$_6$): δ 1.50-1.70 (m, 7H), 1.55-2.20 (m, 8H), 2.28 (m, 1H), 2.95-3.10 (m, 2H), 3.20-3.52 (m, 6H), 3.52-3.65 (m, 1H), 3.85-3.97 (m, 1H), 5.15-5.25 (m, 1H), 6.14 (and 6.16), (s, 1H, OH, mixture of diastereomers aprox. 75:25), 6.98-7.04 (m, 1H), 7.13-7.16 (m, 1H), 7.25-7.40 (m, 5H), 7.43-7.46 (m, 1H).

EXAMPLE 93

1-[3-(3-Cyanophenoxy)propyl]-(3R)-3-[(2R)-2-cyclohexyl-2-hydroxy-2-thien-2-ylacetoxy]-1-azoniabicyclo[2.2.2]octane trifluoroacetate The title compound was synthesised as in Example 91. The yield of the final step was 5.0 mg, 7.5%.

MS [M-CF$_3$COO]$^+$: 509

$^1$H-NMR (DMSO-d$_6$): δ 1.0-1.50 (m, 7H), 1.55-2.05 (m, 7H), 2.05-2.22 (m, 3H), 2.22-2.35 (m, 1H), 3.20-3.50 (m, 6H), 3.45-3.60 (m, 1H), 3.80-3.95 (m, 1H), 4.10-4.15 (m, 2H), 5.17 (m, 1H), 6.14 (and 6.16) (s, 1H, OH, mixture of diastereomers aprox. 75:25), 7.0-7.03 (m, 1H), 7.13-7.16 (m, 1H), 7.28-7.32 (m, 1H), 7.43-7.46 (m, 3H), 7.50-7.55 (m, 1H).

EXAMPLE 94

(3R)-3-(2-Hydroxy-4-phenyl-2-thien-2-ylbutanoy-loxy)-1-(3-phenoxypropyl)-1-azoniabicyclo[2.2.2]octane trifluoroacetate The title compound was synthesised as a mixture of diastereomers according to methods d, and b from Intermediate I-21. The yield of the final step was 4.8 mg, 15.8%.
MS [M-CF$_3$COO]$^+$: 506
$^1$H-NMR (DMSO-d$_6$): δ 1.75-2.05 (m, 3H), 2.05-2.20 (m, 2H), 2.20-2.35 (m, 2H), 2.37-2.70 (m, 4H), 3.20-3.65 (m, 7H), 3.82-3.95 (m, 1H), 4.0-4.1 (m, 2H), 5.12 (m, 1H), 6.58 (s, 1H, OH), 6.90-7.0 (m, 3H), 7.0-7.08 (m, 1H), 7.14-7.24 (m, 4H), 7.24-7.36 (m, 4H), 7.46-7.52 (m, 1H).

EXAMPLE 95

(3S)-3-[(2S)-2-Cyclopentyl-2-hydroxy-2-thien-2-ylacetoxy]-1-(3-phenoxypropyl)-1-azoniabicyclo[2.2.2]octane bromide The title compound was synthesised according to methods c, and a from the Intermediate I-7. The yield of the final step was 250 mg, 87.1%.
MS [M-Br]$^+$: 470
$^1$H-NMR (DMSO-d$_6$): δ (Same description as in Example 53)

EXAMPLE 96

(3S)-3-[(2S)-2-Cyclopentyl-2-hydroxy-2-thien-2-ylacetoxy]-1-(3-thien-2-ylpropyl)-1-azoniabicyclo[2.2.2]octane trifluoroacetate The title compound was synthesised according to methods c, and b from the Intermediate I-7. The yield of the final step was 11.1 mg, 40.2%.
MS [M-CF$_3$COO]$^+$: 460
$^1$H-NMR (DMSO-d$_6$): δ (Same description as in Example 54)

EXAMPLE 97

(3S)-3-[(2S)-2-Cyclopentyl-2-hydroxy-2-thien-2-ylacetoxy]-1-(3-phenylpropyl)-1-azoniabicyclo[2.2.2]octane trifluoroacetate The title compound was synthesised as in Example 96. The yield of the final step was 11.3 mg, 41.4%.
MS [M-CF$_3$COO]$^+$: 454.
$^1$H-NMR (DMSO-d$_6$): δ (Same description as in Example 57).

EXAMPLE 98

4-[(2R)-2-Cyclohexyl-2-hydroxy-2-phenylacetoxy]-1-(3-thien-2-ylpropyl)-1-azoniabicyclo[2.2.2]octane trifluoroacetate The title compound was synthesised according to methods c, and b from the Intermediate I-8. The yield was 9.4 mg, 34.6%.
MS [M-CF$_3$COO]$^+$: 468
$^1$H-NMR (DMSO-d$_6$): δ 0.90-1.65 (m, 9H), 1.70-1.80 (m, 1H), 1.90-2.05 (m, 2H), 2.05-2.20 (m, 1H), 2.18-2.35 (m, 6H), 2.75-2.90 (m, 2H), 3.10-3.25 (m, 2H), 3.45-3.70 (m, 6H), 5.60 (s, 1H, OH), 6.90-6.92 (m, 1H), 6.95-7.02 (m, 1H), 7.20-7.45 (m, 4H), 7.50-7.60 (m, 2H).

EXAMPLE 99

4-[(2R)-2-Cyclohexyl-2-hydroxy-2-phenylacetoxy]-1-(3-phenoxypropyl)-1-azoniabicyclo[2.2.2]octane trifluoroacetate The title compound was synthesised as in Example 98. The yield of the final step was 8.1 mg, 29.2%.
MS [M-CF$_3$COO]$^+$: 478
$^1$H-NMR (DMSO-d$_6$): δ 0.90-1.65 (m, 9H), 1.70-1.80 (m, 1H), 2.05-2.20 (m, 3H), 2.20-2.40 (m, 6H), 3.20-3.45 (m, 2H), 3.50-3.75 (m, 6H), 3.95-4.10 (m, 2H), 5.60 (s, 1H, OH), 6.85-7.05 (m, 3H), 7.20-7.45 (m, 5H), 7.50-7.65 (m, 2H).
((*): Configuration not assigned)

The following examples illustrate pharmaceutical compositions according to the present invention and procedures for their preparation.

EXAMPLE 100

Preparation of a Pharmaceutical Composition

Tablets

Formulation:

| | |
|---|---|
| Compound of the present invention | 5.0 mg |
| Lactose | 113.6 mg |
| Microcrystalline cellulose | 28.4 mg |
| Light silicic anhydride | 1.5 mg |
| Magnesium stearate | 1.5 mg |

Using a mixer machine, 15 g of the compound of the present invention was mixed with 340.8 g of lactose and 85.2 g of microcrystalline cellulose. The mixture was subjected to compression moulding using a roller compactor to give a flake-like compressed material. The flake-like compressed material was pulverized using a hammer mill, and the pulverized material was screened through a 20 mesh screen. A 4.5 g portion of light silicic anhydride and 4.5 g of magnesium stearate were added to the screened material and mixed. The mixer product was subjected to a tablets making machine equipped with a die/punch system of 7.5 mm in diameter, thereby obtaining 3,000 tablets each having 150 mg in weight.

EXAMPLE 101

Preparation of a Pharmaceutical Composition

Tablets Coated

Formulation:

| | |
|---|---|
| Compound of the present invention | 5.0 mg |
| Lactose | 95.2 mg |
| Corn starch | 40.8 mg |
| Polyvinylpyrrolidone K25 | 7.5 mg |
| Magnesium stearate | 1.5 mg |
| Hydroxypropylcellulose | 2.3 mg |
| Polyethylene glycol 6000 | 0.4 mg |
| Titanium dioxide | 1.1 mg |
| Purified talc | 0.7 mg |

Using a fluidized bed granulating machine, 15 g of the compound of the present invention was mixed with 285.6 g of lactose and 122.4 g of corn starch. Separately, 22.5 g of polyvinylpyrrolidone was dissolved in 127.5 g of water to prepare a binding solution. Using a fluidized bed granulating machine, the binding solution was sprayed on the above mixture to give granulates. A 4.5 g portion of magnesium stearate was added to the obtained granulates and mixed. The obtained mixture was subjected to a tablet making machine equipped with a die/punch biconcave system of 6.5 mm in diameter, thereby obtaining 3,000 tablets, each having 150 mg in weight.

Separately, a coating solution was prepared by suspending 6.9 g of hydroxypropylmethylcellulose 2910, 1.2 g of polyethylene glycol 6000, 3.3 g of titanium dioxide and 2.1 g of purified talc in 72.6 g of water. Using a High Coated, the 3,000 tablets prepared above were coated with the coating solution to give film-coated tablets, each having 154.5 mg in weight.

EXAMPLE 102

Preparation of a Pharmaceutical Composition

Liquid Inhalant

Formulation:

| | |
|---|---|
| Compound of the present invention | 400 μg |
| Physiological saline | 1 ml |

A 40 mg portion of the compound of the present invention was dissolved in 90 ml of physiological saline, and the solution was adjusted to a total volume of 100 ml with the same saline solution, dispensed in 1 ml portions into 1 ml capacity ampoule and then sterilized at 115° for 30 minutes to give liquid inhalant.

EXAMPLE 103

Preparation of a Pharmaceutical Composition

Powder Inhalant

Formulation:

| | |
|---|---|
| Compound of the present invention | 200 μg |
| Lactose | 4,000 μg |

A 20 g portion of the compound of the present invention was uniformly mixed with 400 g of lactose, and a 200 mg portion of the mixture was packed in a powder inhaler for exclusive use to produce a powder inhalant.

EXAMPLE 104

Preparation of a Pharmaceutical Composition

Inhalation Aerosol

Formulation:

| | |
|---|---|
| Compound of the present invention | 200 μg |
| Dehydrated (Absolute) ethyl alcohol USP | 8,400 μg |
| 1,1,1,2-Tetrafluoroethane (HFC-134A) | 46,810 μg |

The active ingredient concentrate is prepared by dissolving 0.0480 g of the compound of the present invention in 2.0160 g of ethyl alcohol. The concentrate is added to an appropriate filling apparatus. The active ingredient concentrate is dispensed into aerosol container, the headspace of the container is purged with Nitrogen or HFC-134A vapor (purging ingredients should not contain more than 1 ppm oxygen) and is sealed with valve. 11.2344 g of HFC-134A propellant is then pressure filled into the sealed container.

The invention claimed is:

1. A combination which comprises (a) a compound of formula (I):

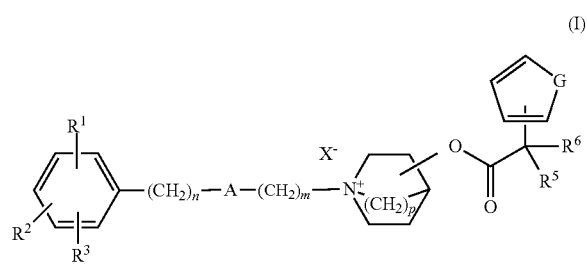

wherein $R^1$, $R^2$ and $R^3$ each independently represent a hydrogen or halogen atom, or, a phenyl group, —$OR^7$, —$SR^7$, —$NR^7R^8$, —$NHCOR^7$, —$CONR^7R^8$, —CN, —$NO_2$, —$COOR^7$ or —$CF_3$ group, or a straight or branched, substituted or unsubstituted lower alkyl group, wherein $R^7$ and $R^8$ each independently represent a hydrogen atom or a straight or branched lower alkyl group, or $R^1$ and $R^2$ together form an aromatic ring;

n is an integer from 0 to 4;

A represents a group selected from —$CH_2$, —CH=$CR^9$—, —$CR^9$=CH—, —$CR^9R^{10}$—, —CO—, —O—, —S—, —S(O)—, —$S(O)_2^-$ and —$NR^9$—, wherein $R^9$ and $R^{10}$ each independently represent a hydrogen atom or a straight or branched lower alkyl group;

m is an integer from 0 to 8, provided that when m is 0, A is not —$CH_2$—;

p is an integer from 1 to 2 and the substitution in the azonia bicyclic ring may be in the 2, 3 or 4 position including all possible configurations of the asymmetric carbons;

G represents O or S;

$R^5$ represents an alkyl group of 1 to 7 carbon atoms, an alkenyl group containing 2 to 7 carbon atoms, an alkynyl group containing 2 to 7 carbon atoms, a cycloalkyl group of 3 to 7 carbon atoms, or a group of formula:

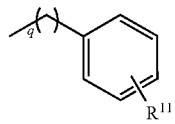

wherein q is 1 or 2 and $R^{11}$ represents a hydrogen or halogen atom, a hydroxy group, an alkoxy group, a nitro group, a cyano group, —$CO_2R^{12}$ or —$NR^{12}R^{13}$, wherein $R^{12}$ and $R^{13}$ are identical or different and are selected from hydrogen and straight or branched lower alkyl groups, or a straight or branched, substituted or unsubstituted lower alkyl group;

$R^6$ represents a hydrogen atom, a hydroxy group, a methyl group or a —$CH_2OH$ group; and X⁻ represents a pharmaceutically acceptable anion of a mono or polyvalent acid; and (b) a second compound which is a β₂ agonist, steroid, antiallergic drug, phosphodiesterase IV inhibitor and/or leukotriene D4 (LTD4) antagonist.

2. A combination according to claim 1, wherein p in formula (I) is 2.

3. A combination according to claim 1, wherein R⁵ in formula (I) represents a cyclopentyl, cyclohexyl, pentyl, allyl, vinyl, propynyl, benzyl or phenethyl group.

4. A combination according to claim 1 wherein the group—

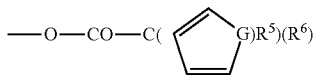

in formula (I) represents a group selected from 2-cyclopentyl-2-hydroxy-2-thien-2-ylacetoxy; 2-hydroxy-3-phenyl-2-thien-2-ylpropionyloxy; 2-hydroxy-2-thien-2-ylpent-4-enoyloxy; 2-hydroxy-2-thien-2-ylheptanoyloxy; 2-hydroxy-2-thien-2-ylpent-3-ynoyloxy; 2-hydroxy-2-thien-2-ylbut-3-enoyloxy; 2-cyclopentyl-2-fur-2-yl-2-hydroxyacetoxy; 2-cyclohexyl-2-fur-2-yl-2-hydroxyacetoxy; 2-cyclohexyl-2-hydroxy-2-thien-2-ylacetoxy and 2-hydroxy-4-phenyl-2-thien-2-ylbutanoyloxy.

5. A combination according to claim 1 wherein R¹, R² and R³ in formula (I) each independently represent a hydrogen or halogen atom or a hydroxy, methyl, tert-butyl, —CH₂OH, 3-hydroxypropyl, —OMe, —NMe₂-NHCOMe, —CONH₂, —CN, —NO₂, —CO₂Me or —CF₃ group.

6. A combination according to claim 5 wherein R¹, R² and R³ in formula (I) each independently represent a hydrogen or halogen atom or a hydroxy group.

7. A combination according to claim 1, wherein in formula (I) n is 0 or 1; m is an integer from 1 to 6; and A represents a —CH₂—, —CH=CH—, —CO—, —NMe-, —O— or —S— group.

8. A combination according to claim 7, wherein in formula (I) m is 1, 2 or 3 and A represents a —CH₂—, —CH=CH—, —O— or —S— group.

9. A combination according to claim 1, wherein the substituent on the nitrogen atom of the azoniabicyclo group in formula (I) is selected from the group consisting of 3-phenoxypropyl, 2-phenoxyethyl, 3-phenylallyl, phenethyl, 3-phenylpropyl, 3-(3-hydroxyphenoxy)propyl, 3-(4-fluorophenoxy)propyl, 2-benzyloxyethyl, 3-o-tolyloxypropyl, 3-(3-cyanophenoxy)propyl, 3-(methylphenylamino)propyl, 3-phenylsulfanylpropyl, 4-oxo-4-phenylbutyl, 3-(2-chlorophenoxy)propyl, 3-(2,4-difluorophenoxy)propyl, and 3-(4-methoxyphenoxy)propyl.

10. A combination according to claim 1, wherein X⁻ in formula (I) represents a chloride, bromide, trifluoroacetate or methanesulphonate anion.

11. A combination according to claim 1, wherein the azoniabicyclic group in formula (I) is substituted in the 3-position.

12. A combination according to claim 11, wherein the substituent at the 3-position of the azoniabicyclic group in formula (I) has R configuration.

13. A combination according to claim 11, wherein the substituent at the 3-position of the azoniabicyclic group in formula (I) has S configuration.

14. A combination according to claim 1, wherein in formula (I) the carbon substituted by

R⁵ and R⁶ has R configuration.

15. A combination according to claim 1 wherein in formula (I) the carbon substituted by

R⁵ and R⁶ has S configuration.

16. A combination according to claim 1, wherein the compound of formula (I) is present substantially as a single isomer.

17. A combination according to claim 1 wherein the compound of formula (I) is:
- (3R)-3-(2,3-Diphenylpropionyloxy)-1-(3-phenoxypropyl)-1-azoniabicyclo[2.2.2]octane trifluoroacetate
- (3R)-3-(2-Hydroxy-3-phenyl-2-thien-2-ylpropionyloxy)-1-(3-phenoxypropyl)-1-azoniabicyclo[2.2.2]octane trifluoroacetate
- (3R)-3-(2-Hydroxy-2-thien-2-ylpent-4-enoyloxy)-1-(3-phenoxypropyl)-1-azoniabicyclo[2.2.2]octane bromide
- (3R)-3-(2-Hydroxy-2-thien-2-ylpent-4-enoyloxy)-1-(2-phenoxyethyl)-1-azoniabicyclo[2.2.2]octane bromide
- (3R)-3-(2-Hydroxy-2-thien-2-ylheptanoyloxy)-1-(3-phenoxypropyl)-1-azoniabicyclo[2.2.2]octane trifluoroacetate
- (3R)-3-(2-Hydroxy-2-thien-2-ylpent-3-ynoyloxy)-1-(3-phenoxypropyl)-1-azoniabicyclo[2.2.2]octane trifluoroacetate
- (3R)-3-(2-Hydroxy-2-thien-2-ylbut-3-enoyloxy)-1-(3-phenoxypropyl)-1-azoniabicyclo[2.2.2]octane trifluoroacetate
- (3R)-3-[(2S)-2-Cyclopentyl-2-hydroxy-2-thien-2-ylacetoxy]-1-(3-phenoxypropyl)-1-azoniabicyclo[2.2.2]octane bromide
- (3R)-3-[(2S)-2-Cyclopentyl-2-hydroxy-2-thien-2-ylacetoxy]-1-(2-phenoxyethyl)-1-azoniabicyclo[2.2.2]octane bromide
- (3R)-3-[(2S)-2-Cyclopentyl-2-hydroxy-2-thien-2-ylacetoxy]-1-phenethyl-1-azoniabicyclo[2.2.2]octane trifluoroacetate
- (3R)-3-[(2S)-2-Cyclopentyl-2-hydroxy-2-thien-2-ylacetoxy]-1-(3-phenylpropyl)-1-azoniabicyclo[2.2.2]octane trifluoroacetate
- (3R)-3-[(2S)-2-Cyclopentyl-2-hydroxy-2-thien-2-ylacetoxy]-1-(3-phenylallyl)-1-azoniabicyclo[2.2.2]octane trifluoroacetate
- (3R)-3-[(2S)-2-Cyclopentyl-2-hydroxy-2-thien-2-ylacetoxy]-1-[3-(4-fluorophenoxy)propyl]-1-azoniabicyclo[2.2.2]octane trifluoroacetate
- (3R)-3-[(2S)-2-Cyclopentyl-2-hydroxy-2-thien-2-ylacetoxy]-1-[4-(4-fluorophenyl)-4-oxobutyl]-1-azoniabicyclo[2.2.2]octane trifluoroacetate
- (3R)-3-[(2S)-2-Cyclopentyl-2-hydroxy-2-thien-2-ylacetoxy]-1-[3-(3-hydroxyphenoxypropyl]-1-azoniabicyclo[2.2.2]octane trifluoroacetate
- 1-(2-Benzyloxyethyl)-(3R)-3-[(2S)-2-cyclopentyl-2-hydroxy-2-thien-2-ylacetoxy]-1-azoniabicyclo[2.2.2]octane trifluoroacetate (3R)-3-[(2S)-2-Cyclopentyl-2-hydroxy-2-thien-2-ylacetoxy]-1-(3-o-tolyloxypropyl)-1-azoniabicyclo[2.2.2]octane trifluoroacetate 1-[3-(3-Cyanophenoxy)propyl]-(3R)-3-[(2S)-2-cyclopentyl-2-hydroxy-2-thien-2-ylacetoxy]-1-azoniabicyclo[2.2.2]octane trifluoroacetate (3R)-3-[(2S)-2-Cyclopentyl-2-hydroxy-2-thien-2-ylacetoxy]-1-[3-(naphthalen-1-yloxy)propyl]-1-azoniabicyclo[2.2.2]octane trifluoroacetate (3R)-3-[(2S)-2-Cyclopentyl-2-hydroxy-2-thien-2-ylacetoxy]-1-[3-(methylphenylamino)propyl]-1-azoniabicyclo[2.2.2]octane trifluoroacetate (3R)-3-[(2S)-2-Cyclopentyl-2-hydroxy-2-thien-2-ylacetoxy]-1-(3-phenylsulfanylpropyl)-1-azoniabicyclo[2.2.2]octane trifluoroacetate (3R)-3-[(2S)-2-Cyclopentyl-2-hydroxy-2-thien-2-ylacetoxy]-1-(4-oxo-4-phenylbutyl)-1-azoniabicyclo[2.2.2]octane trifluoroacetate (3R)-3-[(2S)-2-Cyclopentyl-2-hydroxy-2-thien-2-ylacetoxy]-1-[3-(2,4,6-trimethylphenoxy)propyl]-1-azoniabicyclo[2.2.2]octane trifluoroacetate 1-[3-(2-Chlorophenoxy)propyl]-(3R)-3-[(2S)-2-cyclopentyl-2-hydroxy-2-thien-2-ylacetoxy]-1-azoniabicyclo[2.2.2]octane trifluoroacetate (3R)-3-[(2S)-2-Cyclopentyl-2-hydroxy-2-thien-2-ylacetoxy]-1-[3-(3-trifluoromethylphenoxy)propyl]-1-azoniabicyclo[2.2.2]octane trifluoroacetate 1-[3-(Biphenyl-4-yloxy)propyl]-(3R)-3-[(2S)-2-cyclopentyl-2-hydroxy-2-thien-2-ylacetoxy]-1-azoniabicyclo[2.2.2]octane trifluoroacetate (3R)-3-[(2S)-2-Cyclopentyl-2-hydroxy-2-thien-2-ylacetoxy]-1-[3-(2,4-difluorophenoxy)propyl]-1-azoniabicyclo[2.2.2]octane trifluoroacetate (3R)-3-[(2S)-2-Cyclopentyl-2-hydroxy-2-thien-2-ylacetoxy]-1-[3-(4-methoxyphenoxy)propyl]-1-azoniabicyclo[2.2.2]octane trifluoroacetate 1-[3-(2-Carbamoylphenoxy)propyl]-(3R)-3-[(2S)-2-cyclopentyl-2-hydroxy-2-thien-2-ylacetoxy]-1-azoniabicyclo[2.2.2]octane trifluoroacetate (3R)-3-[(2S)-2-Cyclopentyl-2-hydroxy-2-thien-2-ylacetoxy]-1-[3-(3-dimethylaminophenoxy)propyl]-1-azoniabicyclo[2.2.2]octane trifluoroacetate 1-[3-(4-Acetylaminophenoxy)propyl]-(3R)-3-[(2S)-2-cyclopentyl-2-hydroxy-2-thien-2-ylacetoxy]-1-azoniabicyclo[2.2.2]octane trifluoroacetate (3R)-3-[(2S)-2-Cyclopentyl-2-hydroxy-2-thien-2-ylacetoxy]-1-[3-(4-methoxycarbonylphenoxy)propyl]-1-azoniabicyclo[2.2.2]octane trifluoroacetate (3R)-3-[(2S)-2-Cyclopentyl-2-hydroxy-2-thien-2-ylacetoxy]-1-[3-(4-nitrophenoxy)propyl]-1-azoniabicyclo[2.2.2]octane trifluoroacetate (3R)-3-[(2S)-2-Cyclopentyl-2-hydroxy-2-thien-2-ylacetoxy]-1-[3-(4-hydroxymethylphenoxy)propyl]-1-azoniabicyclo[2.2.2]octane trifluoroacetate (3R)-3-[(2R)-2-cyclopentyl-2-hydroxy-2-thien-2-ylacetoxy]-1-(3-phenoxypropyl)-1-azoniabicyclo[2.2.2]octane bromide (3R)-3-[(2R)-2-Cyclopentyl-2-hydroxy-2-thien-2-ylacetoxy]-1-(2-phenoxyethyl)-1-azoniabicyclo[2.2.2]octane trifluoroacetate (3R)-3-[(2R)-2-Cyclopentyl-2-hydroxy-2-thien-2-ylacetoxy]-1-phenethyl-1-azoniabicyclo[2.2.2]octane trifluoroacetate (3R)-3-[(2R)-2-Cyclopentyl-2-hydroxy-2-thien-2-ylacetoxy]-1-(3-phenylpropyl)-1-azoniabicyclo[2.2.2]octane trifluoroacetate (3R)-3-[(2R)-2-Cyclopentyl-2-hydroxy-2-thien-2-ylacetoxy]-1-(3-phenylallyl)-1-azoniabicyclo[2.2.2]octane trifluoroacetate (3R)-3-[(2R)-2-Cyclopentyl-2-hydroxy-2-thien-2-ylacetoxy]-1-[3-(4-fluorophenoxy)propyl]-1-azoniabicyclo[2.2.2]octane trifluoroacetate (3R)-3-[(2S)-2-Cyclopentyl-2-fur-2-yl-2-hydroxyacetoxy]-1-(3-phenoxypropyl)-1-azoniabicyclo[2.2.2]octane trifluoroacetate (3R)-3-[(2S)-2-Cyclopentyl-2-fur-2-yl-2-hydroxyacetoxy]-1-phenethyl-1-azoniabicyclo[2.2.2]octane trifluoroacetate (3R)-3-[(2S)-2-Cyclopentyl-2-fur-2-yl-2-hydroxyacetoxy]-1-(3-phenylpropyl)-1-azoniabicyclo[2.2.2]octane trifluoroacetate (3R)-3-[(2R)-2-Cyclopentyl-2-fur-2-yl-2-hydroxyacetoxy]-1-(3-phenoxypropyl)-1-azoniabicyclo[2.2.2]octane trifluoroacetate (3R)-3-[(2R)-2-Cyclopentyl-2-fur-2-yl-2-hydroxyacetoxy]-1-phenethyl-1-azoniabicyclo[2.2.2]octane trifluoroacetate (3R)-3-[(2R)-2-Cyclopentyl-2-fur-2-yl-2-hydroxyacetoxy]-1-(3-phenylpropyl)-1-azoniabicyclo[2.2.2]octane trifluoroacetate (3R)-3-[(2S)-2-Cyclohexyl-2-fur-2-yl-2-hydroxyacetoxy]-1-(3-phenoxypropyl)-1-azoniabicyclo[2.2.2]octane trifluoroacetate (3R)-3-[(2S)-2-Cyclohexyl-2-fur-2-yl-2-hydroxyacetoxy]-1-phenethyl-1-azoniabicyclo[2.2.2]octane trifluoroacetate (3R)-3-[(2S)-2-Cyclohexyl-2-fur-2-yl-2-hydroxyacetoxy]-1-(3-phenylpropyl)-1-azoniabicyclo[2.2.2]octane trifluoroacetate (3R)-3-[(2R)-2-Cyclohexyl-2-fur-2-yl-2-hydroxyacetoxy]-1-(3-phenoxypropyl)-1-azoniabicyclo[2.2.2]octane trifluoroacetate (3R)-3-[(2R)-2-Cyclohexyl-2-fur-2-yl-2-hydroxyacetoxy]-1-phenethyl-1-azoniabicyclo[2.2.2]octane trifluoroacetate (3R)-3-[(2R)-2-Cyclohexyl-2-fur-2-yl-2-hydroxyacetoxy]-1-(3-phenylpropyl)-1-azoniabicyclo[2.2.2]octane trifluoroacetate (3R)-3-[(2S)-2-Cyclohexyl-2-hydroxy-2-thien-2-ylacetoxy]-1-(3-phenoxypropyl)-1-azoniabicyclo[2.2.2]octane trifluoroacetate (3R)-3-[(2S)-2-Cyclohexyl-2-hydroxy-2-thien-2-ylacetoxy]-1-phenethyl-1-azoniabicyclo[2.2.2]octane trifluoroacetate 1-[3-(3-Cyanophenoxy)propyl]-(3R)-3-[(2S)-2-cyclohexyl-2-hydroxy-2-thien-2-ylacetoxy]-1-azoniabicyclo[2.2.2]octane trifluoroacetate (3R)-3-[(2R)-2-Cyclohexyl-2-hydroxy-2-thien-2-ylacetoxy]-1-(3-phenoxypropyl)-1-azoniabicyclo[2.2.2]octane trifluoroacetate (3R)-3-[(2R)-2-Cyclohexyl-2-hydroxy-2-thien-2-ylacetoxy]-1-phenethyl-1-azoniabicyclo[2.2.2]octane trifluoroacetate 1-[3-(3-Cyanophenoxy)propyl]-(3R)-3-[(2R)-2-cyclohexyl-2-hydroxy-2-thien-2-ylacetoxy]-1-azoniabicyclo[2.2.2]octane trifluoroacetate (3R)-3-(2-Hydroxy-4-phenyl-2-thien-2-ylbutanoyloxy)-1-(3-phenoxypropyl)-1-azoniabicyclo[2.2.2]octane trifluoroacetate (3S)-3-[(2S)-2-Cyclopentyl-2-hydroxy-2-thien-2-ylacetoxy]-1-(3-phenoxypropyl)-1-azoniabicyclo[2.2.2]octane bromide (3S)-3-[(2S)-2-Cyclopentyl-2-hydroxy-2-thien-2-ylacetoxy]-1-(3-phenylpropyl)-1-azoniabicyclo[2.2.2]octane trifluoroacetate.

18. A pharmaceutical composition comprising (a) a compound of formula (I) as defined in claim 1 and (b) a second compound which is a $\beta_2$ agonist, steroid, antiallergic drug, phosphodiesterase IV inhibitor and/or leukotriene D4 (LTD4) antagonist in admixture with a pharmaceutically acceptable carrier or diluent.

19. A method of treating chronic obstructive pulmonary disease or asthma, which method comprises administering to a human or animal patient in need of treatment an effective non-toxic amount of a compound of formula (I) as defined in claim 1 wherein the compound of formula (I) as defined in claim 1 is administered simultaneously, separately or sequentially with a second compound which is a $\beta_2$ agonist, steroid, antiallergic drug, phosphodiesterase IV inhibitor and/or leukotriene D4 (LTD4) antagonist.

20. A combination according to claim 1, wherein each lower alkyl group in the compound of formula (I) is a $C_1$-$C_8$ group.

21. A combination according to claim 1, wherein said substituted lower alkyl group in the compound of formula (I) is a $C_1$-$C_8$ alkyl group substituted by 1, 2 or 3 substituents selected from halogen atoms and hydroxyl and $C_1$-$C_6$ alkoxy groups.

22. A combination product according to claim 1, wherein parts (a) and (b) are for simultaneous, separate or sequential use.

* * * * *